United States Patent
Loew et al.

(10) Patent No.: US 10,738,290 B2
(45) Date of Patent: Aug. 11, 2020

(54) RNA-GUIDED GENE EDITING SYSTEM AND USES THEREOF

(71) Applicant: Novartis AG, Basel (CH)

(72) Inventors: Andreas Loew, Somerville, MA (US); Anette Huebner, Basel (CH)

(73) Assignee: NOVARTIS AG, Basel (CH)

( * ) Notice: Subject to any disclaimer, the term of this patent is extended or adjusted under 35 U.S.C. 154(b) by 87 days.

(21) Appl. No.: 15/565,187

(22) PCT Filed: Apr. 20, 2016

(86) PCT No.: PCT/IB2016/052243
§ 371 (c)(1),
(2) Date: Oct. 9, 2017

(87) PCT Pub. No.: WO2016/170484
PCT Pub. Date: Oct. 27, 2016

(65) Prior Publication Data
US 2018/0080013 A1    Mar. 22, 2018

Related U.S. Application Data

(60) Provisional application No. 62/150,353, filed on Apr. 21, 2015.

(51) Int. Cl.
*C12N 9/22*     (2006.01)
*C12N 15/10*    (2006.01)
*C12N 15/63*    (2006.01)
*C12N 9/36*     (2006.01)
*C12N 15/113*   (2010.01)
*C12N 15/115*   (2010.01)
*A61K 38/00*    (2006.01)
*A61K 48/00*    (2006.01)

(52) U.S. Cl.
CPC ............ *C12N 9/22* (2013.01); *C12N 9/2462* (2013.01); *C12N 15/102* (2013.01); *C12N 15/113* (2013.01); *C12N 15/115* (2013.01); *C12N 15/63* (2013.01); *A61K 38/00* (2013.01); *A61K 48/00* (2013.01); *C07K 2319/09* (2013.01); *C07K 2319/21* (2013.01); *C07K 2319/85* (2013.01); *C12N 2310/11* (2013.01); *C12N 2310/16* (2013.01); *C12N 2310/3519* (2013.01); *C12N 2320/34* (2013.01); *C12N 2800/80* (2013.01)

(58) Field of Classification Search
CPC ....................................................... C12N 9/22
See application file for complete search history.

(56) References Cited

U.S. PATENT DOCUMENTS

| | | |
|---|---|---|
| 2015/0211023 A1 | 7/2015 | Shiboleth et al. |
| 2017/0183687 A1 | 6/2017 | Shiboleth et al. |
| 2017/0233752 A1 | 8/2017 | Shiboleth et al. |

FOREIGN PATENT DOCUMENTS

| | | | | |
|---|---|---|---|---|
| WO | 2013/088446 A1 | 6/2013 | | |
| WO | WO2013/088446 | * | 6/2013 | ......... A61K 31/7105 |

OTHER PUBLICATIONS

International Search Report and Written Opinion from PCT/IB2016/052243 dated May 10, 2016.

Cho E J et al. "Optimization of aptamer microarray technology for multiple protein targets" Analytica Chimica Acta, Elsevier, (2006), vol. 564, No. I, pp. 82-90.

C.S. Padlan et al. "An RNA aptamer possessing a novel monovalent cation-mediated fold inhibits lysozyme catalysis by inhibiting the binding of long natural substrates" RNA, (2014), vol. 20, No. 4, pp. 447-461.

T. Xu et al. "Cas9-Based Tools for Targeted Genome Editing and Transcriptional Control" Applied and Environmental Microbiology, (2014), vol. 80, No. 5, pp. 1544-1552.

Magdy M. Mahfouz et al. "Genome engineering via TALENs and CRISPR/Cas9 systems: challenges and perspectives" Plant Biotechnology Journal, (2014), vol. 12, No. 8, pp. 1006-1014.

* cited by examiner

*Primary Examiner* — Scott Long
(74) *Attorney, Agent, or Firm* — Yichen Liu

(57) ABSTRACT

The present invention provides RNA-guided gene editing systems and methods of use thereof.

15 Claims, 3 Drawing Sheets
Specification includes a Sequence Listing.

SEQUENCE LISTING

```
<160> NUMBER OF SEQ ID NOS: 72

<210> SEQ ID NO 1
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: Variation
<222> LOCATION: (2)..(30)
<223> OTHER INFORMATION: /replace=" "
<220> FEATURE:
<221> NAME/KEY: misc_feature
<222> LOCATION: (1)..(30)
<223> OTHER INFORMATION: /note="This sequence may encompass 1-30
      nucleotides"
<220> FEATURE:
<221> NAME/KEY: misc_feature
<222> LOCATION: (1)..(30)
<223> OTHER INFORMATION: /note="Variant nucleotides given in the
      sequence have no preference with respect to those in the
      annotations for variant positions"

<400> SEQUENCE: 1
aaaaaaaaaa aaaaaaaaaa aaaaaaaaaa                                        30

<210> SEQ ID NO 2
<211> LENGTH: 148
<212> TYPE: PRT
<213> ORGANISM: Homo sapiens

<400> SEQUENCE: 2

Met Lys Ala Leu Ile Val Leu Gly Leu Val Leu Leu Ser Val Thr Val
1               5                   10                  15

Gln Gly Lys Val Phe Glu Arg Cys Glu Leu Ala Arg Thr Leu Lys Arg
            20                  25                  30

Leu Gly Met Asp Gly Tyr Arg Gly Ile Ser Leu Ala Asn Trp Met Cys
        35                  40                  45

Leu Ala Lys Trp Glu Ser Gly Tyr Asn Thr Arg Ala Thr Asn Tyr Asn
    50                  55                  60
```

-continued

```
Ala Gly Asp Arg Ser Thr Asp Tyr Gly Ile Phe Gln Ile Asn Ser Arg
 65                 70                  75                  80

Tyr Trp Cys Asn Asp Gly Lys Thr Pro Gly Ala Val Asn Ala Cys His
                 85                  90                  95

Leu Ser Cys Ser Ala Leu Leu Gln Asp Asn Ile Ala Asp Ala Val Ala
            100                 105                 110

Cys Ala Lys Arg Val Val Arg Asp Pro Gln Gly Ile Arg Ala Trp Val
        115                 120                 125

Ala Trp Arg Asn Arg Cys Gln Asn Arg Asp Val Arg Gln Tyr Val Gln
    130                 135                 140

Gly Cys Gly Val
145

<210> SEQ ID NO 3
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 3
gggaauggau ccacaucuac gaauucauca gggcuaaaga gtgcagaguu acuuaguuca        60
cugcagacuu ga                                                            72

<210> SEQ ID NO 4
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ccuccggcuc auaccuuuuc gaagacaagc uucgacagga gg                           42

<210> SEQ ID NO 5
<211> LENGTH: 76
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
gcgcuaaguc cucgcucagc ccauaaguug ucccaagucu ugggcgcaaa uacaucccac        60
gcgcgacucg gauccg                                                        76

<210> SEQ ID NO 6
<211> LENGTH: 107
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
```

```
gauaauacga cucacuauag gguucacugc agacuugacg aagcuugcag aaaaggggga    60
agaagagggu gauucaggcg agagaaugga uccacaucua cgaauuc                 107
```

<210> SEQ ID NO 7
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Gly Ser His His His His His His
1               5

<210> SEQ ID NO 8
<211> LENGTH: 56
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8

```
ggguacgcuc agguauauug gcgccuucgu ggaaugucag ugccuggacg ugcagu    56
```

<210> SEQ ID NO 9
<211> LENGTH: 159
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
                20                  25                  30

Ala Gly Ala Asp Gly Ala Leu Thr Gly Thr Tyr Glu Ser Ala Val Gly
            35                  40                  45

Asn Ala Glu Ser Arg Tyr Val Leu Thr Gly Arg Tyr Asp Ser Ala Pro
        50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 10
<211> LENGTH: 108

<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10

```
gcgugagacg ucuugaugaa auccggcucg gcaaugguuc guggcgaauu gggugggaa      60 aguccugaaa agagggccac cacagaagcu uguggaguua acagcaaa                 108
```

<210> SEQ ID NO 11
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 11

```
ggggcacgtt tatccgtccc tcctagtggc gtgcccc                              37
```

<210> SEQ ID NO 12
<211> LENGTH: 198
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Gly Ser Gln Leu Val Lys Ser Glu Leu Glu Glu Lys Ser Glu Leu
1               5                   10                  15

Arg His Lys Leu Lys Tyr Val Pro His Glu Tyr Ile Glu Leu Ile Glu
                20                  25                  30

Ile Ala Arg Asn Ser Thr Gln Asp Arg Ile Leu Glu Met Lys Val Met
            35                  40                  45

Glu Phe Phe Met Lys Val Tyr Gly Tyr Arg Gly Lys His Leu Gly Gly
        50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Tyr Asn Leu
                85                  90                  95

Pro Ile Gly Gln Ala Asp Glu Met Gln Arg Tyr Val Glu Glu Asn Gln
            100                 105                 110

Thr Arg Asn Lys His Ile Asn Pro Asn Glu Trp Trp Lys Val Tyr Pro
        115                 120                 125

Ser Ser Val Thr Glu Phe Lys Phe Leu Phe Val Ser Gly His Phe Lys
130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
        195
```

```
<210> SEQ ID NO 13
<211> LENGTH: 206
<212> TYPE: PRT
<213> ORGANISM: Enterobacteria phage RB7

<400> SEQUENCE: 13
```

Met Lys Ser Gly Ile Tyr Gln Ile Lys Asn Thr Leu Asn Asn Lys Val
1               5                   10                  15

Tyr Val Gly Ser Ala Lys Asp Phe Glu Lys Arg Trp Lys Arg His Phe
            20                  25                  30

Lys Asp Leu Glu Lys Gly Cys His Ser Ser Ile Lys Leu Gln Arg Ser
        35                  40                  45

Phe Asn Lys His Gly Asn Val Phe Glu Cys Ser Ile Leu Glu Glu Ile
    50                  55                  60

Pro Tyr Glu Lys Asp Leu Ile Ile Glu Arg Glu Asn Phe Trp Ile Lys
65                  70                  75                  80

Glu Leu Asn Ser Lys Ile Asn Gly Tyr Asn Ile Ala Asp Ala Thr Phe
                85                  90                  95

Gly Asp Thr Cys Ser Thr His Pro Leu Lys Glu Ile Ile Lys Lys
            100                 105                 110

Arg Ser Glu Thr Val Lys Ala Lys Met Leu Lys Leu Gly Pro Asp Gly
        115                 120                 125

Arg Lys Ala Leu Tyr Ser Lys Pro Gly Ser Lys Asn Gly Arg Trp Asn
130                 135                 140

Pro Glu Thr His Lys Phe Cys Lys Cys Gly Val Arg Ile Gln Thr Ser
145                 150                 155                 160

Ala Tyr Thr Cys Ser Lys Cys Arg Asn Arg Ser Gly Leu Asn Asn Ser
                165                 170                 175

Phe Phe Asn His Lys His Ser Asp Ile Thr Lys Ser Lys Ile Ser Glu
            180                 185                 190

Lys Met Lys Gly Lys Lys Pro Ser Asn Ile Lys Ile Ser
        195                 200                 205

```
<210> SEQ ID NO 14
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14
```

Met Lys Ile Ile Glu Gln Leu Pro Ser Ala
1               5                   10

```
<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15
```

Val Arg His Lys Leu Lys Arg Val Gly Ser
1               5                   10

```
<210> SEQ ID NO 16
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Val Pro Phe Leu Leu Glu Pro Asp Asn Ile Asn Gly Lys Thr Cys
1               5                   10                  15

<210> SEQ ID NO 17
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly His Gly Thr Gly Ser Thr Gly Ser Gly Ser Ser
1               5                   10

<210> SEQ ID NO 18
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Met Ser Arg Pro Asp Pro Ala
1               5

<210> SEQ ID NO 19
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Ser Ala Gly Ser Ala Ala Gly Ser Gly Glu Phe
1               5                   10

<210> SEQ ID NO 20
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Gly Ser Glu Thr Pro Gly Thr Ser Glu Ser Ala
1               5                   10

<210> SEQ ID NO 21
<211> LENGTH: 16
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 21

Ser Gly Ser Glu Thr Pro Gly Thr Ser Glu Ser Ala Thr Pro Glu Ser
1               5                   10                  15

<210> SEQ ID NO 22
<211> LENGTH: 7
<212> TYPE: PRT
<213> ORGANISM: Simian virus 40

<400> SEQUENCE: 22

Pro Lys Lys Lys Arg Lys Val
1               5

<210> SEQ ID NO 23
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 23

Lys Arg Pro Ala Ala Thr Lys Lys Ala Gly Gln Ala Lys Lys Lys Lys
1               5                   10                  15

<210> SEQ ID NO 24
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 24

Pro Ala Ala Lys Arg Val Lys Leu Asp
1               5

<210> SEQ ID NO 25
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 25

Arg Gln Arg Arg Asn Glu Leu Lys Arg Ser Pro
1               5                   10

<210> SEQ ID NO 26
<211> LENGTH: 38
<212> TYPE: PRT
<213> ORGANISM: Homo sapiens

<400> SEQUENCE: 26

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
```

<210> SEQ ID NO 27
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 27

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40

<210> SEQ ID NO 28
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 28

Val Ser Arg Lys Arg Pro Arg Pro
1               5

<210> SEQ ID NO 29
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 29

Pro Pro Lys Lys Ala Arg Glu Asp
1               5

<210> SEQ ID NO 30
<211> LENGTH: 8
<212> TYPE: PRT
<213> ORGANISM: Homo sapiens

<400> SEQUENCE: 30

Pro Gln Pro Lys Lys Lys Pro Leu
1               5

<210> SEQ ID NO 31
<211> LENGTH: 12
<212> TYPE: PRT
<213> ORGANISM: Mus musculus

<400> SEQUENCE: 31

Ser Ala Leu Ile Lys Lys Lys Lys Lys Met Ala Pro
1               5                   10

<210> SEQ ID NO 32
<211> LENGTH: 5
<212> TYPE: PRT

<213> ORGANISM: Influenza virus

<400> SEQUENCE: 32

Asp Arg Leu Arg Arg
1               5

<210> SEQ ID NO 33
<211> LENGTH: 7
<212> TYPE: PRT
<213> ORGANISM: Influenza virus

<400> SEQUENCE: 33

Pro Lys Gln Lys Lys Arg Lys
1               5

<210> SEQ ID NO 34
<211> LENGTH: 10
<212> TYPE: PRT
<213> ORGANISM: Hepatitis delta virus

<400> SEQUENCE: 34

Arg Lys Leu Lys Lys Lys Ile Lys Lys Leu
1               5                   10

<210> SEQ ID NO 35
<211> LENGTH: 10
<212> TYPE: PRT
<213> ORGANISM: Mus musculus

<400> SEQUENCE: 35

Arg Glu Lys Lys Lys Phe Leu Lys Arg Arg
1               5                   10

<210> SEQ ID NO 36
<211> LENGTH: 20
<212> TYPE: PRT
<213> ORGANISM: Homo sapiens

<400> SEQUENCE: 36

Lys Arg Lys Gly Asp Glu Val Asp Gly Val Asp Glu Val Ala Lys Lys
1               5                   10                  15

Lys Ser Lys Lys
            20

<210> SEQ ID NO 37
<211> LENGTH: 17
<212> TYPE: PRT
<213> ORGANISM: Homo sapiens

<400> SEQUENCE: 37

Arg Lys Cys Leu Gln Ala Gly Met Asn Leu Glu Ala Arg Lys Thr Lys
1               5                   10                  15

Lys

<210> SEQ ID NO 38
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

Gly Gly Gly Ser
1

<210> SEQ ID NO 39
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 39
augcggccgc cgaccagaau catgcaagug cguaagauag ucgcgggucg gcggccgcau    60

<210> SEQ ID NO 40
<211> LENGTH: 330
<212> TYPE: PRT
<213> ORGANISM: Homo sapiens

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
ggaggugcuc cgaaaggaac ucc                                             23

<210> SEQ ID NO 42
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Gly Gly Gly Ser Gly Gly Gly Ser Gly Gly Gly Gly Ser Gly
1               5                   10                  15

Gly Gly Gly Ser
            20

<210> SEQ ID NO 43
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Gly Gly Gly Ser Gly Gly Gly Ser Gly Gly Gly Gly Ser
1               5                   10                  15

<210> SEQ ID NO 44
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Gly Gly Ser
1

<210> SEQ ID NO 45
<211> LENGTH: 9
<212> TYPE: PRT
```

```
<213> ORGANISM: Unknown
<220> FEATURE:
<221> NAME/KEY: source
<223> OTHER INFORMATION: /note="Description of Unknown:
      'LAGLIDADG' family motif peptide"

<400> SEQUENCE: 45

Leu Ala Gly Leu Ile Asp Ala Asp Gly
1               5

<210> SEQ ID NO 46
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (4)..(60)
<223> OTHER INFORMATION: /replace=" "
<220> FEATURE:
<221> NAME/KEY: misc_feature
<222> LOCATION: (1)..(60)
<223> OTHER INFORMATION: /note="This sequence may encompass 1-20 'Gly
      Gly Ser' repeating units"
<220> FEATURE:
<221> NAME/KEY: misc_feature
<222> LOCATION: (1)..(60)
<223> OTHER INFORMATION: /note="Variant residues given in the sequence
      have no preference with respect to those in the annotations
      for variant positions"

<400> SEQUENCE: 46

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser
    50                  55                  60

<210> SEQ ID NO 47
<211> LENGTH: 80
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (5)..(80)
<223> OTHER INFORMATION: /replace=" "
<220> FEATURE:
<221> NAME/KEY: misc_feature
<222> LOCATION: (1)..(80)
<223> OTHER INFORMATION: /note="This sequence may encompass 1-20 'Gly
      Gly Gly Ser' repeating units"
<220> FEATURE:
<221> NAME/KEY: misc_feature
<222> LOCATION: (1)..(80)
<223> OTHER INFORMATION: /note="Variant residues given in the sequence
      have no preference with respect to those in the annotations
      for variant positions"

<400> SEQUENCE: 47

Gly Gly Gly Ser Gly Gly Gly Ser Gly Gly Gly Ser Gly Gly Gly Ser
1               5                   10                  15
```

Gly Gly Gly Ser Gly Gly Gly Ser Gly Gly Gly Ser
            20              25              30

Gly Gly Gly Ser Gly Gly Gly Ser Gly Gly Gly Ser
        35              40              45

Gly Gly Gly Ser Gly Gly Gly Ser Gly Gly Gly Ser
    50              55              60

Gly Gly Gly Ser Gly Gly Gly Ser Gly Gly Gly Ser
65              70              75              80

<210> SEQ ID NO 48
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (6)..(100)
<223> OTHER INFORMATION: /replace=" "
<220> FEATURE:
<221> NAME/KEY: misc_feature
<222> LOCATION: (1)..(100)
<223> OTHER INFORMATION: /note="This sequence may encompass 1-20 'Gly
      Gly Gly Gly Ser' repeating units"
<220> FEATURE:
<221> NAME/KEY: misc_feature
<222> LOCATION: (1)..(100)
<223> OTHER INFORMATION: /note="Variant residues given in the sequence
      have no preference with respect to those in the annotations
      for variant positions"

<400> SEQUENCE: 48

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Ser Gly Gly Gly Gly Ser Gly
                85                  90                  95

Gly Gly Gly Ser
            100

<210> SEQ ID NO 49
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Lys Ser Glu Leu Arg His Lys Leu Lys Tyr Val Pro His Glu Tyr Ile
1               5                   10                  15

Glu Leu Ile Glu Ile Ala Arg Asn Ser Thr Gln Asp Arg Ile Leu Glu
            20                  25                  30

```
Met Lys Val Met Glu Phe Phe Met Lys Val Tyr Gly Tyr Arg Gly Lys
             35                  40                  45
His Leu Gly Gly Ser Arg Lys Pro Asp Gly Ala Ile Tyr Thr Val Gly
 50                  55                  60
Ser Pro Ile Asp Tyr Gly Val Ile Val Asp Thr Lys Ala Tyr Ser Gly
 65                  70                  75                  80
Gly Tyr Asn Leu Pro Ile Gly Gln Ala Asp Glu Met Gln Arg Tyr Val
                 85                  90                  95
Glu Glu Asn Gln Thr Arg Asn Lys His Ile Asn Pro Asn Glu Trp Trp
                100                 105                 110
Lys Val Tyr Pro Ser Ser Val Thr Glu Phe Lys Phe Leu Phe Val Ser
                115                 120                 125
Gly His Phe Lys Gly Asn Tyr Lys Ala Gln Leu Thr Arg Leu Asn His
            130                 135                 140
Ile Thr Asn Cys Asn Gly Ala Val Leu Ser Val Glu Glu Leu Leu Ile
145                 150                 155                 160
Gly Gly Glu Met Ile Lys Ala Gly Thr Leu Thr Leu Glu Glu Val Arg
                165                 170                 175
Arg Lys Phe Asn Asn Gly Glu Ile Asn Phe
                180                 185

<210> SEQ ID NO 50
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Lys Val Phe Glu Arg Cys Glu Leu Ala Arg Thr Leu Lys Arg Leu Gly
 1               5                  10                  15
Met Asp Gly Tyr Arg Gly Ile Ser Leu Ala Asn Trp Met Cys Leu Ala
                20                  25                  30
Lys Trp Glu Ser Gly Tyr Asn Thr Arg Ala Thr Asn Tyr Asn Ala Gly
             35                  40                  45
Asp Arg Ser Thr Asp Tyr Gly Ile Phe Gln Ile Asn Ser Arg Tyr Trp
 50                  55                  60
Cys Asn Asp Gly Lys Thr Pro Gly Ala Val Asn Ala Cys His Leu Ser
 65                  70                  75                  80
Cys Ser Ala Leu Leu Gln Asp Asn Ile Ala Asp Ala Val Ala Cys Ala
                 85                  90                  95
Lys Arg Val Val Arg Asp Pro Gln Gly Ile Arg Ala Trp Val Ala Trp
                100                 105                 110
Arg Asn Arg Cys Gln Asn Arg Asp Val Arg Gln Tyr Val Gln Gly Cys
            115                 120                 125
Gly Val
    130

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 51

Arg Gly Ser His His His His His His His
1               5                   10

<210> SEQ ID NO 52
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 52

His His His His His His
1               5

<210> SEQ ID NO 53
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 8xHis tag"

<400> SEQUENCE: 53

His His His His His His His His
1               5

<210> SEQ ID NO 54
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gly Ser Lys Asp His Ile Leu Gln Phe Val Ile Pro Asn Arg Leu Val
1               5                   10                  15

Lys Ser Glu Leu Glu Glu Lys
            20

<210> SEQ ID NO 55
<211> LENGTH: 204
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Lys Ser Glu Leu Arg His Lys Leu Lys Tyr Val Pro His Glu Tyr Ile
1               5                   10                  15

Glu Leu Ile Glu Ile Ala Arg Asn Ser Thr Gln Asp Arg Ile Leu Glu
            20                  25                  30

Met Lys Val Met Glu Phe Phe Met Lys Val Tyr Gly Tyr Arg Gly Lys
        35                  40                  45

His Leu Gly Gly Ser Arg Lys Pro Asp Gly Ala Ile Tyr Thr Val Gly
    50                  55                  60

Ser Pro Ile Asp Tyr Gly Val Ile Val Asp Thr Lys Ala Tyr Ser Gly
65                  70                  75                  80
```

```
Gly Tyr Asn Leu Pro Ile Gly Gln Ala Asp Glu Met Gln Arg Tyr Val
                85                  90                  95

Glu Glu Asn Gln Thr Arg Asn Lys His Ile Asn Pro Asn Glu Trp Trp
            100                 105                 110

Lys Val Tyr Pro Ser Ser Val Thr Glu Phe Lys Phe Leu Phe Val Ser
        115                 120                 125

Gly His Phe Lys Gly Asn Tyr Lys Ala Gln Leu Thr Arg Leu Asn His
    130                 135                 140

Ile Thr Asn Cys Asn Gly Ala Val Leu Ser Val Glu Glu Leu Leu Ile
145                 150                 155                 160

Gly Gly Glu Met Ile Lys Ala Gly Thr Leu Thr Leu Glu Glu Val Arg
                165                 170                 175

Arg Lys Phe Asn Asn Gly Glu Ile Asn Phe Gly Gly Gly Ser Gly
            180                 185                 190

Gly Gly Gly Ser His His His His His His
        195                 200
```

```
<210> SEQ ID NO 56
<211> LENGTH: 207
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Arg Gly Ser His His His His His His Gly Gly Gly Gly Ser
1               5                   10                  15

Gly Gly Gly Gly Ser Lys Ser Glu Leu Arg His Lys Leu Lys Tyr Val
                20                  25                  30

Pro His Glu Tyr Ile Glu Leu Ile Glu Ile Ala Arg Asn Ser Thr Gln
            35                  40                  45

Asp Arg Ile Leu Glu Met Lys Val Met Glu Phe Phe Met Lys Val Tyr
        50                  55                  60

Gly Tyr Arg Gly Lys His Leu Gly Gly Ser Arg Lys Pro Asp Gly Ala
65                  70                  75                  80

Ile Tyr Thr Val Gly Ser Pro Ile Asp Tyr Gly Val Ile Val Asp Thr
                85                  90                  95

Lys Ala Tyr Ser Gly Gly Tyr Asn Leu Pro Ile Gly Gln Ala Asp Glu
            100                 105                 110

Met Gln Arg Tyr Val Glu Glu Asn Gln Thr Arg Asn Lys His Ile Asn
        115                 120                 125

Pro Asn Glu Trp Trp Lys Val Tyr Pro Ser Ser Val Thr Glu Phe Lys
    130                 135                 140

Phe Leu Phe Val Ser Gly His Phe Lys Gly Asn Tyr Lys Ala Gln Leu
145                 150                 155                 160

Thr Arg Leu Asn His Ile Thr Asn Cys Asn Gly Ala Val Leu Ser Val
                165                 170                 175

Glu Glu Leu Leu Ile Gly Gly Glu Met Ile Lys Ala Gly Thr Leu Thr
            180                 185                 190

Leu Glu Glu Val Arg Arg Lys Phe Asn Asn Gly Glu Ile Asn Phe
        195                 200                 205
```

```
<210> SEQ ID NO 57
<211> LENGTH: 220
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Arg Gly Ser His His His His His His Gly Ser Lys Asp His
1               5                   10                  15

Ile Leu Gln Phe Val Ile Pro Asn Arg Leu Val Lys Ser Glu Leu Glu
            20                  25                  30

Glu Lys Lys Ser Glu Leu Arg His Lys Leu Lys Tyr Val Pro His Glu
        35                  40                  45

Tyr Ile Glu Leu Ile Glu Ile Ala Arg Asn Ser Thr Gln Asp Arg Ile
    50                  55                  60

Leu Glu Met Lys Val Met Glu Phe Phe Met Lys Val Tyr Gly Tyr Arg
65                  70                  75                  80

Gly Lys His Leu Gly Gly Ser Arg Lys Pro Asp Gly Ala Ile Tyr Thr
                85                  90                  95

Val Gly Ser Pro Ile Asp Tyr Gly Val Ile Val Asp Thr Lys Ala Tyr
            100                 105                 110

Ser Gly Gly Tyr Asn Leu Pro Ile Gly Gln Ala Asp Glu Met Gln Arg
        115                 120                 125

Tyr Val Glu Glu Asn Gln Thr Arg Asn Lys His Ile Asn Pro Asn Glu
    130                 135                 140

Trp Trp Lys Val Tyr Pro Ser Ser Val Thr Glu Phe Lys Phe Leu Phe
145                 150                 155                 160

Val Ser Gly His Phe Lys Gly Asn Tyr Lys Ala Gln Leu Thr Arg Leu
                165                 170                 175

Asn His Ile Thr Asn Cys Asn Gly Ala Val Leu Ser Val Glu Glu Leu
            180                 185                 190

Leu Ile Gly Gly Glu Met Ile Lys Ala Gly Thr Leu Thr Leu Glu Glu
        195                 200                 205

Val Arg Arg Lys Phe Asn Asn Gly Glu Ile Asn Phe
    210                 215                 220

<210> SEQ ID NO 58
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Lys Ser Glu Leu Arg His Lys Leu Lys Tyr Val Pro His Glu Tyr Ile
1               5                   10                  15

Glu Leu Ile Glu Ile Ala Arg Asn Ser Thr Gln Asp Arg Ile Leu Glu
            20                  25                  30

Met Lys Val Met Glu Phe Phe Met Lys Val Tyr Gly Tyr Arg Gly Lys
        35                  40                  45

His Leu Gly Gly Ser Arg Lys Pro Asp Gly Ala Ile Tyr Thr Val Gly
    50                  55                  60

Ser Pro Ile Asp Tyr Gly Val Ile Val Asp Thr Lys Ala Tyr Ser Gly
65                  70                  75                  80

Gly Tyr Asn Leu Pro Ile Gly Gln Ala Asp Glu Met Gln Arg Tyr Val
```

```
                    85                  90                  95
Glu Glu Asn Gln Thr Arg Asn Lys His Ile Asn Pro Asn Glu Trp Trp
                100                 105                 110
Lys Val Tyr Pro Ser Ser Val Thr Glu Phe Lys Phe Leu Phe Val Ser
                115                 120                 125
Gly His Phe Lys Gly Asn Tyr Lys Ala Gln Leu Thr Arg Leu Asn His
            130                 135                 140
Ile Thr Asn Cys Asn Gly Ala Val Leu Ser Val Glu Glu Leu Leu Ile
145                 150                 155                 160
Gly Gly Glu Met Ile Lys Ala Gly Thr Leu Thr Leu Glu Glu Val Arg
                165                 170                 175
Arg Lys Phe Asn Asn Gly Glu Ile Asn Phe Gly Gly Gly Ser Gly
                180                 185                 190
Gly Gly Gly Ser Lys Val Phe Glu Arg Cys Glu Leu Ala Arg Thr Leu
            195                 200                 205
Lys Arg Leu Gly Met Asp Gly Tyr Arg Gly Ile Ser Leu Ala Asn Trp
210                 215                 220
Met Cys Leu Ala Lys Trp Glu Ser Gly Tyr Asn Thr Arg Ala Thr Asn
225                 230                 235                 240
Tyr Asn Ala Gly Asp Arg Ser Thr Asp Tyr Gly Ile Phe Gln Ile Asn
                245                 250                 255
Ser Arg Tyr Trp Cys Asn Asp Gly Lys Thr Pro Gly Ala Val Asn Ala
                260                 265                 270
Cys His Leu Ser Cys Ser Ala Leu Leu Gln Asp Asn Ile Ala Asp Ala
            275                 280                 285
Val Ala Cys Ala Lys Arg Val Val Arg Asp Pro Gln Gly Ile Arg Ala
        290                 295                 300
Trp Val Ala Trp Arg Asn Arg Cys Gln Asn Arg Asp Val Arg Gln Tyr
305                 310                 315                 320
Val Gln Gly Cys Gly Val
                325

<210> SEQ ID NO 59
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Lys Val Phe Glu Arg Cys Glu Leu Ala Arg Thr Leu Lys Arg Leu Gly
1               5                   10                  15
Met Asp Gly Tyr Arg Gly Ile Ser Leu Ala Asn Trp Met Cys Leu Ala
                20                  25                  30
Lys Trp Glu Ser Gly Tyr Asn Thr Arg Ala Thr Asn Tyr Asn Ala Gly
            35                  40                  45
Asp Arg Ser Thr Asp Tyr Gly Ile Phe Gln Ile Asn Ser Arg Tyr Trp
        50                  55                  60
Cys Asn Asp Gly Lys Thr Pro Gly Ala Val Asn Ala Cys His Leu Ser
65                  70                  75                  80
Cys Ser Ala Leu Leu Gln Asp Asn Ile Ala Asp Ala Val Ala Cys Ala
                85                  90                  95
Lys Arg Val Val Arg Asp Pro Gln Gly Ile Arg Ala Trp Val Ala Trp
                100                 105                 110
```

```
Arg Asn Arg Cys Gln Asn Arg Asp Val Arg Gln Tyr Val Gln Gly Cys
            115                 120                 125

Gly Val Gly Gly Gly Ser Gly Gly Gly Ser Lys Ser Glu Leu
        130                 135                 140

Arg His Lys Leu Lys Tyr Val Pro His Glu Tyr Ile Glu Leu Ile Glu
145                 150                 155                 160

Ile Ala Arg Asn Ser Thr Gln Asp Arg Ile Leu Glu Met Lys Val Met
                165                 170                 175

Glu Phe Phe Met Lys Val Tyr Gly Tyr Arg Gly Lys His Leu Gly Gly
                180                 185                 190

Ser Arg Lys Pro Asp Gly Ala Ile Tyr Thr Val Gly Ser Pro Ile Asp
                195                 200                 205

Tyr Gly Val Ile Val Asp Thr Lys Ala Tyr Ser Gly Gly Tyr Asn Leu
        210                 215                 220

Pro Ile Gly Gln Ala Asp Glu Met Gln Arg Tyr Val Glu Glu Asn Gln
225                 230                 235                 240

Thr Arg Asn Lys His Ile Asn Pro Asn Glu Trp Trp Lys Val Tyr Pro
                245                 250                 255

Ser Ser Val Thr Glu Phe Lys Phe Leu Phe Val Ser Gly His Phe Lys
                260                 265                 270

Gly Asn Tyr Lys Ala Gln Leu Thr Arg Leu Asn His Ile Thr Asn Cys
        275                 280                 285

Asn Gly Ala Val Leu Ser Val Glu Glu Leu Leu Ile Gly Gly Glu Met
        290                 295                 300

Ile Lys Ala Gly Thr Leu Thr Leu Glu Glu Val Arg Arg Lys Phe Asn
305                 310                 315                 320

Asn Gly Glu Ile Asn Phe
                325

<210> SEQ ID NO 60
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125
```

```
Gly Val Gly Ser Lys Asp His Ile Leu Gln Phe Val Ile Pro Asn Arg
130                 135                 140

Leu Val Lys Ser Glu Leu Glu Glu Lys Ser Glu Leu Arg His Lys
145                 150                 155                 160

Leu Lys Tyr Val Pro His Glu Tyr Ile Glu Leu Ile Glu Ile Ala Arg
                165                 170                 175

Asn Ser Thr Gln Asp Arg Ile Leu Glu Met Lys Val Met Glu Phe Phe
                180                 185                 190

Met Lys Val Tyr Gly Tyr Arg Gly Lys His Leu Gly Gly Ser Arg Lys
                195                 200                 205

Pro Asp Gly Ala Ile Tyr Thr Val Gly Ser Pro Ile Asp Tyr Gly Val
210                 215                 220

Ile Val Asp Thr Lys Ala Tyr Ser Gly Gly Tyr Asn Leu Pro Ile Gly
225                 230                 235                 240

Gln Ala Asp Glu Met Gln Arg Tyr Val Glu Glu Asn Gln Thr Arg Asn
                245                 250                 255

Lys His Ile Asn Pro Asn Glu Trp Trp Lys Val Tyr Pro Ser Ser Val
                260                 265                 270

Thr Glu Phe Lys Phe Leu Phe Val Ser Gly His Phe Lys Gly Asn Tyr
                275                 280                 285

Lys Ala Gln Leu Thr Arg Leu Asn His Ile Thr Asn Cys Asn Gly Ala
290                 295                 300

Val Leu Ser Val Glu Glu Leu Leu Ile Gly Gly Glu Met Ile Lys Ala
305                 310                 315                 320

Gly Thr Leu Thr Leu Glu Glu Val Arg Arg Lys Phe Asn Asn Gly Glu
                325                 330                 335

Ile Asn Phe

<210> SEQ ID NO 61
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: Variation
<222> LOCATION: (2)..(30)
<223> OTHER INFORMATION: /replace=" "
<220> FEATURE:
<221> NAME/KEY: misc_feature
<222> LOCATION: (1)..(30)
<223> OTHER INFORMATION: /note="This sequence may encompass 1-30
      nucleotides"
<220> FEATURE:
<221> NAME/KEY: misc_feature
<222> LOCATION: (1)..(30)
<223> OTHER INFORMATION: /note="Variant nucleotides given in the
      sequence have no preference with respect to those in the
      annotations for variant positions"

<400> SEQUENCE: 61
tttttttttt tttttttttt tttttttttt                                   30

<210> SEQ ID NO 62
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 62 ttttt                                                                    5

<210> SEQ ID NO 63
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
tttttttttt                                                              10

<210> SEQ ID NO 64
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
tttttttttt tttttttttt t                                                 21

<210> SEQ ID NO 65
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: Variation
<222> LOCATION: (2)..(30)
<223> OTHER INFORMATION: /replace=" "
<220> FEATURE:
<221> NAME/KEY: misc_feature
<222> LOCATION: (1)..(30)
<223> OTHER INFORMATION: /note="This sequence may encompass 1-30
      nucleotides"
<220> FEATURE:
<221> NAME/KEY: misc_feature
<222> LOCATION: (1)..(30)
<223> OTHER INFORMATION: /note="Variant nucleotides given in the
      sequence have no preference with respect to those in the
      annotations for variant positions"

<400> SEQUENCE: 65
uuuuuuuuuu uuuuuuuuuu uuuuuuuuuu                                        30

<210> SEQ ID NO 66
<211> LENGTH: 5
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66 uuuuu                                                                    5

<210> SEQ ID NO 67
<211> LENGTH: 10
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
uuuuuuuuuu                                                               10

<210> SEQ ID NO 68
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
uuuuuuuuuu uuuuuuuuuu                                                    20

<210> SEQ ID NO 69
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
aaguucagcg uguccggcg                                                     19

<210> SEQ ID NO 70
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
ccguccagcu cgaccagga                                                     19

<210> SEQ ID NO 71
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ccggcaagcu gcccgugccc                                                    20

<210> SEQ ID NO 72
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 72
cagggucagc uugccguagg                                              20
```

RNA-GUIDED GENE EDITING SYSTEM AND USES THEREOF

RELATED APPLICATIONS

This application is a national stage entry under 35 U.S.C. section 371 of PCT application PCT/IB2016/052243, filed Apr. 20, 2016, and claims priority to U.S. Ser. No. 62/150,353, filed Apr. 21, 2015. The entire contents of each of these applications are incorporated herein by reference.

SEQUENCE LISTING

The instant application contains a Sequence Listing which has been submitted electronically in ASCII format and is hereby incorporated by reference in its entirety. Said ASCII copy, created on Apr. 18, 2016, is named PAT056693-WO-PCT_SL.txt and is 46,997 bytes in size.

BACKGROUND

Recently, gene editing systems such as zinc finger nucleases, CRISPR/Cas systems, transcription activator-like effector nucleases (TALENs) and meganucleases have emerged as tools for the regulation of genes.

Monomeric Cas9 nuclease-based systems are directed to cleave specific DNA sequences by an associated ~100-nt single RNA comprising 17-20 nucleotides that target the Cas9 nuclease to a site of interest (targeting RNA) by hybridizing to the target DNA site. While the simplicity of designing the targeting RNA to recognize predetermined sequences of DNA makes the CRISPR/Cas-based gene editing systems powerful, the large size of the Cas9 enzyme makes it nearly impossible to incorporate the system into a single vector for gene delivery in humans, and the sequence requirements of the Cas9 enzyme itself (e.g., PAM sequence) limit the sites to which it can be targeted.

In contrast, Zinc finger nuclease and TALEN-based gene editing system use much smaller enzyme components, such as the FokI nuclease, and the nucleases do not require specific binding sites. However, these systems are hampered by the use of protein-based DNA-targeting domains, which are difficult to engineer to bind specific DNA target sequences.

There is thus a need for a gene editing system which can be guided to a target DNA binding site using an easy-to-engineer component such as a targeting RNA but which utilizes a compact gene editing enzyme with no required sequence specificity.

SUMMARY

In a first aspect, the invention features a non-naturally occurring gene editing system including:
a) nucleic acid including a first targeting RNA capable of hybridizing with a target DNA sequence;
b) nucleic acid including a first guide RNA capable of binding to a first guide RNA-binding domain, and
c) a polypeptide including the first guide RNA-binding domain and a first cleavage domain,
wherein the polypeptide of c) includes fewer than approximately 1200 amino acids.

In a second aspect, the invention further features d) nucleic acid including a second targeting RNA capable of hybridizing with a second target DNA sequence, e) nucleic acid including a second guide RNA capable of binding to the first guide RNA-binding domain or a second guide-RNA-binding domain, and, optionally, f) a polypeptide including the second guide RNA-binding domain and a second cleavage domain, wherein the polypeptide of f) includes fewer than approximately 1200 amino acids.

In aspects featuring a polypeptide of c), the polypeptide of c) can include, for example, fewer than approximately 1100 amino acids, fewer than approximately 1000 amino acids, fewer than approximately 900 amino acids, fewer than approximately 800 amino acids, fewer than approximately 700 amino acids, fewer than approximately 600 amino acids, fewer than approximately 500 amino acids, fewer than approximately 400 amino acids, fewer than approximately 300 amino acids, or fewer than approximately 200 amino acids.

In some aspects, the invention features a non-naturally occurring gene editing system, wherein the nucleic acid of a) and the nucleic acid of b) are disposed on separate nucleic acid molecules. In aspects where the nucleic acid of a) and the nucleic acid of b) are disposed on separate nucleic acid molecules, the nucleic acid of a) may further include a hybridization domain A and the nucleic acid of b) may further include a hybridization domain A', wherein the hybridization domain A and hybridization domain A' are capable of specific hybridization. In one aspect, the hybridization domain A and the hybridization domain A' each include, for example, 10-50 complimentary nucleic acid residues, e.g., 20-40 complimentary nucleic acid residues, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 complimentary nucleic acid residues.

In some aspects, the non-naturally-occurring gene editing systems described above include, for example, a nucleic acid of a) and a nucleic acid of b) that are disposed on the same molecule. In some aspects the nucleic acid may further include, for example, additional nucleic acids disposed between the nucleic acid of a) and the nucleic acid of b).

In some aspects, the invention features a non-naturally occurring gene editing system, wherein the first guide RNA-binding domain is, for example, lysozyme, e.g., SEQ ID NO: 2, SEQ ID NO: 50, or an RNA binding fragment or analog thereof. In some aspects where the first guide RNA-binding domain is, for example, lysozyme, e.g., SEQ ID NO: 2, SEQ ID NO: 50, or an RNA binding fragment or analog thereof, the first guide RNA includes, for example, SEQ ID NO: 3.

In some aspects, the non-naturally occurring gene editing systems of the present invention include those in which the first guide RNA-binding domain is a fibronectin.

In some aspects, the non-naturally occurring gene editing systems of the present invention include those in which the first guide RNA-binding domain is an antibody or antigen-binding fragment or analog thereof. In some aspects, the antibody or antigen-binding fragment or analog thereof is, for example, an IgE-derived antibody or antigen-binding fragment or analog thereof. In embodiments where the antibody or antigen-binding fragment or analog thereof is, for example, an IgE-derived antibody or antigen-binding fragment or analog thereof, the first guide RNA includes, for example, SEQ ID NO: 11.

In some aspects, the non-naturally occurring gene editing systems of the present invention include those in which the first guide RNA-binding domain includes a sequence of an IgG1 Fc domain, or guide RNA-binding fragment or analog thereof. In embodiments, the first guide RNA-binding domain includes SEQ ID NO: 40, or a guide RNA-binding fragment or analog thereof. In embodiments in which the first guide RNA-binding domain includes SEQ ID NO: 40 or a guide RNA-binding fragment or analog thereof, the first guide RNA includes, for example, SEQ ID NO: 41, or fragment or analog thereof.

In some aspects, the non-naturally occurring gene editing systems of the present invention include those in which the first guide RNA-binding domain includes a polyhistidine sequence, for example, a sequence of a histidine tag, or guide RNA-binding fragment or analog thereof. In embodiments, the first guide RNA-binding domain includes SEQ ID NO: 7, SEQ ID NO: 51, SEQ ID NO: 52, SEQ ID NO: 53, or a guide RNA-binding fragment or analog of any of said sequences. In embodiments in which the first guide RNA-binding domain includes SEQ ID NO: 7, SEQ ID NO: 51, SEQ ID NO: 52, SEQ ID NO: 53 or a guide RNA-binding fragment or analog of any of said sequences, the first guide RNA includes, for example, SEQ ID NO: 8, or fragment or analog thereof.

In some aspects, the non-naturally occurring gene editing systems of the present invention include those in which the first guide RNA-binding domain includes a streptavidin sequence, or guide RNA-binding fragment or analog thereof. In embodiments, the first guide RNA-binding domain includes SEQ ID NO: 9, or a guide RNA-binding fragment or analog thereof. In embodiments in which the first guide RNA-binding domain includes SEQ ID NO: 9 or a guide RNA-binding fragment or analog thereof, the first guide RNA includes, for example, SEQ ID NO: 39, or fragment or analog thereof.

In some aspects, the non-naturally occurring gene editing systems of the present invention include those in which the first guide RNA-binding domain is a fluorescent protein or functional fragment thereof, for example, is selected from proteins identified in Tables 1-4, or an RNA-binding fragment or analog of any proteins identified in Tables 1-4. In some embodiments, the first guide RNA-binding domain is green fluorescent protein (e.g., UniProt code P42212), or an RNA-binding fragment or analog thereof. In embodiments where the first guide RNA-binding domain is a fluorescent protein or functional fragment thereof, the first guide RNA can include, for example, SEQ ID NO: 10.

In some aspects, the invention features a non-naturally occurring gene editing system, wherein the first cleavage domain includes a functional fragment of a nuclease capable of inducing a double-strand break in DNA, for example, a functional fragment of a GIY-YIG homing endonuclease, e.g., a functional fragment of I-TevI, e.g., SEQ ID NO: 13 or a functional fragment of SEQ ID NO: 13. In some embodiments, the first cleavage domain includes a polypeptide derived from a Type IIS restriction enzyme. In some aspects, the first cleavage domain includes a polypeptide capable of inducing a single strand break in DNA, e.g., includes a functional fragment of a nuclease selected from the group including of FokI and PvuII, e.g., SEQ ID NO: 12, SEQ ID NO: 49, or a functional fragment of SEQ ID NO: 12 or SEQ ID NO: 49.

In aspects featuring a polypeptide of f), the polypeptide of f) may include, for example, fewer than approximately 1100 amino acids, fewer than approximately 1000 amino acids, fewer than approximately 900 amino acids, fewer than approximately 800 amino acids, fewer than approximately 700 amino acids, fewer than approximately 600 amino acids, fewer than approximately 500 amino acids, fewer than approximately 400 amino acids, fewer than approximately 300 amino acids, or fewer than approximately 200 amino acids.

In aspects featuring the nucleic acid of d) and the nucleic acid of e), these may be disposed, for example on separate nucleic acid molecules. In such embodiments, the nucleic acid of d) may further include, for example, a hybridization domain B and the nucleic acid of e) may further include, for example, a hybridization domain B', wherein the hybridization domain B and hybridization domain B' are capable of specific hybridization. In some embodiments, the hybridization domain B and the hybridization domain B' each include, for example, 10-50 complimentary nucleic acid residues, e.g., 20-40, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleic acid residues.

In some aspects featuring the nucleic acid of d) and the nucleic acid of e), the nucleic acid of d) and the nucleic acid of e) may be disposed on the same molecule.

In some aspects of the invention featuring a second guide RNA-binding domain, the second guide RNA-binding domain is, for example, lysozyme, e.g., SEQ ID NO: 2, SEQ ID NO: 50, or an RNA binding fragment or analog thereof. In embodiments where the second guide RNA-binding domain is, for example, lysozyme, e.g., SEQ ID NO: 2, SEQ ID NO: 50, or an RNA binding fragment or analog thereof, the second guide RNA includes, for example, SEQ ID NO: 3.

In some aspects of the invention featuring a second guide RNA-binding domain, the non-naturally occurring gene editing systems of the present invention include those in which the second guide RNA-binding domain is a fibronectin.

In some aspects of the invention featuring a second guide RNA-binding domain, the non-naturally occurring gene editing systems of the present invention include those in which the second guide RNA-binding domain is an antibody or antigen-binding fragment or analog thereof. In some aspects, the antibody or antigen-binding fragment or analog thereof is, for example, an IgE-derived antibody or antigen-binding fragment or analog thereof. In embodiments where the antibody or antigen-binding fragment or analog thereof is, for example, an IgE-derived antibody or antigen-binding fragment or analog thereof, the second guide RNA includes, for example, SEQ ID NO: 11.

In some aspects of the invention featuring a second guide RNA-binding domain, the non-naturally occurring gene editing systems of the present invention include those in which the second guide RNA-binding domain includes a sequence of an IgG1 Fc domain, or guide RNA-binding fragment or analog thereof. In embodiments, the second guide RNA-binding domain includes SEQ ID NO: 40, or a guide RNA-binding fragment or analog thereof. In embodiments in which the second guide RNA-binding domain includes SEQ ID NO: 40 or a guide RNA-binding fragment or analog thereof, the second guide RNA includes, for example, SEQ ID NO: 41, or fragment or analog thereof.

In some aspects of the invention featuring a second guide RNA-binding domain, the non-naturally occurring gene editing systems of the present invention include those in which the second guide RNA-binding domain includes a polyhistidine sequence, for example, a sequence of a histidine tag, or guide RNA-binding fragment or analog thereof. In embodiments, the second guide RNA-binding domain includes SEQ ID NO: 7, SEQ ID NO: 51, SEQ ID NO: 52, SEQ ID NO: 53, or a guide RNA-binding fragment or analog thereof. In embodiments in which the second guide RNA-binding domain includes SEQ ID NO: 7, SEQ ID NO: 51, SEQ ID NO: 52, SEQ ID NO: 53, or a guide RNA-binding fragment or analog thereof, the second guide RNA includes, for example, SEQ ID NO: 8, or fragment or analog thereof.

In some aspects of the invention featuring a second guide RNA-binding domain, the non-naturally occurring gene editing systems of the present invention include those in which the second guide RNA-binding domain includes a streptavidin sequence, or guide RNA-binding fragment or analog thereof. In embodiments, the second guide RNA-binding domain includes SEQ ID NO: 9, or a guide RNA-binding fragment or analog thereof. In embodiments in which the second guide RNA-binding domain includes SEQ ID NO: 9 or a guide RNA-binding fragment or analog thereof, the second guide RNA includes, for example, SEQ ID NO: 39, or fragment or analog thereof.

In some aspects of the invention featuring a second guide RNA-binding domain, the non-naturally occurring gene editing systems of the present invention include those in which the second guide RNA-binding domain is a fluorescent protein or functional fragment thereof, for example, is selected from proteins identified in Tables 1-4, or an RNA-binding fragment or analog of any proteins identified in Tables 1-4. In some embodiments, the second guide RNA-binding domain is green fluorescent protein (e.g., UniProt code P42212), or an RNA-binding fragment or analog thereof. In embodiments where the second guide RNA-binding domain is a fluorescent protein or functional fragment thereof, the second guide RNA can include, for example, SEQ ID NO: 10.

In some aspects of the invention featuring a first guide RNA and a second guide RNA, the first guide RNA and the second guide RNA include different sequences. In some aspects the first guide RNA and the second guide RNA include the same sequence.

In some aspects, the non-naturally occurring gene editing systems that include a first guide RNA and a second guide RNA, the first guide RNA and second guide RNA may each independently bind to the first guide RNA-binding domain, e.g., a first guide RNA-binding domain described herein.

In some aspects featuring a first guide RNA and a second guide RNA, the first guide RNA and second guide RNA may each include, for example SEQ ID NO: 3. In such aspects, the first guide RNA-binding domain includes, e.g., lysozyme or a guide RNA binding fragment or analog thereof, e.g., SEQ ID NO: 2, SEQ ID NO: 50 or a guide RNA binding fragment or analog thereof.

In some aspects featuring a first guide RNA and a second guide RNA, the first and second guide RNA may each include, for example SEQ ID NO: 11. In such aspects, the first guide RNA-binding domain may include, for example, an IgE antibody or an antigen binding fragment or analog thereof.

In some aspects of the invention featuring a first guide RNA and a second guide RNA-binding domain, the first and second guide RNA may each include, for example SEQ ID NO: 41, or fragment or analog thereof. In such aspects, the first guide RNA-binding domain may include, for example, a sequence of an IgG1 Fc domain, or guide RNA-binding fragment or analog thereof, e.g., SEQ ID NO: 40, or a guide RNA-binding fragment or analog thereof.

In some aspects of the invention featuring a first guide RNA and a second guide RNA-binding domain, the first and second guide RNA may each include, for example, SEQ ID NO: 8, or fragment or analog thereof. In such aspects, the first guide RNA-binding domain may include, for example, a sequence including a polyhistidine sequence, or guide RNA-binding fragment or analog thereof, e.g., SEQ ID NO: 7, SEQ ID NO: 51, SEQ ID NO: 52, SEQ ID NO: 53, or a guide RNA-binding fragment or analog thereof.

In some aspects of the invention featuring a first guide RNA and a second guide RNA-binding domain, the first and second guide RNA may each include, for example, SEQ ID NO: 39, or fragment or analog thereof. In such aspects, the first guide RNA-binding domain may include, for example, a streptavidin sequence, or guide RNA-binding fragment or analog thereof, e.g., SEQ ID NO: 9, or a guide RNA-binding fragment or analog thereof.

In some aspects featuring a first guide RNA and a second guide RNA, the first and second guide RNA each include SEQ ID NO: 10. In such aspects, the first guide RNA-binding domain includes, for example, a fluorescent protein or an active fragment thereof, e.g., is selected from the proteins identified in Tables 1-4, and an RNA-binding fragment or analog of any of the preceding.

In some aspects featuring a first guide RNA and a second guide RNA, the invention features a non-naturally occurring gene editing system, wherein the first guide RNA binds specifically to the first guide RNA-binding domain and the second guide RNA binds specifically to the second guide RNA-binding domain. For example, the first guide RNA does not bind the second guide RNA-binding domain and the second guide RNA does not bind the first guide RNA-binding domain. In some aspects, the first guide RNA-binding domain and the second guide RNA-binding domain are independently selected from the group including: lysozyme, a fibronectin, an antibody or antigen-binding fragment or analog thereof, and a fluorescent protein or functional fragment or analog thereof, with the proviso that the first guide RNA-binding domain and the second guide RNA-binding domain are not identical.

In another aspect, the invention features a non-naturally occurring gene editing system including: a) nucleic acid including a first targeting RNA capable of hybridizing with a target DNA sequence, b) nucleic acid including a first guide RNA capable of binding directly to a first cleavage domain, and c) a polypeptide including the first cleavage domain, wherein the polypeptide of c) includes fewer than approximately 1200 amino acids, for example, fewer than approximately 1100 amino acids, fewer than approximately 1000 amino acids, fewer than approximately 900 amino acids, fewer than approximately 800 amino acids, fewer than approximately 700 amino acids, fewer than approximately 600 amino acids, fewer than approximately 500 amino acids, fewer than approximately 400 amino acids, fewer than approximately 300 amino acids, or fewer than approximately 200 amino acids.

In some embodiments that include a first guide RNA capable of binding directly to a first cleavage domain, the nucleic acid of a) and the nucleic acid of b) are disposed on the same molecule. In some aspects, the invention features a non-naturally occurring gene editing system, wherein the nucleic acid of a) and the nucleic acid of b) are disposed on separate nucleic acid molecules. In aspects where the nucleic acid of a) and the nucleic acid of b) are disposed on separate nucleic acid molecules, the nucleic acid of a) may further include a hybridization domain A and the nucleic acid of b) may further include a hybridization domain A', wherein the hybridization domain A and hybridization domain A' are capable of specific hybridization. In one aspect, the hybridization domain A and the hybridization domain A' each include, for example, 10-50 complimentary nucleic acid residues, e.g., 20-40, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleic acid residues.

In some aspects of the invention that include a first guide RNA capable of binding directly to a first cleavage domain, the invention may further include d) nucleic acid including a second targeting RNA capable of hybridizing with a target DNA sequence, e) nucleic acid including a second guide RNA capable of binding directly to the first or a second cleavage domain, and, optionally, f) a polypeptide including the second cleavage domain, wherein the polypeptide of f) includes fewer than approximately 1200 amino acids, for example, fewer than approximately 1100 amino acids, fewer than approximately 1000 amino acids, fewer than approximately 900 amino acids, fewer than approximately 800 amino acids, fewer than approximately 700 amino acids, fewer than approximately 600 amino acids, fewer than approximately 500 amino acids, fewer than approximately 400 amino acids, fewer than approximately 300 amino acids, or fewer than approximately 200 amino acids.

In some aspects of the invention that include a first guide RNA capable of binding directly to a first cleavage domain and featuring the nucleic acid of d) and the nucleic acid of e), the nucleic acid of d) and the nucleic acid of e) may be disposed, for example, on the same nucleic acid molecule. In other embodiments, the nucleic acid of d) and the nucleic acid of e), these may be disposed, for example, on separate nucleic acid molecules. In such embodiments, the nucleic acid of d) may further include, for example, a hybridization domain B and the nucleic acid of e) may further include, for example, a hybridization domain B', wherein the hybridization domain B and hybridization domain B' are capable of specific hybridization. In some embodiments, the hybridization domain B and the hybridization domain B' each include, for example, 10-50 complimentary nucleic acid residues, e.g., 20-40, e.g., 20, 21, 22, 23, 24, 25, 26, 27, 28, 29, 30, 31, 32, 33, 34, 35, 36, 37, 38, 39 or 40 nucleic acid residues.

In one aspect, one or more of the polypeptide-based components the non-naturally occurring gene editing systems of the present invention further include a nuclear localization sequence (NLS).

In another aspect, the present invention features a chimeric polypeptide including a RNA-binding domain and a cleavage domain that are not naturally associated, wherein the chimeric polypeptide includes fewer than approximately 1200 amino acids, for example, fewer than approximately 1100 amino acids, fewer than approximately 1000 amino acids, fewer than approximately 900 amino acids, fewer than approximately 800 amino acids, fewer than approximately 700 amino acids, fewer than approximately 600 amino acids, fewer than approximately 500 amino acids, fewer than approximately 400 amino acids, fewer than approximately 300 amino acids, or fewer than approximately 200 amino acids.

In some embodiments, the chimeric polypeptide features an RNA binding domain that includes lysozyme or an RNA-binding fragment or analog thereof, e.g., is SEQ ID NO: 2, SEQ ID NO: 50, or an RNA-binding fragment or analog thereof.

In some embodiments, the chimeric polypeptide features an RNA-binding domain that includes a fibronectin.

In some embodiments, the chimeric polypeptide features an RNA-binding domain that includes an antibody or guide RNA-binding fragment or analog thereof, e.g., an IgE antibody or RNA-binding fragment thereof.

In some embodiments, the chimeric polypeptide features an RNA-binding domain that includes an IgG1 Fc or guide RNA-binding fragment or analog thereof, e.g., SEQ ID NO: 40, or guide RNA-binding fragment or analog thereof.

In some embodiments, the chimeric polypeptide features an RNA-binding domain that includes streptavidin or guide RNA-binding fragment or analog thereof, e.g., SEQ ID NO: 9, or guide RNA-binding fragment or analog thereof.

In some embodiments, the chimeric polypeptide features an RNA-binding domain that includes polyhistidine sequence, e.g., a histidine tag, or guide RNA-binding fragment or analog thereof, e.g., SEQ ID NO: 7, SEQ ID NO: 51, SEQ ID NO: 52, SEQ ID NO: 53, or guide RNA-binding fragment or analog thereof.

In some embodiments, the chimeric polypeptide features an RNA-binding domain that includes fluorescent protein or functional fragment or analog thereof. In some embodiments the florescent protein or functional fragment or analog thereof is selected from the group including of the proteins identified in Tables 1-4, and an RNA-binding fragment or analog of any of the proteins identified in Tables 1-4.

In embodiments of the foregoing chimeric polypeptides, the cleavage domain includes a functional fragment of a nuclease capable of inducing a double-strand break in DNA. For example, the cleavage domain can include a a GIY-YIG homing endonuclease or a functional fragment of a GIY-YIG homing endonuclease, for example, I-TevI or a functional fragment of I-TevI, e.g., SEQ ID NO: 13.

In embodiments of the foregoing chimeric polypeptides, the first cleavage domain includes a functional fragment of a nuclease capable of inducing a single-strand break in DNA. For example, the first cleavage domain includes Fok I or PvuII, or a functional fragment of FokI or PvuII, e.g., SEQ ID NO: 12 or SEQ ID NO: 49.

In another aspect of the invention, any of the foregoing chimeric polypeptides further include a NLS, e.g., an NLS selected from the group including SEQ ID NOS: 22-37.

In one aspect, the invention features a nucleic acid, e.g., an isolated nucleic acid, including sequence encoding any of the foregoing gene editing systems or any of the foregoing chimeric polypeptides.

In one aspect, the invention features a vector including any of the foregoing nucleic acids.

In some aspects, the vector is selected from the group including of a viral vector, a plasmid, a minicircle, and a nanoplasmid. In one embodiment the vector is a viral vector. For example, the viral vector is selected from the group including of a lentivirus vector, adenovirus vector, adeno-associated vector and a retrovirus vector.

In embodiments, the vector includes fewer than 10,000 nucleic acid residues, for example, fewer than 9000 nucleic acid residues, fewer than 8000 nucleic acid residues, fewer than 7000 nucleic acid residues, fewer than 6000 nucleic acid residues, fewer than 5000 nucleic acid residues, fewer than 4000 nucleic acid residues, or fewer than 3000 nucleic acid residues.

In an aspect, the invention features a cell that includes any of the foregoing gene editing systems, any of the foregoing chimeric polypeptides, any of the foregoing nucleic acids, or any of the foregoing vectors. In embodiments the cell is a human cell, e.g., a human stem or progenitor cell, e.g., a hematopoietic stem cell (HSC). In embodiments the cell is a T cell, e.g., a human T cell. In embodiments the cell is a NK cell, e.g., a human NK cell. In embodiments the cell is a cancer cell, e.g., a human cancer cell.

In one aspect the invention features a cell derived from any of the forgoing cells, e.g., a daughter or progeny cell of any of the foregoing cells.

In one aspect, the invention features a method of making a cell, e.g., any of the foregoing cells, including introducing into the cell a) a gene editing system of the present invention, e.g., as described herein; b) a chimeric polypeptide of the present invention, e.g., as described herein; c) a nucleic acid of the present invention, e.g., as described herein; or d) a vector of the present invention, e.g., as described herein. In one aspect, the method is performed in vitro. In one aspect, the method is performed ex vivo. In one aspect the method is performed in vivo.

In one aspect the invention features a method of modulating expression of a gene in a cell including introducing into the cell a) a gene editing system of the present invention, e.g., as described herein; b) a chimeric polypeptide of the present invention, e.g., as described herein; c) a nucleic acid of the present invention, e.g., as described herein; or d) a vector of the present invention, e.g., as described herein, such that expression of a gene in a cell is modulated. In one aspect, the method is performed in vitro. In one aspect, the method is performed ex vivo. In one aspect the method is performed in vivo. In one aspect the method of modulation results in repression of a gene in a cell, e.g., reduced expression in a cell. In one aspect the method of modulation results in activation of a gene in a cell, e.g., increased expression in a cell.

In one aspect, the invention features a method of modifying an endogenous nucleic acid sequence, e.g., a gene, in a cell, including administering to the cell a) a gene editing system of the present invention, e.g., as described herein; b) a chimeric polypeptide of the present invention, e.g., as described herein; c) a nucleic acid of the present invention, e.g., as described herein; or d) a vector of the present invention, e.g., as described herein, such that an endogenous nucleic acid sequence, e.g., a gene, in a cell is modified. In some aspects the method of modifying includes deletion of one or more endogenous nucleic acid residues. In some aspects the method of modifying includes the replacement of one or more endogenous nucleic acid residues with nucleic acids from a donor nucleic acid molecule. In one aspect, the method is performed in vitro. In one aspect, the method is performed ex vivo. In one aspect the method is performed in vivo.

In one aspect, the invention features a cell, wherein expression of one or more endogenous genes has been modulated by the method of any of the foregoing methods of modulation of expression of a gene in a cell.

In one aspect, the invention features a cell, wherein one or more endogenous nucleic acid sequences, e.g., genes, have been modified by the method of any of the foregoing methods of modifying an endogenous nucleic acid sequence, e.g., a gene, in a cell.

In some embodiments, the gene that is modified or modulated includes an HLA gene. In some embodiments, the gene that is modified or modulated includes a beta 2-microglobulin (B2M) gene. In some embodiments, the gene that is modified or modulated includes a TCR gene, e.g., TCRα or TCRβ. In some embodiments, the gene that is modified or modulated includes an inhibitory molecule selected from the group including of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. In embodiments combinations, e.g., two or more, genes are modified and/or modulated in the same cell, resulting in a cell in which combinations, e.g., two or more have been modified and/or modulated. In one embodiment, the invention features a cell in which both HLA and a TCR gene, e.g., TCRα or TCRβ, have been modified and/or modulated In one aspect, the invention features a cell derived from the cell of any of the foregoing, e.g. a daughter cell or progeny cell.

In one aspect, the invention features a method of treating a subject, e.g., a mammal, having a disease associated with aberrant gene expression, e.g., a disease described herein, including administering to the subject an effective amount of a) a gene editing system of the present invention, e.g., any of the foregoing; b) a chimeric polypeptide of the present invention, e.g., any of the foregoing; c) a nucleic acid of the present invention, e.g., any of the foregoing; d) a vector of the present invention, e.g., any of the foregoing; or e) a cell of the present invention, e.g., any of the foregoing.

In one aspect, the invention features a) a gene editing system of the present invention, e.g., any of the foregoing; b) a chimeric polypeptide of the present invention, e.g., any of the foregoing; c) a nucleic acid of the present invention, e.g., any of the foregoing; d) a vector of the present invention, e.g., any of the foregoing; or e) a cell of the present invention, e.g., any of the foregoing, for use as a medicament.

In one aspect, the invention features a) a gene editing system of the present invention, e.g., any of the foregoing; b) a chimeric polypeptide of the present invention, e.g., any of the foregoing; c) a nucleic acid of the present invention, e.g., any of the foregoing; d) a vector of the present invention, e.g., any of the foregoing; or e) a cell of the present invention, e.g., any of the foregoing, for use in treating a disease associated with aberrant gene expression.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

DESCRIPTION

Definitions

Figure 1:
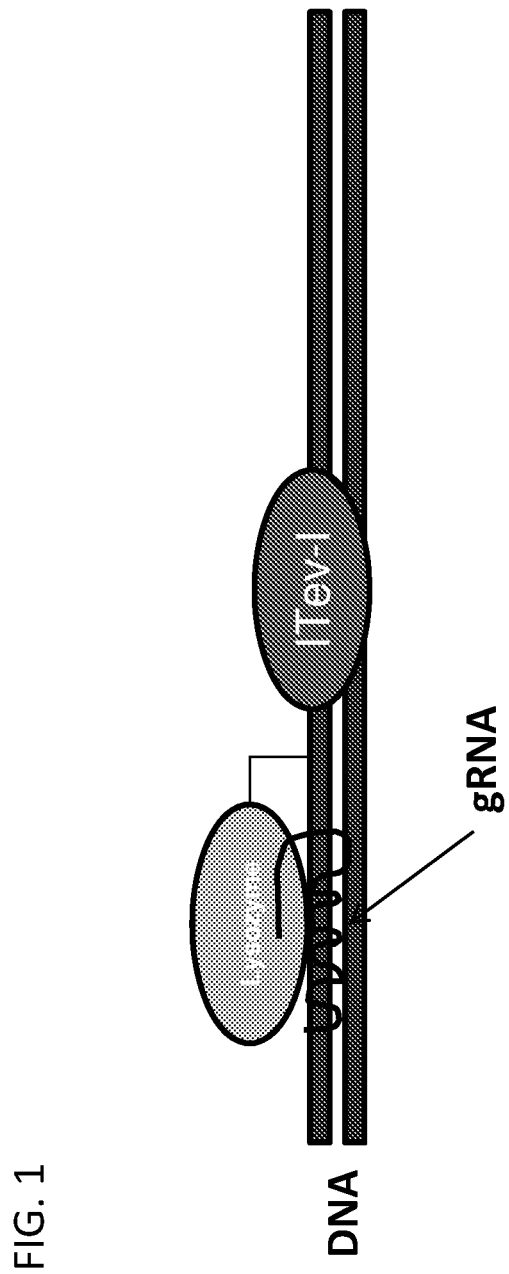
FIG. 1 is a graphical representation of a monomeric gene editing system of the present invention. In this example, the guide RNA-binding domain is lysozyme and the cleavage domain is derived from the ITev-I nuclease. In this figure, "gRNA" represents a chimeric fusion between a targeting RNA and a guide RNA (e.g., SEQ ID NO: 3 when the guide RNA-binding domain is lysozyme or a guide RNA-binding fragment thereof).
Figure 2:
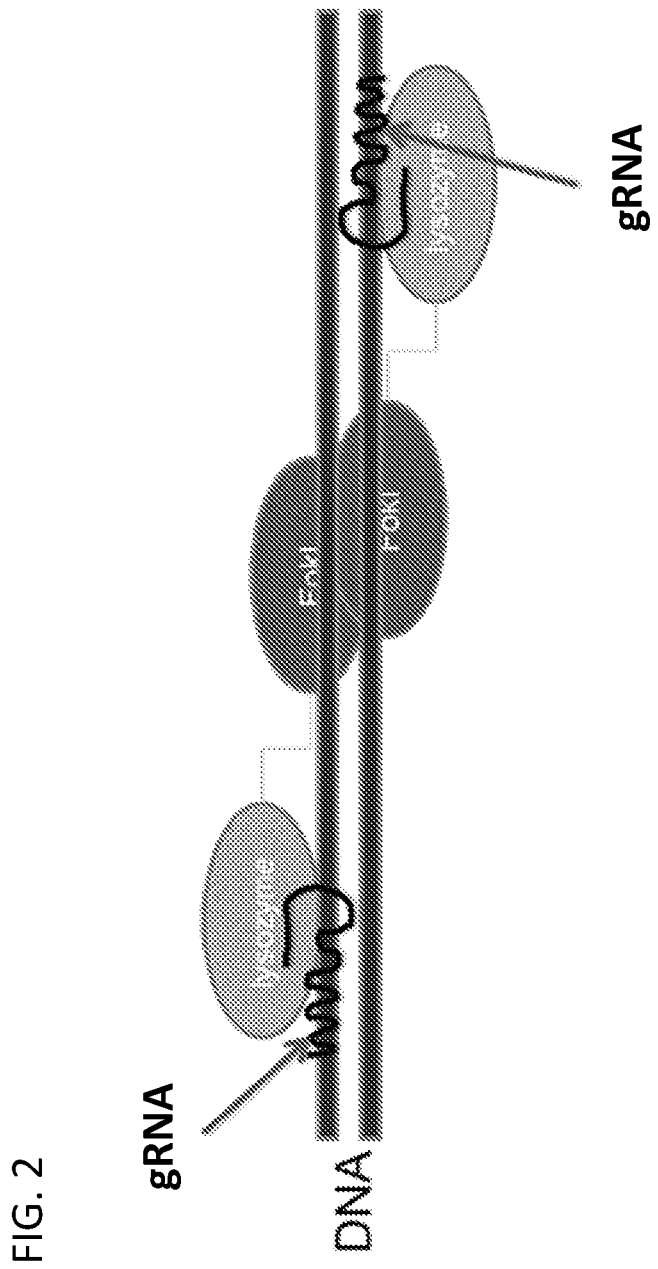
FIG. 2 is a graphical representation of a dimeric gene editing system of the present invention. In this example, the guide RNA-binding domain is lysozyme and the cleavage domain is a FokI domain. In this figure, "gRNA" represents a chimeric fusion between a targeting RNA and a guide RNA (e.g., SEQ ID NO: 3 when the guide RNA-binding domain is lysozyme or a guide RNA-binding fragment thereof).
Figure 3:
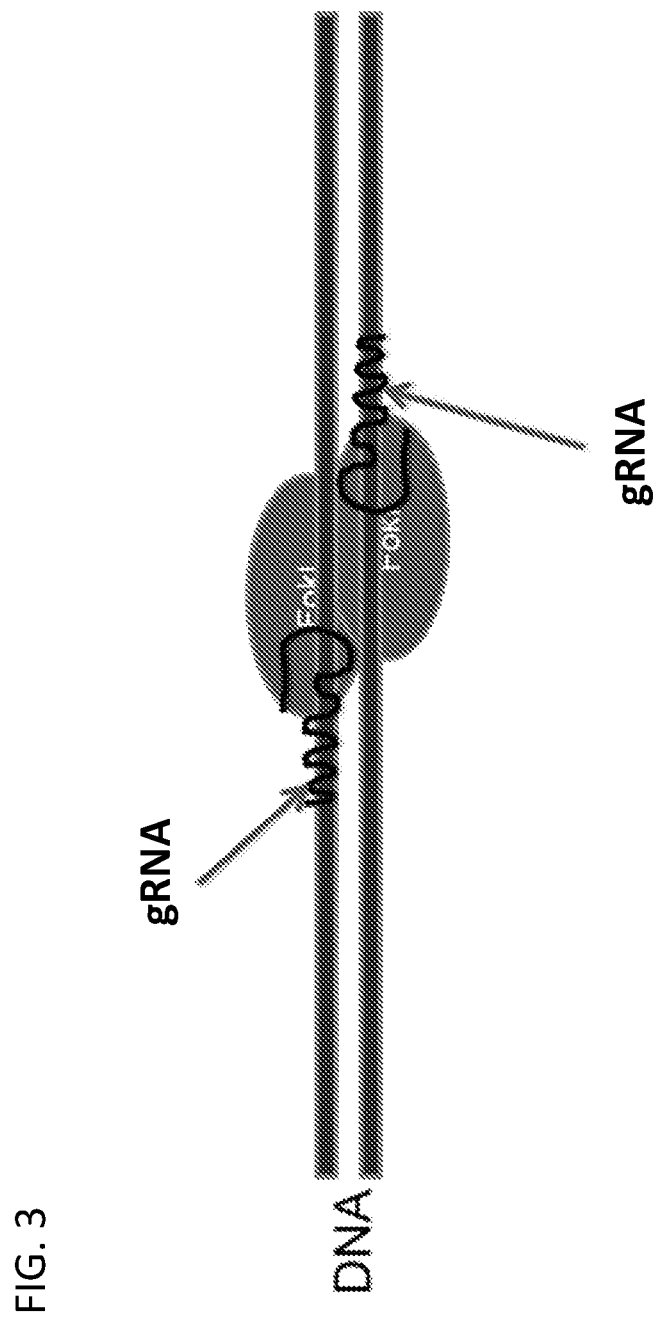
FIG. 3 is a graphical representation of a dimeric gene editing system of the present invention. In this example, the guide RNA binds directly to the Fok-I nuclease domain. In this figure, "gRNA" represents a chimeric fusion between a targeting RNA and a guide RNA.

Unless defined otherwise, all technical and scientific terms used herein have the same meaning as commonly understood by one of ordinary skill in the art to which the invention pertains.

"A" and "an" as used herein, refers to one or to more than one (i.e., to at least one) of the grammatical object of the article. By way of example, "an element" means one element or more than one element.

The term "approximately" as used herein, when referring to a measurable value such as an amount, a temporal duration, and the like, is meant to encompass variations of ±20% or in some aspects ±10%, or in some aspects ±5%, or in some aspects ±1%, or in some aspects ±0.1% from the specified value, as such variations are appropriate to perform the disclosed methods.

The term "amino acid" as used herein, refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" as used herein, applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," as used herein in the context of two or more nucleic acids or polypeptide sequences, refers to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "amino acid" as used herein, refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" as used herein, applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," as used herein in the context of two or more nucleic acids or polypeptide sequences, refers to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "modulate" or "modulating" as used herein in connection with gene expression refers to altering of the level of expression of the gene relative to any baseline level of expression. Modulating gene expression can include, for example, repression of expression or upregulation of expression. Modulation can be mediated, for example, at the transcription level, the translation level, or at the post-translation level. Levels of expression of a gene can be quantified to determine if expression has been modulated by any quantitative method known in the art, e.g., quantitative PCR or quantitative binding assay.

The terms "modify" or "modifying" as used herein in connection with an endogenous nucleic acid sequence refers to the chemical alteration of the target nucleic acid sequence. In one aspect, the modifying comprises breaking a covalent bond present in the target nucleic acid sequence, e.g., a covalent bond of the target nucleic acid phosphodiester backbone. In one aspect, the modifying comprises the removal or excision of one or more base pairs from the target nucleic acid sequence. In one aspect, the modifying comprises the addition of one or more base pairs to the target nucleic acid sequence. The modifying may occur in one step or in more than one step.

The term "antibody" as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment or analog" refers to at least one portion of an intact antibody, or recombinant variants thereof, and refers to an antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), camelid VHH domains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of the gene editing system or chimeric polypeptide invention comprising an antibody or antibody fragment thereof may exist in a variety of forms where the antigen binding domain is expressed as part of a contiguous polypeptide chain including, for example, a single domain antibody fragment (sdAb), a single chain antibody (scFv) a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antibody- or antibody fragment or analog thereof-containing portion of the gene editing system or chimeric polypeptide composition of the invention comprises an antibody fragment. In a further aspect, the antibody- or antibody fragment or analog thereof-containing portion of the gene editing system or chimeric polypeptide composition of the invention comprises a scFv. In a further aspect, the antibody- or antibody fragment or analog thereof-containing portion of the gene editing system or chimeric polypeptide composition of the invention comprises a single domain antibody fragment such as a VL or VH domain.

The term "antibody heavy chain" refers to the larger of the two types of polypeptide chains present in antibody molecules in their naturally occurring conformations, and which normally determines the class to which the antibody belongs.

The term "antibody light chain" refers to the smaller of the two types of polypeptide chains present in antibody molecules in their naturally occurring conformations. Kappa (□) and lambda (□) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA or RNA. A skilled artisan will understand that any DNA or RNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

An antigen also includes a molecule specifically recognized by an antibody or antigen-binding fragment or analog thereof. In one aspect of the invention, the antigen is an RNA molecule.

The term "anti-tumor effect" refers to a biological effect which can be manifested by various means, including but not limited to, e.g., a decrease in tumor volume, a decrease in the number of cancer cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "cancer" refers to a disease characterized by the uncontrolled growth of aberrant cells. Cancer cells can spread locally or through the bloodstream and lymphatic system to other parts of the body. Examples of various cancers are described herein and include, but are not limited to, mesothelioma, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Likewise, a gene, cDNA or RNA encodes an RNA if transcription of DNA or RNA complimentary to that RNA produces the RNA in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "expression" refers to the transcription and/or translation of a particular nucleotide sequence driven by its promoter.

The term "effective amount" or "therapeutically effective amount" is used interchangeably herein, and refer to an amount of a compound, formulation, material, or composition, as described herein effective to achieve a particular biological result. The term "endogenous" refers to any material from or produced inside an organism, cell, tissue or system.

The term "exogenous" refers to any material introduced from or produced outside an organism, cell, tissue or system.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, where necessary to join two protein coding regions, are in the same reading frame.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "polypeptide linker" refers to a peptide linker that consists of amino acids such as glycine and/or serine residues used alone or in combination, to link, for example, one domain to another domain. In one embodiment, the flexible polypeptide linker is a Gly/Ser linker and comprises the amino acid sequence (Gly-Gly-Gly-Ser)$_n$(SEQ ID NO: 38), where n is a positive integer equal to or greater than 1. For example, n=1, n=2, n=3, n=4, n=5 and n=6, n=7, n=8, n=9 and n=10. In one embodiment, the flexible polypeptide linkers include, but are not limited to, (Gly$_4$ Ser)$_4$ (SEQ ID NO: 42) or (Gly$_4$ Ser)$_3$ (SEQ ID NO: 43) In another embodiment, the linkers include multiple repeats of (Gly$_2$Ser), (GlySer) or (Gly$_3$Ser) (SEQ ID NO: 44). Also included within the scope of the invention are linkers described in WO2012/138475, incorporated herein by reference).

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "subject" is intended to include living organisms in which an immune response can be elicited (e.g., mammals, human).

The term "therapeutic" as used herein means a treatment. A therapeutic effect is obtained by reduction, suppression, remission, or eradication of a disease state.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant (Kd) of 10-6 M−1 or lower. "Affinity" refers to the strength of binding: increased binding affinity being correlated with a lower Kd.

The term "specifically binds," refers to an antibody, polypeptide, nucleic acid or a ligand, which recognizes and binds with a cognate binding partner (e.g., an RNA aptamer)

present in a sample, but which antibody, polypeptide, nucleic acid or ligand does not substantially recognize or bind other molecules in the sample.

"Cleavage" refers to the breakage of a covalent bond, e.g., of a covalent bond on the backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, the genome editing systems of the present invention are used for targeted double-stranded DNA cleavage. In certain embodiments, the genome editing systems of the present invention are used for targeted single-stranded DNA cleavage.

A "cleavage domain" refers to a polypeptide having the ability, either alone or in conjunction with another cleavage domain (e.g., a cleavage half-domain), to cleave a DNA molecule. Thus, it is understood that a "cleavage domain" as the term is used herein, includes cleavage half-domains.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize. The term cleavage half-domain includes engineered cleavage half-domains.

An "engineered cleavage half-domain" is a cleavage half-domain that has been modified so as to form obligate heterodimers with another cleavage half-domain (e.g., another engineered cleavage half-domain). Non-limiting examples of engineered cleavage half-domains are described in U.S. Patent Publication Nos. 2005/0064474; 2007/0218528 and 2008/0131962, incorporated herein by reference in their entireties.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a guide RNA-binding domain and a cleavage domain) and fusion nucleic acids (for example, a single nucleic acid comprising a targeting RNA and a guide RNA). Examples of the second type of fusion molecule include, but are not limited to, a fusion between a nucleic acid (e.g., an RNA) and a polypeptide, or a fusion between a small molecule and a nucleic acid or polypeptide.

Expression of a fusion protein in a cell can result from delivery of the fusion protein to the cell or by delivery of a polynucleotide encoding the fusion protein to a cell, wherein the polynucleotide is transcribed; and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure. Fusion molecules may be referred to as "chimeric" if their subunit molecules are not normally associated with each other (i.e., are derived from different source molecules).

A "gene editing system" as the term is used refers to a system that is capable of inducing a change to a nucleic acid sequence, e.g., a chromosome, e.g., a gene, e.g., a mammalian gene. In one embodiment a gene editing system comprises a nuclease component, e.g., a cleavage domain, and a targeting component, e.g., a targeting RNA component. In embodiments, the gene editing system further comprises one or more components that allow the targeting component to associate with one or more nuclease components. For example, the targeting RNA component may further comprise a guide RNA component, while the nuclease component may further comprise a guide RNA-binding component capable of binding specifically to the guide RNA. Additional embodiments and features of the gene editing systems of the present invention are further described herein.

A "targeting RNA" is a polyribonucleic acid capable of specifically recognizing a predetermined nucleic acid sequence. For example, the predetermined nucleic acid sequence can be a DNA sequence, e.g., a target DNA sequence. In embodiments, the predetermined nucleic acid sequence is a sequence within the genome of a cell, e.g., within the genome of a mammalian cell. The targeting RNA may additionally comprise one or more of the features as described herein. In embodiments, the recognizing may occur through hybridization to a predetermined nucleic acid sequence. In embodiments, the targeting RNA hybridizes to a continuous stretch of nucleic acids. In other embodiments the targeting RNA hybridizes to a discontinuous stretch of nucleic acids. In embodiments, the targeting RNA hybridizes to a sequence that is actively transcribed, e.g., actively transcribed in the cell type being studied. In embodiments, the targeting RNA hybridizes to a sequence that does not comprise condensed chromatin, e.g., does not comprise condensed chromatin in the cell type being studied.

A "guide RNA" is a polyribonucleic acid capable of specifically binding to a guide-RNA binding domain, e.g., a polypeptide-based guide-RNA binding domain, e.g., as described herein.

A "guide RNA-binding domain" is a polypeptide capable of specifically binding to a guide RNA, e.g., a polyribonucleic acid-based guide RNA, e.g., as described herein.

A "target DNA sequence" is a polynucleic acid sequence recognized by a targeting RNA, e.g., a targeting RNA as described herein. In embodiments, the target DNA sequence is a sequence that is actively transcribed, e.g., actively transcribed in the cell type being studied. In embodiments, the target DNA sequence is a sequence that does not comprise condensed chromatin, e.g., does not comprise condensed chromatin in the cell type being studied.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. "Complimentary" nucleic acids are nucleic acids that are perfectly complementary or substantially complimentary, and are capable of hybridizing.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993). Laboratory Techniques In Biochemistry And Molecular Biology-Hybridization With Nucleic Acid Probes Part I, Second Chapter "Overview of principles of hybridization and the strategy of nucleic acid probe assay". Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

Gene Editing Systems

Gene editing systems are known in the art, and include but are not limited to, zinc finger nucleases, transcription activator-like effector nucleases (TALENs); clustered regularly interspaced short palindromic repeats (CRISPR)/Cas systems, and meganuclease systems.

CRISPR/Cas Gene Editing System

"CRISPR" or "CRISPR/Cas" as used herein refers to a set of clustered regularly interspaced short palindromic repeats, or a system comprising such a set of repeats. "Cas", as used herein, refers to a CRISPR-associated protein. A "CRISPR/Cas system" refers to a system derived from CRISPR and Cas which can be used to silence or modify a target gene.

Naturally-occurring CRISPR/Cas systems are found in approximately 40% of sequenced eubacteria genomes and 90% of sequenced archaea. Grissa et al. (2007) *BMC Bioinformatics* 8: 172. This system is a type of prokaryotic immune system that confers resistance to foreign genetic elements such as plasmids and phages and provides a form of acquired immunity. Barrangou et al. (2007) *Science* 315: 1709-1712; Marragini et al. (2008) *Science* 322: 1843-1845.

The CRISPR/Cas system has been modified for use in gene editing (silencing, enhancing or modifying specific genes) in eukaryotes such as mice or primates. Wiedenheft et al. (2012) *Nature* 482: 331-8. This is accomplished by, for example, introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in gene editing applications in eukaryotic cells, the spacers are derived from the eukaryotic target gene sequence.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) *Science* 327: 167-170; Makarova et al. (2006) *Biology Direct* 1: 7. The spacers thus serve as templates for RNA molecules, analogously to siRNAs. Pennisi (2013) *Science* 341: 833-836.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) J. Mol. Evol. 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341: 833-836. In some aspects, the Cas9 is derived from a *S. pyogenes* Cas9.

The CRISPR/Cas systems can thus be used to edit a target gene (adding, replacing or deleting one or more base pairs), or introducing a premature stop which thus decreases expression of a target gene. The CRISPR/Cas system can alternatively be used like RNA interference, turning off a target gene in a reversible fashion. In a mammalian cell, for example, the RNA can guide the Cas protein to a target promoter, sterically blocking RNA polymerases.

TALEN Gene Editing System

"TALEN" refers to a transcription activator-like effector nuclease, an artificial nuclease which can be used to edit a target gene.

TALENs are produced artificially by fusing a TAL effector ("TALE") DNA binding domain, e.g., one or more TALEs, e.g., 1, 2, 3, 4, 5, 6, 7, 8, 9 or 10 TALEs to a DNA-modifying domain, e.g., a FokI nuclease domain. Transcription activator-like effects (TALEs) can be engineered to bind any desired DNA sequence. Zhang (2011), *Nature Biotech.* 29: 149-153. By combining an engineered TALE with a DNA cleavage domain, a restriction enzyme can be produced which is specific to any desired DNA sequence. These can then be introduced into a cell, wherein they can be used for genome editing. Boch (2011) *Nature Biotech.* 29: 135-6; and Boch et al. (2009) *Science* 326: 1509-12; Moscou et al. (2009) *Science* 326: 3501. TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence. Zhang (2011), *Nature Biotech.* 29: 149-153

To produce a TALEN, a TALE protein is fused to a nuclease (N), e.g., a wild-type or mutated FokI endonuclease. Several mutations to FokI have been made for its use in TALENs; these, for example, improve cleavage specificity or activity. Cermak et al. (2011) *Nucl. Acids Res.* 39: e82; Miller et al. (2011) *Nature Biotech.* 29: 143-8; Hockemeyer et al. (2011) *Nature Biotech.* 29: 731-734; Wood et al. (2011) *Science* 333: 307; Doyon et al. (2010) *Nature Methods* 8: 74-79; Szczepek et al. (2007) *Nature Biotech.* 25: 786-793; and Guo et al. (2010) *J. Mol. Biol.* 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29: 143-8.

TALEN can be used inside a cell to produce a double-stranded break (DSB) in a target nucleic acid, e.g., a site within a gene. A mutation can be introduced at the break site if the repair mechanisms improperly repair the break via non-homologous end joining. Huertas, P., *Nat. Struct. Mol. Biol.* (2010) 17: 11-16. For example, improper repair may introduce a frame shift mutation. Alternatively, foreign DNA can be introduced into the cell along with the TALEN; depending on the sequences of the foreign DNA and chromosomal sequence, this process can be used to modify a target gene, e.g., correct a defect in the target gene, thus causing expression of a repaired target gene, or e.g., introduce such a defect into a wt gene, thus decreasing expression of a target gene. Miller, J. C., (2011) *Nat. Biotechnol.* 29, 143-148 and Hockemeyer, D. (2011) *Nat. Biotechnol.* 29, 731-734.

Zinc Finger Nuclease Gene Editing System

"ZFN" or "Zinc Finger Nuclease" refer to a zinc finger nuclease, an artificial nuclease which can be used to edit a target gene.

Like a TALEN, a ZFN comprises a DNA-modifying domain, e.g., a nuclease domain, e.g., a FokI nuclease domain (or derivative thereof) fused to a DNA-binding domain. In the case of a ZFN, the DNA-binding domain comprises one or more zinc fingers, e.g., 1, 2, 3, 4, 5, 6, 7, 8, 9 or 10 zinc fingers. Carroll et al. (2011) *Genetics Society of America* 188: 773-782; and Kim et al. (1996) *Proc. Natl. Acad. Sci. USA* 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells. Zinc fingers can be engineered to bind a predetermined nucleic acid sequence. Criteria to engineer a zinc finger to bind to a predetermined nucleic acid sequence are known in the art. Sera (2002), *Biochemistry*, 41:7074-7081; Liu (2008) *Bioinformatics*, 24:1850-1857.

A ZFN using a FokI nuclease domain or other dimeric nuclease domain functions as a dimer. Thus, a pair of ZFNs are required to target non-palindromic DNA sites. The two individual ZFNs must bind opposite strands of the DNA with their nucleases properly spaced apart. Bitinaite et al. (1998) *Proc. Natl. Acad. Sci. USA* 95: 10570-5.

Also like a TALEN, a ZFN can create a double-stranded break in the DNA, which can create a frame-shift mutation if improperly repaired, e.g., via non-homologous end joining, leading to a decrease in the expression of a target gene in a cell. Alternatively, foreign DNA can be introduced into the cell along with the ZFN; depending on the sequences of the foreign DNA and chromosomal sequence, this process can be used to modify a target gene, e.g., correct a defect in the target gene, thus causing expression of a repaired target gene, or e.g., introduce such a defect into a wt gene, thus decreasing expression of a target gene, e.g., as described in WO2013/169802.

Meganuclease Gene Editing System

"Meganuclease" refers to a meganuclease, an artificial nuclease which can be used to edit a target gene.

Meganucleases are derived from a group of nucleases which recognize 15-40 base-pair cleavage sites. Meganucleases are grouped into families based on their structural motifs which affect nuclease activity and/or DNA recognition. Members of the LAGLIDADG family ("LAGLIDADG" disclosed as SEQ ID NO: 45) are characterized by having either one or two copies of the conserved LAGLIDADG motif (SEQ ID NO: 45) (see Chevalier et al. (2001), *Nucleic Acids Res.* 29(18): 3757-3774). The LAGLIDADG meganucleases ("LAGLIDADG" disclosed as SEQ ID NO: 45) with a single copy of the LAGLIDADG motif (SEQ ID NO: 45) form homodimers, whereas members with two copies of the LAGLIDADG motif (SEQ ID NO: 45) are found as monomers. The GIY-YIG family members have a GIY-YIG module, which is 70-100 residues long and includes four or five conserved sequence motifs with four invariant residues, two of which are required for activity (see Van Roey et al. (2002), *Nature Struct. Biol.* 9: 806-811). The His-Cys box meganucleases are characterized by a highly conserved series of histidines and cysteines over a region encompassing several hundred amino acid residues (see Chevalier et al. (2001), *Nucleic Acids Res.* 29(18): 3757-3774). The NHN family, the members are defined by motifs containing two pairs of conserved histidines surrounded by asparagine residues (see Chevalier et al. (2001), *Nucleic Acids Res.* 29(18): 3757-3774).

Strategies for engineering a meganuclease with altered DNA-binding specificity, e.g., to bind to a predetermined nucleic acid sequence are known in the art. E.g., Chevalier et al. (2002), *Mol. Cell.,* 10:895-905; Epinat et al. (2003) *Nucleic Acids Res* 31: 2952-62; Silva et al. (2006) *J Mol Biol* 361: 744-54; Seligman et al. (2002) *Nucleic Acids Res* 30: 3870-9; Sussman et al. (2004) *J Mol Biol* 342: 31-41; Rosen et al. (2006) *Nucleic Acids Res*; Doyon et al. (2006) *J Am Chem Soc* 128: 2477-84; Chen et al. (2009) *Protein Eng Des Sel* 22: 249-56; Arnould S (2006) *J Mol Biol.* 355: 443-58; Smith (2006) *Nucleic Acids Res.* 363(2): 283-94.

A meganuclease can create a double-stranded break in the DNA, which can create a frame-shift mutation if improperly repaired, e.g., via non-homologous end joining, leading to a decrease in the expression of a target gene in a cell. Alternatively, foreign DNA can be introduced into the cell along with the Meganuclease; depending on the sequences of the foreign DNA and chromosomal sequence, this process can be used to modify a target gene, e.g., correct a defect in the target gene, thus causing expression of a repaired target gene, or e.g., introduce such a defect into a wt gene, thus decreasing expression of a target gene, e.g., as described in Silva et al. (2011) *Current Gene Therapy* 11:11-27.

The present invention provides gene editing systems. Without wishing to be bound by theory, it is believed that the gene editing systems of the present invention have the advantages of 1) nucleic acid (e.g., RNA)-based molecules for targeting the gene editing system to a site of interest in genomic DNA which allow for rapid and easy identification and synthesis of targeting RNAs, and 2) compact fusion proteins comprising a cleavage domain that are capable of cleaving genomic DNA as either monomers or dimers.

The gene editing systems of the present invention thus comprise nucleic acid containing a targeting RNA sequence, e.g., a targeting RNA as described herein, and a guide RNA sequence, e.g., a guide RNA as described herein, and chimeric polypeptides comprising a guide-RNA binding domain, e.g., as described herein and a cleavage domain, e.g., as described herein.

It is contemplated that the gene editing systems of the present invention include cleavage domains that can function as monomers, e.g., gene editing systems comprising a single fusion polypeptide comprising a cleavage domain, capable of inducing either a single strand break or a double strand break in the DNA at the target site. Alternatively, provision of multiple targeting RNA components may direct the fusion protein comprising the cleavage domain to more than one target site, e.g., 2, 3, 4, 5, 6, 7, 8, 9, 10 or more sites, to induce more than one cleavage event. An exemplary monomeric gene editing system of the present invention comprises nucleic acid comprising a targeting RNA and a guide RNA and a fusion polypeptide comprising a guide RNA-binding domain (e.g., a polypeptide comprising fewer than 500 amino acids capable of binding the guide RNA) and a cleavage domain (e.g., a monomeric cleavage domain as described herein). The targeting RNA hybridizes with the target DNA sequence and the guide RNA binds to the guide RNA-binding domain, thereby recruiting the cleavage domain to the target site such that DNA at or adjacent to the target site is cleaved.

Alternatively, the gene editing systems of the present invention may comprise cleavage domains that function as multimers, e.g., dimers. For example, a dimeric gene editing system may comprise one or more fusion polypeptides comprising a cleavage domain. Where only one fusion polypeptide comprising a cleavage domain is provided, two different targeting RNA components of the gene editing system may direct the fusion polypeptide comprising a cleavage domain to adjacent sites such that the cleavage domain form a homodimer and cleave the target DNA. Where two fusion polypeptides comprising a cleavage domain are provided, two different targeting RNA components of the gene editing system may direct the fusion polypeptides comprising a cleavage domain to adjacent sites (e.g., one targets the first fusion polypeptide and a second targets the second fusion polypeptide), such that the cleavage domains form a heterodimer capable of cleaving the target DNA. One exemplary dimeric gene editing system of the present invention comprises a first nucleic acid comprising a first targeting RNA and a guide RNA, a second nucleic acid comprising a second targeting RNA and the guide RNA, and a fusion polypeptide comprising a guide RNA-binding domain (e.g., a polypeptide comprising fewer than 1200, 1100, 1000, 900, 800, 700, 600, 500, 400, 300, 200, 175, 150, 125, 100, 75, 50 or 25 amino acids, capable of binding the guide RNA) and a cleavage domain (e.g., a homodimeric cleavage domain as described herein). The each of the first and second targeting RNA hybridizes with their complimentary target DNA sequences (which may be adjacent to each other within the genomic DNA sequence) and the guide RNAs each bind to the guide RNA-binding domain of the fusion protein, thereby recruiting two copies of the cleavage domain to the target site, such that the two copies of the cleavage domain form a homodimer, whereby genomic DNA at or near the target DNA sites is cleaved. In another example of a dimeric gene editing system of the present invention, a nucleic acid comprising a first targeting RNA and a first guide RNA recruits a first fusion protein comprising a first guide RNA-binding domain (e.g., a guide RNA-binding domain as described herein, e.g., a polypeptide of fewer than approximately 500 amino acids, capable of binding the first guide RNA) and a first cleavage domain, while nucleic acid comprising a second targeting RNA (e.g., targeting a target DNA adjacent the target DNA targeted by the first targeting RNA) and a second guide RNA (e.g., a guide RNA with sequence different from that of the first guide RNA) recruits a second fusion protein comprising a second guide RNA-binding domain (e.g., a guide RNA-binding domain as described herein, e.g., a polypeptide of fewer than approximately 500 amino acids, capable of binding the second guide RNA, but not the first guide RNA) and a second cleavage domain. The first and second cleavage domains form a heterodimer, whereby the genomic DNA at or near the target DNA sites is cleaved.

The components of the gene editing system of the present invention are described in detail herein.

Targeting RNA

The targeting RNA is any ribonucleotide sequence having sufficient complementarity with a target polynucleotide sequence, e.g., a target DNA sequence, to hybridize with the target sequence. In some aspects, the targeting RNA is capable of directing sequence-specific cleavage of DNA at or adjacent to the target DNA sequence by a polypeptide comprising a cleavage domain. The targeting RNA is typically about 20 nucleotides. In some embodiments, a targeting RNA is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a targeting RNA is fewer than about 75, 50, 45, 40, 35, 30, 25, 20, 15, 12, or fewer nucleotides in length. In some embodiments, the targeting RNA comprises a sequence of 10 nucleic acids. In some embodiments, the targeting RNA comprises a sequence of 11 nucleic acids. In some embodiments, the targeting RNA comprises a sequence of 12 nucleic acids. In some embodiments, the targeting RNA comprises a sequence of 13 nucleic acids. In some embodiments, the targeting RNA comprises a sequence of 14 nucleic acids. In some embodiments, the targeting RNA comprises a sequence of 15 nucleic acids. In some embodiments, the targeting RNA comprises a sequence of 16 nucleic acids. In some embodiments, the targeting RNA comprises a sequence of 17 nucleic acids. In some embodiments, the targeting RNA comprises a sequence of 18 nucleic acids. In some embodiments, the targeting RNA comprises a sequence of 19 nucleic acids. In some embodiments, the targeting RNA comprises a sequence of 20 nucleic acids. In some embodiments, the targeting RNA comprises a sequence of 21 nucleic acids. In some embodiments, the targeting RNA comprises a sequence of 22 nucleic acids. In some embodiments, the targeting RNA comprises a sequence of 23 nucleic acids. In some embodiments, the targeting RNA comprises a sequence of 24 nucleic acids. In some embodiments, the targeting RNA comprises a sequence of 25 nucleic acids. In some embodiments, the targeting RNA comprises a sequence of 26 nucleic acids.

In some embodiments, the degree of complementarity between a targeting RNA and its corresponding target DNA sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). The ability of a targeting RNA to direct by the polypeptide comprising a cleavage domain at or adjacent to the target sequence may be assessed by any suitable assay. For example, the components of an gene editing system as described herein, including the targeting RNA to be tested, may be provided to a host cell having the complimentary target DNA sequence, such as by transfection with vectors encoding the components of gene editing system, followed by an assessment of preferential cleavage within the target DNA sequence, such as by Surveyor assay as described herein. Similarly, cleavage of a target DNA sequence may be evaluated in a test tube by providing the target DNA sequence, components of a gene editing system, including the targeting RNA to be tested, and a control targeting RNA different from the test targeting RNA, and comparing binding or rate of cleavage at the target DNA sequence between the test and control targeting RNA reactions. Other assays are possible, and will occur to those skilled in the art.

A targeting RNA may be selected to target any target DNA sequence. In some embodiments, the target DNA sequence is a sequence within a genome of a cell. Exemplary target sequences include those that are unique in the target genome. For example, a unique target sequence in a genome may include a sequence NNNNNNNNNNNNNNN, where N is A, G, T, or C, and has a single occurrence in the genome.

In some embodiments, a targeting RNA is selected to reduce the degree of secondary structure within the targeting RNA. Secondary structure may be determined by any suitable polynucleotide folding algorithm. Some programs are based on calculating the minimal Gibbs free energy. An example of one such algorithm is mFold, as described by Zuker and Stiegler (*Nucleic Acids Res.* 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and P A Carr and G M Church, 2009, Nature Biotechnology 27(12): 1151-62).

In embodiments, the targeting RNA hybridizes to a continuous stretch of nucleic acids within the target DNA. In other embodiments the targeting RNA hybridizes to a discontinuous stretch of nucleic acids within the target DNA. In embodiments, the targeting RNA may hybridize to a single-stranded target DNA sequence, for example, though base pairing. In embodiments, the targeting RNA may hybridize to a double-stranded target DNA sequence, for example by hybridizing to the major- or minor-groove edges of the base pairs of the target DNA sequence.

In embodiments, the targeting RNA hybridizes to a target DNA sequence that is actively transcribed, e.g., actively transcribed in the cell type being studied. In embodiments, the targeting RNA hybridizes to a target DNA sequence that does not comprise condensed chromatin, e.g., does not comprise condensed chromatin in the cell type being studied.

Non-limiting examples of targeting RNAs and/or target DNA sequences are described in, for example: Wang T, et al., Science (2013), vol. 343, pp. 80-84 and WO2015/048577, which are hereby incorporated by reference in their entirety. It will be understood by one of ordinary skill that the targeting RNAs of the genome editing systems of the present invention are not limited to those disclosed, for example, in Wang, et al. It will be appreciated that unlike other known gene editing systems, targeting RNAs to virtually any sequence of target DNA can be designed.

Guide RNA

The Guide RNA refers to ribonucleic acid sequence that is capable of binding to a guide RNA-binding domain, e.g., a guide RNA-binding domain as described herein. For example, the Guide RNA refers to an RNA aptamer. Such aptamers, and their corresponding polypeptide-based guide RNA-binding domains are known in the literature, any of which are suitable for use in the present invention. Non-limiting examples of guide RNA/guide RNA-binding domain pairs are described in detail herein.

In some embodiments, the guide RNA is between 1-100, 1-90, 1-80, 1-70, 1-60, 1-50, 1-40, 1-30, 1-20 or 1-10 nucleotides. In some embodiments, the guide RNA is between about 20 and about 100 nucleotides, e.g., between about 30 and about 90, e.g., between about 40 and about 80, e.g., between about 50 and about 70 nucleotides. In some embodiments, the guide RNA is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 or more nucleotides.

Additional guide RNA molecules may be discovered using RNA-based combinatorial libraries, screened against any guide RNA-binding molecule of interest. Those of ordinary skill will appreciate how to design and identify guide RNAs to any guide RNA-binding domain of interest. By way of example, libraries, e.g., phage display libraries, of RNA aptamers may be designed according to known methods, and those libraries may be screened for specific binding to a useful guide RNA-binding domains, also according to known methods. For example, RNA molecules that bind to specific targets of interest, e.g., guide RNA-binding domains, may be identified using SELEX (E.g., Fitzwater et al., *Methods Enzymol.*, vol. 267, pp. 275-301 (1996), which is incorporated herein in its entirety).

Guide RNAs capable of specifically binding to guide RNA-binding domains may also be generated by rational design based on computer modeling and or structural biology.

One- and Two-Component Targeting RNA and Guide RNA Molecules

According to the present invention, the targeting RNA and guide RNA components may be disposed on the same molecule, e.g., on a single nucleic acid molecule, or different nucleic acid molecules, e.g., on two or more nucleic acid molecules.

When the targeting RNA and guide RNA components are disposed on a single nucleic acid molecule, the nucleotides comprising the targeting RNA domain may be directly linked to the nucleotides comprising the guide RNA domain without any intervening sequence. Alternatively, the nucleic acid molecule may additionally comprise sequence disposed between the targeting RNA and guide RNA which covalently links the targeting RNA and guide RNA domains together ("RNA linker"). The RNA linker may comprise between about 1 and about 100 nucleotides, e.g., between about 1-90, 1-80, 1-70, 1-60, 1-50, 1-40, 1-30, 1-20, 1-10, 10-20, 20-30, 30-40, 40-50, or 50-60 nucleotides. The RNA linker may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 or more nucleotides.

In some embodiments of the invention, when the targeting RNA and the guide RNA are disposed on the same nucleic acid molecule, the targeting RNA may be disposed 5' relative to the guide RNA. In other embodiments, the targeting RNA may be disposed 3' relative to the guide RNA.

As an example, the RNA linker sequence is:
(A)n, where n=1-30 (SEQ ID NO: 1).
As another example, the RNA linker sequence is:
(T)n, where n=1-30 (SEQ ID NO: 61). One example is TTTTT (SEQ ID NO: 62). Another example is TTTTTTTTTT (SEQ ID NO: 63). Another example is TTTTTTTTTTTTTTTTTTTT (SEQ ID NO: 64).
As another example, the RNA linker sequence is:
(U)n, where n=1-30 (SEQ ID NO: 65). One example is UUUUU (SEQ ID NO: 66). Another example is UUUUUUUUUU (SEQ ID NO: 67). Another example is UUUUUUUUUUUUUUUUUUUU (SEQ ID NO: 68).

In some embodiments, the targeting RNA and guide RNA are disposed on different nucleic acid molecules. In such cases, the nucleic acid molecule comprising the targeting RNA further comprises a hybridization domain X (e.g., A or B) while the nucleic acid molecule comprising the guide RNA further comprises a hybridization domain X' (e.g., A' or B'). The hybridization domains X and X' are complimentary such that they are capable of specifically hybridizing with each other.

In some embodiments, the hybridization domains X and X' may each comprise between 1-100 complimentary nucleotides, e.g., between about 1-90, 1-80, 1-70, 1-60, 1-50, 1-40, 1-30, 1-20, 1-10, 10-20, 20-30, 30-40, 40-50, or 50-60 complimentary nucleotides. The hybridization domains X and X' may each comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 or more nucleotides. The complementary nucleotides of the hybridization domains X and X' may be contiguous, e.g., with no intervening non-complimentary nucleotides, or may be separated by one or more regions of non-complimentary nucleotides. It will be understood by the skilled artisan that the nucleotides of the hybridization domains X and X' should not be complimentary to the targeting RNA sequence or the guide RNA sequence.

Guide RNA-Binding Domain

The guide RNA-binding domain is a polypeptide capable of binding a guide RNA, e.g., a guide RNA as described herein. Guide RNA/guide RNA-binding domain pairs may be identified as described in the section describing the Guide RNA component of the gene editing systems of the present invention.

In some embodiments, the guide RNA-binding domain of the present invention comprises fewer than about 1500 amino acids. In some embodiments, the guide RNA-binding domain of the present invention comprises fewer than about 1400 amino acids. In some embodiments, the guide RNA-binding domain of the present invention comprises fewer than about 1300 amino acids. In some embodiments, the guide RNA-binding domain of the present invention comprises fewer than about 1200 amino acids. In some embodiments, the guide RNA-binding domain of the present invention comprises fewer than about 1100 amino acids. In some embodiments, the guide RNA-binding domain of the present invention comprises fewer than about 1000 amino acids. In some embodiments, the guide RNA-binding domain of the present invention comprises fewer than about 900 amino acids. In some embodiments, the guide RNA-binding domain of the present invention comprises fewer than about 800 amino acids. In some embodiments, the guide RNA-binding domain of the present invention comprises fewer than about 700 amino acids. In some embodiments, the guide RNA-binding domain of the present invention comprises fewer than about 600 amino acids. In some embodiments, the guide RNA-binding domain of the present invention comprises fewer than about 500 amino acids. In some embodiments, the guide RNA-binding domain of the present invention comprises fewer than about 400 amino acids. In some embodiments, the guide RNA-binding domain of the present invention comprises fewer than about 300 amino acids. In some embodiments, the guide RNA-binding domain of the present invention comprises fewer than about 200 amino acids. In some embodiments, the guide RNA-binding domain of the present invention comprises fewer than about 100 amino acids. In some embodiments, the guide RNA-binding domain of the present invention comprises fewer than about 50 amino acids. In some embodiments, the guide RNA-binding domain comprises between about 50 and about 500 amino acids. In some embodiments, the guide RNA-binding domain comprises between about 50 and about 300 amino acids. In some embodiments, the guide RNA-binding domain comprises between about 100 and about 200 amino acids.

In some embodiments, the guide RNA-binding domain of the present invention comprises fewer than 1500 amino acids. In some embodiments, the guide RNA-binding domain of the present invention comprises fewer than 1400 amino acids. In some embodiments, the guide RNA-binding domain of the present invention comprises fewer than 1300 amino acids. In some embodiments, the guide RNA-binding domain of the present invention comprises fewer than 1200 amino acids. In some embodiments, the guide RNA-binding domain of the present invention comprises fewer than 1100 amino acids. In some embodiments, the guide RNA-binding domain of the present invention comprises fewer than 1000 amino acids. In some embodiments, the guide RNA-binding domain of the present invention comprises fewer than 900 amino acids. In some embodiments, the guide RNA-binding domain of the present invention comprises fewer than 800 amino acids. In some embodiments, the guide RNA-binding domain of the present invention comprises fewer than 700 amino acids. In some embodiments, the guide RNA-binding domain of the present invention comprises fewer than 600 amino acids. In some embodiments, the guide RNA-binding domain of the present invention comprises fewer than 500 amino acids. In some embodiments, the guide RNA-binding domain of the present invention comprises fewer than 400 amino acids. In some embodiments, the guide RNA-binding domain of the present invention comprises fewer than 300 amino acids. In some embodiments, the guide RNA-binding domain of the present invention comprises fewer than 200 amino acids. In some embodiments, the guide RNA-binding domain of the present invention comprises fewer than 100 amino acids. In some embodiments, the guide RNA-binding domain of the present invention comprises fewer than 50 amino acids. In some embodiments, the guide RNA-binding domain comprises between 50 and 500 amino acids. In some embodiments, the guide RNA-binding domain comprises between 50 and 300 amino acids. In some embodiments, the guide RNA-binding domain comprises between 100 and 200 amino acids.

In some embodiments, the guide RNA-binding domain is a polypeptide fragment or analog of an antibody, e.g., a scFv, a Fab, a nanobody, a VL or a VH domain, capable of binding a guide RNA. Antibodies or fragments or analogs thereof suitable for use in the present invention (e.g., that bind a guide RNA) may be generated according to known methods, including as described herein. In some embodiments the guide RNA-binding domain is a fibronectin capable of binding a guide RNA. Guide-RNA binding fibronectins may be generated according to known methods.

In some embodiments, the guide RNA-binding domain is a functional or reporter protein or active fragment or analog thereof. Examples of such functional or reporter proteins include fluorescent proteins, for example, green fluorescent protein, Exemplary guide RNA/guide-RNA binding domain pairs are exemplified below:

Lysozyme

In some embodiments, the guide RNA-binding domain comprises lysozyme or a guide RNA-binding fragment or analog thereof, e.g., is SEQ ID NO: 2:

Lysozyme (UniProt P61626, amino acids 1-148):
MKALIVLGLV LLSVTVQGKV FERCELARTL KRLGM-DGYRG ISLANWMCLA KWESGYNTRA TNYNAGDRST DYGIFQINSR YWCNDGKTPG AVNACHLSCS ALLQDNIADA VACAKRVVRD PQGI-RAWVAW RNRCQNRDVR QYVQGCGV
(SEQ ID NO: 2)

In some aspects of the invention, the guide RNA-binding fragment or analog of SEQ ID NO: 2 will have at least 70, 75, 80, 85, 90, 95, 96, 97, 98, or 99% identity with SEQ ID NO: 2; or will differ by no more than 30, 25, 20, 15, 10, 5, 4, 3, 2, or 1 amino acid residues from the corresponding a sequence of SEQ ID NO: 2 or will comprise at least 145, 140, 130, 120, 110, 100, 95, 90, 85, 80, 75, 70, 65, 60, 55, 50, 45, 40, 35, 30, 25 or 20 amino acids of SEQ ID NO: 2.

In some embodiments, the guide RNA-binding domain comprises a guide RNA-binding fragment or analog of lysozyme, e.g., is SEQ ID NO: 50:

```
                                          (SEQ ID NO: 50)
KVFERCELARTLKRLGMDGYRGISLANWMCLAKWESGYNTRATNYNAG

DRSTDYGIFQINSRYWCNDGKTPGAVNACHLSCSALLQDNIADAVACA

KRVVRDPQGIRAWVAWRNRCQNRDVRQYVQGCGV.
```

In some aspects of the invention, the guide RNA-binding fragment or analog of SEQ ID NO: 50 will have at least 70, 75, 80, 85, 90, 95, 96, 97, 98, or 99% identity with SEQ ID NO: 50; or will differ by no more than 30, 25, 20, 15, 10, 5, 4, 3, 2, or 1 amino acid residues from the corresponding a sequence of SEQ ID NO: 50 or will comprise at least 125, 120, 110, 100, 95, 90, 85, 80, 75, 70, 65, 60, 55, 50, 45, 40, 35, 30, 25 or 20 amino acids of SEQ ID NO: 50.

An exemplary guide RNA for use with a guide RNA-binding domain comprising, e.g., consisting of, SEQ ID NO: 2, or a guide RNA-binding domain comprising, e.g., consisting of, SEQ ID NO: 50, or a guide RNA-binding fragment or analog of SEQ ID NO: 2 or SEQ ID NO: 50 is or comprises:

```
                                          (SEQ ID NO: 3)
GGGAAUGGAUCCACAUCUACGAAUUCAUCAGGGCUAAAGAGUGCAGAG

UUACUUAGUUCACUGCAGACUUGA
```

In some aspects of the invention, the guide RNA will have at least 70, 75, 80, 85, 90, 95, 96, 97, 98, or 99% identity with SEQ ID NO 3; or will differ by no more than 30, 25, 20, 15, 10, 5, 4, 3, 2, or 1 amino acid residues from the corresponding a sequence of SEQ ID NO: 3; or will comprise at least 75, 70, 65, 60, 55, 50, 45, 40, 35, 30, 25 or 20 amino acids of SEQ ID NO: 3.

Additional guide RNAs that may be useful in gene editing systems utilizing a lysozyme-based guide RNA-binding domain are described in Padlan et al., RNA 1, 2014, vol. 20: 447-461, and Cho et al., *Analytica Chimica Acta*, 2006, pp. 82-90, which are hereby incorporated by reference.

Fluorescent Protein

In some embodiments, the guide RNA-binding domain comprises a fluorescent protein, e.g., green fluorescent protein, yellow fluorescent protein, cyan fluorescent protein, enhanced green fluorescent protein, enhanced yellow fluorescent protein, or enhanced cyan fluorescent protein, or a guide RNA-binding fragment or analog thereof.

A green fluorescent protein useful in the present invention, e.g., as a guide RNA-binding domain, includes any of the green fluorescent proteins known in the art. Non-limiting examples include the proteins with UniProt entry numbers identified in Table 1:

TABLE 1

| Green Florescent Proteins UniProt Entry Code |
|---|
| Q8GHE2 |
| Q71RY9 |
| Q8GHE4 |
| Q8GHE3 |
| E2NJN5 |
| B3CDX7 |
| B1PNC4 |
| B1PNB8 |
| B1PNB9 |
| B1PNC0 |
| B1PNC1 |
| B1PNC2 |
| B1PNC3 |
| R7E1H1 |
| K0KNG7 |
| T2HNK0 |
| Q2MHN7 |
| Q5TLG6 |
| U6M9S0 |
| U6M5D0 |
| B9UPG6 |
| P42212 |
| M4VQY4 |
| M4VUA6 |
| M4W8Q2 |
| M4W8Q9 |
| M4VUA1 |
| M4VU52 |
| M4W8L4 |
| M4VQU3 |
| M4W8N1 |

TABLE 1-continued

Green Florescent Proteins
UniProt Entry Code

| Column 1 | Column 2 |
|---|---|
| M4VSS3 | M4VQL4 |
| M4VQW3 | M4VUB1 |
| M4VQG3 | M4VUB6 |
| M4VQV1 | M4W8T3 |
| M4VQV5 | B0ZZ77 |
| M4VUE2 | W6KDG8 |
| M4VR04 | B6UPG7 |
| M4VQK9 | A0A060N2E9 |
| M4VQX9 | A0A097ZN69 |
| M4VU96 | A0A097ZN73 |
| M4VSX6 | A0A097ZN71 |
| M4VQK1 | A0A097ZN82 |
| M4W8R3 | A0A097ZN76 |
| M4VQJ6 | Q6R8F5 |
| M4VU71 | J9PGT0 |
| M4VU57 | D7PM04 |
| M4VST7 | D7PM05 |
| M4VSV8 | Q6R8F4 |
| M4VQI2 | J9PGG2 |
| M4VST2 | D7PM10 |
| M4VQW8 | Q6R8F3 |
| M4VQH3 | J9PIH6 |
| M4VSU6 | D7PM06 |
| M4VQE5 | J9PJD5 |
| M4W8N9 | D7PM12 |
| M4VQV9 | Q8WP95 |
| M4W8M3 | R0EHP5 |
| M4VSS7 | Q53UG7 |
| M4VU47 | W2JZJ6 |
| M4W8N5 | J8VIQ3 |
| M4VSU1 | A7VMR3 |
| M4VQF9 | Q6I7B2 |
| M4W8M7 | B9U1C3 |
| M4VQU7 | A0A080K075 |
| M4VU87 | A0A080K5K8 |
| M4VQX4 | Q9U6Y5 |
| M4VU43 | Q9U6Y4 |
| M4VQH8 | Q9U6Y6 |
| M4W8P3 | Q9U6Y3 |
| M4W8L8 | Q9U6Y7 |
| M4VQG7 | Q9GZ28 |
| M4VSW3 | Q9GPI6 |
| M4VQF4 | Q6RYS6 |
| Q86LV4 | Q6RYS5 |
| M4VSX1 | Q8T6U0 |
| M4VR28 | Q8MU48 |
| M4VQM8 | Q66PU5 |
| M4W8Q6 | Q8MMA2 |
| M4VQN2 | A8CLR1 |
| M4W8V1 | A8QVZ9 |
| M4VT13 | Q66PW0 |
| M4W8U7 | Q8T5E9 |
| Q86LC2 | Q8MU46 |
| Q17106 | B5T1L4 |
| Q17105 | B5T1L3 |
| A0A059PIQ0 | Q66PV8 |
| Q963I9 | A8CLY3 |
| Q9BLZ0 | B5LIN0 |
| Q8WTC9 | Q8MU45 |
| Q8WTC5 | B6CTZ6 |
| Q8WTC7 | B6CTZ4 |
| Q8WTC6 | Q8MMA1 |
| Q8WTC8 | A8CLX9 |
| Q8WTC4 | D1J6P8 |
| Q8WTD0 | Q8T6T8 |
| Q9BLY9 | D2IGW4 |
| M4VT07 | D2IGW2 |
| M4VUC0 | D2IGW3 |
| M4W8T7 | Q1ALD4 |
| M4VR08 | Q1ALD5 |
| M4W8S7 | Q09HR5 |
| M4VSZ5 | Q2VTM8 |
| M4VQL8 | Q2VTM9 |
| M4VQM3 | Q1ALD3 |
| M4VUD0 | D1KWU6 |
| M4VR01 | A8CLU1 |
| M4VUD5 | Q66PV7 |

TABLE 1-continued

Green Florescent Proteins
UniProt Entry Code

Q66ND2
Q2LI64
Q2LI65
Q962P9
A8CLT7
Q8T6T9
I0IUJ1
D1KWT9
D1KWT7
Q6WV09
Q6WV10
D1KWT5
A8CLS7
B2ZAG1
D1KWT1
Q86LV8
Q86LV7
H3JQU5
Q6WV11
Q5ZQQ5
Q963F5
Q7Z0W5
A7UAM0
Q7Z0W4
A7UAL6
Q66ND3
A7UAL5
A7UAL8
A7UAL2
Q7Z0W6
Q95VT0
A7UAL1
A7UAL9
Q7Z0W8
Q66ND5
A7UAL7
A7UAL3
Q7Z0W7
A8CLP7
A8CLR7
D1KWT4
Q60I24
Q60I25
A8CLT2
Q6YGZ0
Q6WV12
Q6WV13
B6CTZ3
A5YTR6
A8CLS2
A8CLQ1
A8CLW4
A8CLW1
B6CTZ5
Q6WV08
G1JSF3
G1JSF2
G1JSF4
Q66PV9
A8CLN4
A8CLP2
A8CLV1
A3F208

In some embodiments the guide RNA-binding domain comprises the sequence of green fluorescent protein UniProt code P42212.

An enhanced green fluorescent protein useful in the present invention, e.g., as a guide RNA-binding domain, includes any of the enhanced green fluorescent proteins known in the art. Non-limiting examples are disclosed in, for example, Cormack et al., Gene, vol. 173, pp. 33-38 (1996), and also include the proteins with UniProt entry numbers identified in Table 2:

TABLE 2

Enhanced Green Fluorescent Proteins
UniProt Entry Code

W8GN23
C5MKY7
A0A076FL24
Q66ND4
D8LBZ3
C8CHS1

A yellow fluorescent protein useful in the present invention, e.g., as a guide RNA-binding domain, includes any of the yellow fluorescent proteins known in the art. Non-limiting examples are disclosed in, for example, Ormo et al., Science, vol. 273, pp. 1392-1395 (1996), and also include the proteins with UniProt entry numbers identified in Table 3:

TABLE 3

Yellow Fluorescent Proteins
Uniprot Entry Code

P21578
Q6RYS7
B3HA30
A0A059PIR9
G1JSF4
Q2VTM8
G4CFR9

An enhanced yellow fluorescent protein useful in the present invention, e.g., as a guide RNA-binding domain, includes any of the enhanced yellow fluorescent proteins known in the art.

A cyan fluorescent protein useful in the present invention, e.g., as a guide RNA-binding domain, includes any of the cyan fluorescent proteins known in the art. Non-limiting examples are disclosed in, for example, Heim et al., Current Biol., vol. 6, pp. 178-182 (1996), and also include the proteins with UniProt entry numbers identified in Table 4:

TABLE 4

Cyan Fluorescent Proteins
UniProt Entry Code

A0A059PIU2
B6CTZ2
Q95UA7
A7UAL1
A8CLP7
A8CLP2
Q66ND6
Q7Z0W5
Q66PV6
Q5ZQQ6
A8CLW9
Q66PV5
A8CLU7
Q66PV4
Q66PV3
B5T1L0
Q66ND1
B5T1L2

An enhanced cyan fluorescent protein useful in the present invention, e.g., as a guide RNA-binding domain, includes any of the enhanced cyan fluorescent proteins known in the art.

In some aspects of the invention, the guide RNA-binding fragment or analog of any of the fluorescent proteins identified herein, e.g., in Tables 1-4, will have at least 70, 75, 80, 85, 90, 95, 96, 97, 98, or 99% identity with any of the proteins identified herein, e.g., in Tables 1-4; or will differ by no more than 30, 25, 20, 15, 10, 5, 4, 3, 2, or 1 amino acid residues from the corresponding a sequence of any of the proteins identified herein, e.g., in Tables 1-4; or will comprise at least 145, 140, 130, 120, 110, 100, 95, 90, 85, 80, 75, 70, 65, 60, 55, 50, 45, 40, 35, 30, 25 or 20 amino acids of any of the proteins identified herein, e.g., in Tables 1-4.

An exemplary guide RNA for use with a guide RNA-binding domain comprising any of the proteins identified in Tables 1-4 or a guide RNA-binding fragment or analog thereof is or comprises:

(SEQ ID NO: 10)
GCGUGAGACGUCUUGAUGAAAUCCGGCUCGGCAAUGGUUCGUGGCGAA

UUGGGUGGGGAAAGUCCUGAAAAGAGGGCCACCACAGAAGCUUGUGGA

GUUAACAGCAAA

In some aspects of the invention, the guide RNA will have at least 70, 75, 80, 85, 90, 95, 96, 97, 98, or 99% identity with SEQ ID NO 10; or will differ by no more than 30, 25, 20, 15, 10, 5, 4, 3, 2, or 1 amino acid residues from the corresponding a sequence of SEQ ID NO 10; or will comprise at least 75, 70, 65, 60, 55, 50, 45, 40, 35, 30, 25 or 20 amino acids of SEQ ID NO: 10.

Additional guide RNAs suitable for use with fluorescent protein-based guide RNA-binding domains are described in Shui et al., *Nuc. Acids Res.*, 2012, vol. 40: e39 (pp. 1-11). Additional guide RNAs suitable for use with fluorescent protein-based guide RNA-binding domains may also be discovered using the methods described in, for example, Shui et al., *Nuc. Acids Res.*, 2012, vol. 40: e39 (pp. 1-11).

Antibody or Antibody Fragments or Analogs

In some embodiments, the guide RNA-binding domain comprises an antibody or antibody fragment or analog thereof. For example, the guide RNA-binding domain may comprise a scFv of an antibody selected for binding to a guide RNA. The guide RNA-binding domain may be any fragment or analog of an antibody capable of binding a guide RNA of interest that retains the ability to bind the guide RNA, e.g., a Fab, a nanobody, or a single domain fragment such as a light chain variable domain (VL) or heavy chain variable domain (VH). Alternatively, the guide RNA-binding domain may comprise any known antibody, or fragment or analog thereof, and an RNA aptamer selected for specific binding to that antibody, according to known methods such as those described herein, may be used as the guide RNA.

An example of an aptamer that binds to an antibody or fragment or analog thereof is described in Cho et al., *Analytica Chimica Acta*, 2006, pp. 82-90:

(SEQ ID NO: 11)
GGGGCACGTTTATCCGTCCCTCCTAGTGGCGTGCCCC

In some aspects of the invention, the guide RNA will have at least 70, 75, 80, 85, 90, 95, 96, 97, 98, or 99% identity with SEQ ID NO 11; or will differ by no more than 30, 25, 20, 15, 10, 5, 4, 3, 2, or 1 amino acid residues from the corresponding a sequence of SEQ ID NO 11; or will comprise at least 35, 30, 25 or 20 amino acids of SEQ ID NO: 11.

In the case of SEQ ID NO: 11 (or a fragment or analog thereof), IgE or a SEQ ID NO: 11-binding fragment or analog of IgE is used as the guide RNA-binding domain.

In another aspect, the guide RNA-binding domain comprises a constant region of an antibody, e.g., a constant region of a human antibody, e.g., an Fc fragment of a human IgG1 antibody, or a guide RNA-binding fragment or analog thereof, e.g., comprises SEQ ID NO: 40:

Human IgG1 Fc:
(SEQ ID NO: 40)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

In some aspects of the invention, the guide RNA-binding fragment or analog of IgG1 Fc will have at least 70, 75, 80, 85, 90, 95, 96, 97, 98, or 99% identity with SEQ ID NO: 40; or will differ by no more than 155, 150, 145, 140, 135, 130, 120, 110, 100, 90, 80, 70, 60, 50, 40, 30, 25, 20, 15, 10, 5, 4, 3, 2, or 1 amino acid residues from the corresponding a sequence of SEQ ID NO: 40, or will comprise at least 330, 325, 320, 315, 310, 300, 290, 280, 270, 260, 250, 240, 230, 220, 210, 200, 190, 180, 170, 160, 150, 140, 130, 120, 110, 100, 90, 80, 70, 60, or 50 amino acids of SEQ ID NO: 40.

An exemplary guide RNA for use with a guide RNA-binding domain comprising an IgG1 Fc sequence, e.g., SEQ ID NO: 40, or a guide RNA-binding fragment or analog thereof is or comprises:

(SEQ ID NO: 41)
5'-GGAGGUGCUCCGAAAGGAACUCC-3'

In some aspects of the invention, the guide RNA will have at least 70, 75, 80, 85, 90, 95, 96, 97, 98, or 99% identity with SEQ ID NO: 41; or will differ by no more than 15, 10, 9, 8, 7, 6, 5, 4, 3, 2, or 1 amino acid residues from the corresponding a sequence of SEQ ID NO: 41; or will comprise at least 22, 21, 20, 19, 18, 17, 16, 15, 14, 13, 12, 11, or 10 amino acids of SEQ ID NO: 41.

Additional guide RNAs that may be useful in gene editing systems utilizing a IgG1 Fc-based guide RNA-binding domain are described in, for example, Miyakawa et al., *RNA*, vol. 14, pp. 1154-1163 (2008), which is hereby incorporated by reference.

Lipocalin-2

In some embodiments, the guide RNA-binding domain comprises a sequence of murine lipocalin-2 (mLcn2) or an RNA-binding fragment or analog thereof. mLcn-2 suitable for the present invention is available from R&D Systems, and is described, for example, in Zhai et al., *Anal. Chem.*, vol. 84, pp. 8763-8770 (2012).

In some aspects of the invention, the guide RNA-binding fragment or analog of mLcn2 will have at least 70, 75, 80, 85, 90, 95, 96, 97, 98, or 99% identity with mLcn2; or will differ by no more than 30, 25, 20, 15, 10, 5, 4, 3, 2, or 1 amino acid residues from the corresponding a sequence of mLcn2 or will comprise at least 145, 140, 130, 120, 110, 100, 95, 90, 85, 80, 75, 70, 65, 60, 55, 50, 45, 40, 35, 30, 25 or 20 amino acids of mLcn2.

An exemplary guide RNA for use with a guide RNA-binding domain comprising mLcn2 or a guide RNA-binding fragment or analog thereof is or comprises:

(SEQ ID NO: 4)
5'CCUCCGGCUCAUACCUUUUCGAAGACAAGCUUCGACAGGAGG-3'

In some aspects of the invention, the guide RNA will have at least 70, 75, 80, 85, 90, 95, 96, 97, 98, or 99% identity with SEQ ID NO: 4; or will differ by no more than 30, 25, 20, 15, 10, 5, 4, 3, 2, or 1 amino acid residues from the corresponding a sequence of SEQ ID NO: 4; or will comprise at least 75, 70, 65, 60, 55, 50, 45, 40, 35, 30, 25 or 20 amino acids of SEQ ID NO: 4.

Additional guide RNAs that may be useful in gene editing systems utilizing a mLcn2-based guide RNA-binding domain are described in, for example, Zhai et al., *Anal. Chem.* Vol. 84, pp. 8763-8770 (2012), which is hereby incorporated by reference.

Special Elongation Factor SelB

In some embodiments, the guide RNA-binding domain comprises a sequence of special elongation factor SelB or an RNA-binding fragment or analog thereof. SelB (Forchammer et al., *Nature*, vol. 342, pp. 453-456 (1989), hereby incorporated by reference) suitable for the present invention includes, for example, the polypeptide associated with UniProt code P14018.

In some aspects of the invention, the guide RNA-binding fragment or analog of SelB will have at least 70, 75, 80, 85, 90, 95, 96, 97, 98, or 99% identity with SelB, e.g., UniProt code P14018; or will differ by no more than 30, 25, 20, 15, 10, 5, 4, 3, 2, or 1 amino acid residues from the corresponding a sequence of SelB, e.g., UniProt code P14018, or will comprise at least 145, 140, 130, 120, 110, 100, 95, 90, 85, 80, 75, 70, 65, 60, 55, 50, 45, 40, 35, 30, 25 or 20 amino acids of SelB, e.g., UniProt code P14018.

An exemplary guide RNA for use with a guide RNA-binding domain comprising SelB, e.g., UniProt code P14018, or a guide RNA-binding fragment or analog thereof is or comprises:

(SEQ ID NO: 5)
5'-GCGCUAAGUCCUCGCUCAGCCCAUAAGUUGUCCCAAGUCUUGGG
CGCAAAUACAUCCCACGCGCGACUCGGAUCCG-3'

In some aspects of the invention, the guide RNA will have at least 70, 75, 80, 85, 90, 95, 96, 97, 98, or 99% identity with SEQ ID NO: 5; or will differ by no more than 30, 25, 20, 15, 10, 5, 4, 3, 2, or 1 amino acid residues from the corresponding a sequence of SEQ ID NO: 5; or will comprise at least 75, 70, 65, 60, 55, 50, 45, 40, 35, 30, 25 or 20 amino acids of SEQ ID NO: 5.

Additional guide RNAs that may be useful in gene editing systems utilizing a mLcn2-based guide RNA-binding domain are described in, for example, Klug et al., *RNA*, vol. 5, pp. 1180-1190 (1995), which is hereby incorporated by reference.

Severe Acute Respiratory Syndrome Coronavirus NTPase/Helicase

In some embodiments, the guide RNA-binding domain comprises a sequence of severe acute respiratory syndrome coronavirus NTPase/Helicase, for example the severe acute respiratory syndrome coronavirus NTPase/Helicase described in, Tanner et al., *J. Biol. Chem.*, vol. 278, pp. 39578-39582 (2003), hereby incorporated by reference, or an RNA-binding fragment or analog thereof.

In some aspects of the invention, the guide RNA-binding fragment or analog of severe acute respiratory syndrome coronavirus NTPase/Helicase will have at least 70, 75, 80, 85, 90, 95, 96, 97, 98, or 99% identity with severe acute respiratory syndrome coronavirus NTPase/Helicase; or will differ by no more than 30, 25, 20, 15, 10, 5, 4, 3, 2, or 1 amino acid residues from the corresponding a sequence of severe acute respiratory syndrome coronavirus NTPase/Helicase, or will comprise at least 145, 140, 130, 120, 110, 100, 95, 90, 85, 80, 75, 70, 65, 60, 55, 50, 45, 40, 35, 30, 25 or 20 amino acids of severe acute respiratory syndrome coronavirus NTPase/Helicase.

An exemplary guide RNA for use with a guide RNA-binding domain comprising severe acute respiratory syndrome coronavirus NTPase/Helicase, or a guide RNA-binding fragment or analog thereof is or comprises:

(SEQ ID NO: 6)
5'-GAUAAUACGACUCACUAUAGGGUUCACUGCAGACUUGACGAAGC
UUGCAGAAAAGGGGAAGAAGAGGGUGAUUCAGGCGAGAGAAUGGAU
CCACAUCUACGAAUUC-3'

In some aspects of the invention, the guide RNA will have at least 70, 75, 80, 85, 90, 95, 96, 97, 98, or 99% identity with SEQ ID NO: 6; or will differ by no more than 30, 25, 20, 15, 10, 5, 4, 3, 2, or 1 amino acid residues from the corresponding a sequence of SEQ ID NO: 6; or will comprise at least 100, 95, 90, 85, 80, 75, 70, 65, 60, 55, 50, 45, 40, 35, 30, 25 or 20 amino acids of SEQ ID NO: 6.

Additional guide RNAs that may be useful in gene editing systems utilizing a severe acute respiratory syndrome coronavirus NTPase/Helicase-based guide RNA-binding domain are described in, for example, Jang et al., *Biochem. Biophys. Res. Comm.*, vol. 366, pp. 738-744 (2008), which is hereby incorporated by reference.

Histidine Tag

In some embodiments, the guide RNA-binding domain comprises a polyhistidine sequence, for example, a histidine tag, or a guide RNA-binding fragment or analog thereof, e.g., comprises, e.g., consists of, SEQ ID NO: 7:

Histidine Tag:
RGSHHHHHH (SEQ ID NO: 7)

In some aspects of the invention, the guide RNA-binding fragment or analog of a histidine tag will have at least 70, 75, 80, 85, 90, 95, 96, 97, 98, or 99% identity with SEQ ID NO: 7; or will differ by no more than 5, 4, 3, 2, or 1 amino acid residues from the corresponding a sequence of SEQ ID NO: 7, or will comprise at least 6, 5, 4, or 3 amino acids of SEQ ID NO: 7. In some aspects of the invention, the histidine tag will comprise at least 4, at least 5, at least 6, at least 7, at least 8, at least 9, at least 10, at least 11, at least 12, at least 13, at least 14, at least 15, or at least 16 histidine residues.

In some embodiments, the guide RNA-binding domain comprises a polyhistidine sequence, for example, a histidine tag, or a guide RNA-binding fragment or analog thereof, e.g., comprises, e.g., consists of, SEQ ID NO: 7:

Histidine8 Tag:
(SEQ ID NO: 51)
RGSHHHHHHHH

In some aspects of the invention, the guide RNA-binding fragment or analog of a histidine tag will have at least 70, 75, 80, 85, 90, 95, 96, 97, 98, or 99% identity with SEQ ID NO: 51; or will differ by no more than 5, 4, 3, 2, or 1 amino acid residues from the corresponding a sequence of SEQ ID NO: 51, or will comprise at least 6, 5, 4, or 3 amino acids of SEQ ID NO: 51. In other aspects, the guide RNA-binding domain consists of HHHHHH (SEQ ID NO: 52). In other aspects, the guide RNA-binding domain consists of HHHHHHHH (SEQ ID NO: 53).

In some aspects of the invention, the histidine tag will comprise, e.g., consist of, 4, 5, 6, 7, 8, 9, 10, 11, 12, 13, 14, 15, or 16 histidine residues.

An exemplary guide RNA for use with a guide RNA-binding domain comprising a histidine tag, e.g., SEQ ID NO: 7 SEQ ID NO: 51, SEQ ID NO: 52 or SEQ ID NO: 53, or a guide RNA-binding fragment or analog thereof, is or comprises:

```
                                              (SEQ ID NO: 8)
5'-GGGUACGCUCAGGUAUAUUGGCGCCUUCGUGGAAUGUCAGUGCC
UGGACGUGCAGU-3'
```

In some aspects of the invention, the guide RNA will have at least 70, 75, 80, 85, 90, 95, 96, 97, 98, or 99% identity with SEQ ID NO: 8; or will differ by no more than 30, 25, 20, 15, 10, 5, 4, 3, 2, or 1 amino acid residues from the corresponding a sequence of SEQ ID NO: 8; or will comprise at least 55, 50, 45, 40, 35, 30, 25 or 20 amino acids of SEQ ID NO: 8.

Additional guide RNAs that may be useful in gene editing systems utilizing a histidine tag-based guide RNA-binding domain are described in, for example, Tsuji et al., *Biochem. Biophys. Res. Comm.*, vol. 386, pp. 227-231 (2009), which is hereby incorporated by reference.

Streptavidin

In some embodiments, the guide RNA-binding domain comprises a streptavidin sequence, or a guide RNA-binding fragment or analog thereof, e.g., comprises SEQ ID NO: 9:

```
Streptavidin:
                                              (SEQ ID NO: 9)
DPSKDSKAQVSAAEAGITGTWYNQLGSTFIVTAGADGALTGTYESAV

GNAESRYVLTGRYDSAPATDGSGTALGWTVAWKNNYRNAHSATTWSG

QYVGGAEARINTQWLLTSGTTEANAWKSTLVGHDTFTKVKPSAASID

AAKKAGVNNGNPLDAVQQ
```

In some aspects of the invention, the guide RNA-binding fragment or analog of streptavidin will have at least 70, 75, 80, 85, 90, 95, 96, 97, 98, or 99% identity with SEQ ID NO: 7; or will differ by no more than 30, 25, 20, 15, 10, 5, 4, 3, 2, or 1 amino acid residues from the corresponding a sequence of SEQ ID NO: 9, or will comprise at least 155, 150, 145, 140, 135, 130, 120, 110, 100, 90, 80, 70, 60, or 50 amino acids of SEQ ID NO: 9.

An exemplary guide RNA for use with a guide RNA-binding domain comprising a streptavidin sequence, e.g., SEQ ID NO: 9, or a guide RNA-binding fragment or analog thereof is or comprises:

```
                                              (SEQ ID NO: 39)
5'-AUGCGGCCGCCGACCAGAAUCAUGCAAGUGCGUAAGAUAGUCGC
GGGUCGGCGGCCGCAU-3'
```

In some aspects of the invention, the guide RNA will have at least 70, 75, 80, 85, 90, 95, 96, 97, 98, or 99% identity with SEQ ID NO: 39; or will differ by no more than 30, 25, 20, 15, 10, 5, 4, 3, 2, or 1 amino acid residues from the corresponding a sequence of SEQ ID NO: 39; or will comprise at least 55, 50, 45, 40, 35, 30, 25 or 20 amino acids of SEQ ID NO: 39.

Additional guide RNAs that may be useful in gene editing systems utilizing a streptavidin-based guide RNA-binding domain are described in, for example, Leppek et al., *Nucl. Acids Res.*, vol. 42(2), p. e13 (2014), which is hereby incorporated by reference.

Additional exemplary guide RNA/guide RNA-binding domain pairs are available from Aptagen (www.aptagen.com), whose catalog is hereby incorporated by reference.

Nuclease or Cleavage Domains

In one aspect of the invention, the guide RNA-binding domain is the cleavage domain itself, and the guide RNA binds directly to said cleavage domain (e.g., the cleavage domain is both the guide RNA-binding domain and the cleavage domain). In such embodiments, it may be unnecessary for the gene editing system to comprise an additional guide RNA-binding domain. Without wishing to be bound by theory, it is believed that in embodiments where the guide RNA binds directly to the cleavage domain, the cleavage domain must retain cleavage activity when bound to the guide RNA. An example of a gene editing system comprising a guide RNA that binds directly to the cleavage domain would include nucleic acid encoding a targeting RNA and a guide RNA and a polypeptide comprising a cleavage domain. The guide RNA would bind to the cleavage domain and target said cleavage domain to the target site, whereby the nucleic acid at or adjacent to the target site is cleaved. In such embodiments, the cleavage domain is preferably fewer than about 800 amino acids, e.g., fewer than about 700 amino acids, e.g., fewer than about 600 amino acids, e.g., fewer than about 500 amino acids, e.g., fewer than about 400 amino acids, e.g., fewer than about 300 amino acids, e.g., fewer than about 200 amino acids, e.g., fewer than about 100 amino acids. In one embodiment, the cleavage domain is a Fok-I-derived (e.g., SEQ ID NO 12) or a Tev-I-derived cleavage domain, e.g., as described herein.

The examples above are not intended to be limiting, and one of ordinary skill in the art will appreciate that other RNA aptamer:binding protein pairs known in the art may be used.

Cleavage Domains

The cleavage domains for use in the gene editing systems of the present invention may be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains.

Cleavage domains include "cleavage half-domains," which is a domain derived from any nuclease or portion thereof, as set forth above, that requires dimerization for cleavage activity. In general, two cleavage domains are required for cleavage if the fusion proteins comprise cleavage half-domains. When gene editing systems utilizing cleavage half-domains are utilized, the target sites for the two targeting RNAs are preferably disposed, with respect to each other, such that binding of the two targeting RNAs to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one aspect of the invention, the cleavage domains comprise the cleavage domain (or cleavage half-domain) from at least one Type IIS restriction enzyme, which may or may not be engineered.

An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. Accordingly, for the purposes of the present disclosure, the portion of the Fok I enzyme used as the cleavage domain is considered a cleavage half-domain. Thus, for targeted double-stranded cleavage and/or targeted replacement of cellular sequences using gene editing systems comprising a Fok I-based cleavage domain, two Fok-I-based cleavage domains (either two copies of the same Fok-I-based cleavage domain which are capable of homodimerizing or two different Fok-I-based cleavage domains which are capable of heterodimerizing) are recruited to the target site.

An example of a Fok-I-based cleavage domain for use in the present invention is:

```
                                          (SEQ ID NO: 12)
GSQLVKSELEEKKSELREIKLKYVPHEYIELIEIARNSTQDRILEMK

VMEFFMKVYGYRGKEILGGSRKPDGAIYTVGSPIDYGVIVDTKAYSG

GYNLPIGQADEMQRYVEENQTRNKHINPNEWWKVYPSSVIEFKFLFV

SGEIFKGNYKAQLTRLNHITNCNGAVLSVEELLIGGEMIKAGTLTLE

EVRRKFNNGEINF
```

In some aspects of the invention, the cleavage domain will have at least 70, 75, 80, 85, 90, 95, 96, 97, 98, or 99% identity with SEQ ID NO 12; or will differ by no more than 60, 50, 40, 30, 25, 20, 15, 10, 9, 8, 7, 6, 5, 4, 3, 2, or 1 amino acid residues from the corresponding a sequence of SEQ ID NO 12; or will comprise at least 240, 235, 230, 225, 220, 215, 210, 200, 180, 160, 140, 120, 100, 80, 60, 40 or 20 amino acids of SEQ ID NO: 12.

Another example of a Fok-I-based cleavage domain for use in the present invention is:

```
                                          (SEQ ID NO: 49)
KSELREIKLKYVPHEYIELIEIARNSTQDRILEMKVMEFFMKVYGYR

GKELGGSRKPDGAIYTVGSPIDYGVIVDTKAYSGGYNLPIGQADEMQ
```

```
                           -continued
RYVEENQTRNKHINPNEWWKVYPSSVTEFKFLFVSGHFKGNYKAQLT

RLNHITNCNGAVLSVEELLIGGEMIKAGTLTLEEVRRKFNNGEINF
```

In some aspects of the invention, the cleavage domain will have at least 70, 75, 80, 85, 90, 95, 96, 97, 98, or 99% identity with SEQ ID NO 49; or will differ by no more than 60, 50, 40, 30, 25, 20, 15, 10, 9, 8, 7, 6, 5, 4, 3, 2, or 1 amino acid residues from the corresponding a sequence of SEQ ID NO 49; or will comprise at least 240, 235, 230, 225, 220, 215, 210, 200, 180, 160, 140, 120, 100, 80, 60, 40 or 20 amino acids of SEQ ID NO: 49.

A cleavage domain or cleavage half-domain can be any portion of a protein that retains cleavage activity, or that retains the ability to multimerize (e.g., dimerize) to form a functional cleavage domain.

In some embodiments, the cleavage domain is or is derived from a type IIS restriction enzyme. Exemplary Type IIS restriction enzymes are described in International Publication WO 07/014,275, incorporated herein in its entirety. Additional restriction enzymes also contain separable binding and cleavage domains, and use of the separable cleavage domains are contemplated by the present disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished when one or more pairs of nucleases containing these cleavage half-domains are used for cleavage. See, e.g., U.S. Patent Publication No. 20080131962, the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in U.S. Patent Publication. Nos. 20050064474 (Example 5) and 20070134796 (Example 38).

In another embodiment, a monomeric nuclease cleavage domain may be used (e.g., a cleavage domain capable of cleaving target nucleic acid as a monomer). Examples of such monomeric cleavage domains are described in Kleinstiver et al., *Proc. Nat'l Acad. Sci. USA*, 2012, vol. 109, pp. 8061-8066. In some aspects, the cleavage domain is derived from a GIY-YIG homing endonuclease, e.g., is derived from I-TevI or I-BmoI.

In some aspects, the cleavage domain is or is derived from:

```
(TevI amino acids 1-206; UniProt Code A0A097J3K0-1)
                                    (SEQ ID NO: 13)
MKSGIYQIKN TLNNKVYVGS AKDFEKRWKR HFKDLEKGCH

SSIKLQRSFN KHGNVFECSI LEEIPYEKDL IIERENFWIK

ELNSKINGYN IADATFGDTC STHPLKEEII KKRSETVKAK

MLKLGPDGRK ALYSKPGSKN GRWNPETHKF CKCGVRIQTS

AYTCSKCRNR SGENNSFFNH KHSDITKSKI SEKMKGKKPS

NIKKIS
```

In some aspects of the invention, the cleavage domain will have at least 70, 75, 80, 85, 90, 95, 96, 97, 98, or 99% identity with SEQ ID NO 13; or will differ by no more than 60, 50, 40, 30, 25, 20, 15, 10, 9, 8, 7, 6, 5, 4, 3, 2, or 1 amino acid residues from the corresponding a sequence of SEQ ID NO 13; or will comprise at least 205, 204, 203, 202, 201, 200, 190, 180, 170, 160, 150, 140, 120, 100, 80, 60, 40 or 20 amino acids of SEQ ID NO: 13.

Polypeptide Linkers

The fusion polypeptide comprising a guide RNA-binding domain and a cleavage domain may optionally additionally comprise a linker disposed between the guide RNA-binding domain and the cleavage domain. Without wishing to be bound by theory, a linker may be used to obtain the proper spacing between the target site and the site of cleavage, and in the case of gene editing systems using dimeric cleavage domains, may be used to obtain the proper alignment between the two cleavage domains to allow them to dimerize. One of ordinary skill in the art will appreciate how to ascertain the suitability of any linker by, for example, performing one of the in vivo or in vitro assays for targeted cleavage described herein or known in the art.

Polypeptide likers are known in the art. By way of example, the linker may be (GGS)$_n$ (SEQ ID NO: 46), (GGGS)$_n$ (SEQ ID NO: 47), or (GGGGS)$_n$ (SEQ ID NO: 48), where n=1-20. Alternatively, the linker may be a linker disclosed in, for example, Tsai et al., *Nature Biotechnol.*, 2014, vol. 32: pp. 569-576. For example, the linker may be MKIIEQLPSA (SEQ ID NO: 14), VRHKLKRVGS (SEQ ID NO: 15), VPFLLEPDNINGKTC (SEQ ID NO: 16), GHGTGSTGSGSS (SEQ ID NO: 17), MSRPDPA (SEQ ID NO: 18), GSAGSAAGSGEF (SEQ ID NO: 19), SGSETPGTSESA (SEQ ID NO: 20), SGSETPGTSESATPES (SEQ ID NO: 21), or GSKDHILQFVIPNRLVKSELEEK (SEQ ID NO: 54). The linker may comprise portions, combinations or combinations of portions of any of the linkers described above.

Where a polypeptide component of the gene editing system also comprises an NLS, e.g., as described below, optionally any of the linkers suitable for linking two polypeptide components together, e.g., as described above, may also be used to link one or more NLS domains to any other polypeptide component of the system.

NLS

While not wishing to be bound by theory, it may also be beneficial to include a nuclear localization sequence (NLS) in any polypeptide-based component of the gene editing systems described herein. In some embodiments, each polypeptide-based component of the gene editing system comprises one or more nuclear localization sequences (NLSs), such as about or more than about 1, 2, 3, 4, 5, 6, 7, 8, 9, 10, or more NLSs. In some embodiments, any polypeptide component of the gene editing system comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, but other types of NLS are known. Non-limiting examples of NLSs include an NLS sequence comprising or derived from: the NLS of the SV40 virus large T-antigen, having the amino acid sequence PKKKRKV (SEQ ID NO: 22); the NLS from nucleoplasmin (e.g. the nucleoplasmin bipartite NLS with the sequence KRPAATKKAGQAKKKK (SEQ ID NO: 23)); the c-myc NLS having the amino acid sequence PAAKRVKLD (SEQ ID NO: 24) or RQRRNELKRSP (SEQ ID NO: 25); the hRNPA1 M9 NLS having the sequence NQSSNFGPMKG-GNFGGRSSGPYGGGGQYFAKPRNQGGY (SEQ ID NO: 26); the sequence RMRIZFKNKGKDTAELRRRRVEVS-VELRKAKKDEQILKRRNV (SEQ ID NO: 27) of the IBB domain from importin-alpha; the sequences VSRKRPRP (SEQ ID NO: 28) and PPKKARED (SEQ ID NO: 29) of the myoma T protein; the sequence PQPKKKPL (SEQ ID NO: 30) of human p53; the sequence SALIKKKKMAP (SEQ ID NO: 31) of mouse c-abl IV; the sequences DRLRR (SEQ ID NO: 32) and PKQKKRK (SEQ ID NO: 33) of the influenza virus NS1; the sequence RKLKKKIKKL (SEQ ID NO: 34) of the Hepatitis virus delta antigen; the sequence REKK-KFLKRR (SEQ ID NO: 35) of the mouse Mx1 protein; the sequence KRKGDEVDGVDEVAKKKSKK (SEQ ID NO: 36) of the human poly(ADP-ribose) polymerase; and the sequence RKCLQAGMNLEARKTKK (SEQ ID NO: 37) of the steroid hormone receptors (human) glucocorticoid. Other suitable NLS sequences are known in the art (e.g., Sorokin, *Biochemistry (Moscow)* (2007) 72:13, 1439-1457; Lange *J Biol Chem.* (2007) 282:8, 5101-5).

Fusion Proteins:

Any of the following polypeptides (i.e., polypeptides comprising a guide RNA-binding domain, optionally a linker, and a nuclease domain) may be used, optionally with one or more NLS sequences, e.g., as described above, in the gene editing systems of the present invention:

```
>catalyticFOK1_(G4S)2_8xHis
                                    (SEQ ID NO: 55)
KSELREIKLKYVPHEYIELIEIARNSTQDRILEMKVMEFFMKVYGYR

GKHLGGSRKPDGAIYTVGSPIDYGVIVDTKAYSGGYNLPIGQADEMQ
```

RYVEENQTRNKHINPNEWWKVYPSSVTEFKFLFVSGHFKGNYKAQLT

RLNHITNCNGAVLSVEELLIGGEMIKAGTLTLEEVRRKENNGEINFG

GGGSGGGGSHHHHHHHH

>8XHis_(G4S)2_catalyticFOK1
(SEQ ID NO: 56)
RGSHHHHHHHHGGGGSGGGGSKSELRHKLKYVPHEYIELIEIARNST

QDRILEMKVMEFFMKVYGYRGKHLGGSRKPDGAIYTVGSPIDYGVIV

DTKAYSGGYNLPIGQADEMQRYVEENQTRNKHINPNEWWKVYPSSVT

EFKFLFVSGHFKGNYKAQLTRLNHITNCNGAVLSVEELLIGGEMIKA

GTLTLEEVRRKFNNGEINF

>8XHis_Fox1linker_catalyticFOK1
(SEQ ID NO: 57)
RGSHHHHHHHHGSKDHILQFVIPNRLVKSELEEKKSELRHKLKYVPH

EYIELIEIARNSTQDRILEMKVMEFFMKVYGYRGKHLGGSRKPDGAI

YTVGSPIDYGVIVDTKAYSGGYNLPIGQADEMQRYVEENQTRNKHIN

PNEWWKVYPSSVTEFKFLFVSGHFKGNYKAQLTRLNHITNCNGAVLS

VEELLIGGEMIKAGTLTLEEVRRKFNNGEINF

Where any of the above polypeptides is used, the guide RNA may comprise, e.g., consist of SEQ ID NO: 8.
Alternatively, any of the following polypeptides (i.e., polypeptides comprising a guide RNA-binding domain, optionally a linker, and a nuclease domain) may be used, optionally with one or more NLS sequences, e.g., as described above, in the gene editing systems of the present invention:

>catalyticFOK1_(G4S)2_lysozyme
(SEQ ID NO: 58)
KSELREIKLKYVPHEYIELIEIARNSTQDRILEMKVMEFFMKVYGYR

GKHLGGSRKPDGAIYTVGSPIDYGVIVDTKAYSGGYNLPIGQADEMQ

RYVEENQTRNKHINPNEWWKVYPSSVIEFKFLFVSGEFKGNYKAQLT

RLNHITNCNGAVLSVEELLIGGEMIKAGTLTLEEVRRKFNNGEINFG

GGGSGGGGSKVFERCELARTLKRLGMDGYRGISLANWMCLAKWESGY

NTRATNYNAGDRSTDYGIFQINSRYWCNDGKTPGAVNACHLSCSALL

QDNIADAVACAKRVVRDPQGIRAWVAWRNRCQNRDVRQYVQGCGV

>Lysozyme_(G4S)2_catalyticFOK1
(SEQ ID NO: 59)
KVFERCELARTLKRLGMDGYRGISLANWMCLAKWESGYNTRATNYNA

GDRSTDYGIFQINSRYWCNDGKTPGAVNACHLSCSALLQDNIADAVA

CAKRVVRDPQGIRAWVAWRNRCQNRDVRQYVQGCGVGGGGSGGGGSK

SELRHKLKYVPHEYIELIEIARNSTQDRILEMKVMEFFMKVYGYRGK

HLGGSRKPDGAIYTVGSPIDYGVIVDTKAYSGGYNLPIGQADEMQRY

VEENQTRNKHINPNEWWKVYPSSVTEFKFLFVSGHFKGNYKAQLTRL

NHITNCNGAVLSVEELLIGGEMIKAGTLTLEEVRRKFNNGEINF

>lysozyme_Fox1linker_catalyticFOK1
(SEQ ID NO: 60)
KVFERCELARTLKRLGMDGYRGISLANWMCLAKWESGYNTRATNYNA

GDRSTDYGIFQINSRYWCNDGKTPGAVNACHLSCSALLQDNIADAVA

CAKRVVRDPQGIRAWVAWRNRCQNRDVRQYVQGCGVGSKDHILQFVI

PNRLVKSELEEKKSELRHKLKYVPHEYIELIEIARNSTQDRILEMKV

MEFFMKVYGYRGKHLGGSRKPDGAIYTVGSPIDYGVIVDTKAYSGGY

NLPIGQADEMQRYVEENQTRNKHINPNEWWKVYPSSVTEFKFLFVSG

HFKGNYKAQLTRLNHITNCNGAVLSVEELLIGGEMIKAGTLTLEEVR

RKFNNGEINF

Where any of the above polypeptides is used, the guide RNA may comprise, e.g., consist of SEQ ID NO: 3.

Target Sequence, e.g., Target DNA Sequence

In one aspect, the invention provides methods for using the gene editing system or one or more of its components. The gene editing system of the invention provides an effective means for modifying a target polynucleotide, e.g., a target DNA sequence. The gene editing system of the invention has a wide variety of utility including modifying (e.g., deleting, inserting, translocating, inactivating, activating) a target polynucleotide in a multiplicity of cell types. As such the gene editing system of the invention has a broad spectrum of applications in, e.g., gene therapy, drug screening, disease diagnosis, and prognosis.

The target polynucleotide of a gene editing system (e.g., the target of the targeting RNA) can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

In preferred embodiments, the target DNA sequence is a sequence that is actively transcribed, e.g., actively transcribed in the cell type being studied. In embodiments, the target DNA sequence is a sequence that does not comprise condensed chromatin, e.g., does not comprise condensed chromatin in the cell type being studied. Without being bound by theory, it is believed that target DNA sequences that are actively transcribed will have increased accessibility, e.g., increased accessibility for hybridization by the targeting domain of the RNA molecule of the invention, relative to sequences that are not actively transcribed, e.g., such as condensed chromatin.

The target polynucleotide of a gene editing system of the present invention may include a number of disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web. Such genes, proteins and pathways may be the target polynucleotide of a gene editing system of the present invention.

In some aspects, a gene editing system, e.g., as described herein, can be used to create an allogeneic immune cell, e.g., a T-cell or NK cell, e.g., an allogeneic immune cell lacking expression of a functional T cell receptor (TCR) and/or human leukocyte antigen (HLA), e.g., HLA class I and/or HLA class II.

In some aspects, a gene editing system, e.g., as described herein, can be used to create a T cell lacking a functional TCR, e.g., engineered such that it does not express any functional TCR on its surface, such that it does not express one or more subunits, e.g., a TCRα and/or TCRβ that comprise a functional TCR, or such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

In some aspects, a gene editing system, e.g., as described herein, can be used to engineer a T cell such that it does not express a functional HLA on its surface, or where cell surface expression of HLA, e.g., HLA class I and/or HLA class II, is downregulated. For example, a gene editing system of the present invention comprising one or more (e.g., two) nucleic acids comprising targeting RNA that is complimentary to nucleic acid sequence of an HLA gene and further comprise a guide RNA, and the gene editing system further comprising one or more (e.g., two) polypeptides comprising a guide RNA-binding domain and a cleavage domain can be introduced into a cell such that the HLA gene is inactivated, e.g., by cleaving and non-homologous end joining.

In some aspects, two or more gene editing systems, e.g., as described herein, can be used to regulate expression of two or more genes. In one aspect, two gene editing systems are used to regulate, e.g., inhibit, expression of both a functional TCR and a functional HLA, e.g., HLA class I and/or HLA class II.

In some aspects, a gene editing system, e.g., as described herein, can be used to regulate, e.g., downregulate, inhibit or repress expression of an inhibitory molecule. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. Inhibition of an inhibitory molecule in a cell, e.g., with the use of a gene editing system as described herein, can improve the function of the cell.

In some aspects, a gene editing system, e.g., as described herein, can be used to modulate or modify expression of beta 2-microglobulin (BSM).

In some aspects, a gene editing system, e.g., as described herein, can be used to modulate or modify expression of BCL11a, or a BCL11a negative repressor binding site. In other aspects, a gene editing system, e.g., as described herein, can be used to modulate or modify expression of a globin gene, e.g., beta-globin or gamma-globin, e.g., a beta-globin or gamma-globin gene bearing a mutation associated with a disease.

In some aspects, a gene editing system, e.g., as described herein, (or nucleic acid encoding said gene editing system, or cell comprising said gene editing system, e.g., as described herein) is used to treat a disorder associated with aberrant gene expression, e.g., a cancer or a genetic disorder. Examples of cancers that may be treated with the compositions of the present invention include breast cancer, colorectal cancer, lung cancer, multiple myeloma, ovarian cancer, liver cancer, gastric cancer, pancreatic cancer, acute myeloid leukemia, chronic myeloid leukemia, osteosarcoma, squamous cell carcinoma, peripheral nerve sheath tumors schwannoma, head and neck cancer, bladder cancer, esophageal cancer, Barretts esophageal cancer, glioblastoma, clear cell sarcoma of soft tissue, malignant mesothelioma, neurofibromatosis, renal cancer, melanoma, prostate cancer, benign prostatic hyperplasia (BPH), gynacomastica, and endometriosis. Examples of genetic disorders are described on the website of the National Institutes of Health under the topic subsection Genetic Disorders (website at health.nih.gov/topic/GeneticDisorders). Other examples include ocular defects caused by genetic mutations, including those described in Genetic Diseases of the Eye, Second Edition, edited by Elias I. Traboulsi, Oxford University Press, 2012. Preferably the genetic disorder is selected from the group consisting of epidermolysis bullosa, recessive dystrophic epidermolysis bullosa (RDEB), osteogenesis imperfecta, dyskeratosis congenital, a mucopolysaccharidosis, muscular dystrophy, cystic fibrosis (CFTR), fanconi anemia, a sphingolipidosis, a lipofuscinosis, adrenoleukodystrophy, severe combined immunodeficiency, sickle-cell anemia and thalassemia.

In some aspects, a gene editing system, e.g., as described herein, (or nucleic acid encoding said gene editing system, or cell comprising said gene editing system, e.g., as described herein) is used to treat a lysosomal storage disorder. Examples of liposomal storage disorders include Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders, e.g., Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV; Multiple sulfatase deficiency, Niemann-Pick Disease, Neuronal Ceroid Lipofuscinoses, CLN6 disease, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis, Pompe disease/Glycogen storage disease type II, Pycnodysostosis, Sandhoff disease/Adult Onset/GM2 Gangliosidosis, Schindler disease, Salla disease/Sialic Acid Storage Disease, Tay-Sachs/GM2 gangliosidosis, and Wolman disease Regulatable Systems In some embodiments, a regulatable gene editing system where the activity of the gene editing system can be controlled is desirable to optimize the safety and efficacy of a gene editing system. There are many ways gene editing system activities can be regulated. Such systems are referred to herein as regulatable gene editing systems.

In one embodiment, the polypeptide based component of the gene editing systems of the present invention may further comprise an intein, e.g., a 4-hydroxytamoxifen-responsive intein, e.g., as described in Davis et al., *Nature Chem. Biol.*, vol. 11, pp. 316-319 (2015), which is hereby incorporated by reference. An intein may be incorporated into the sequence of the guide RNA-binding domain and/or the cleavage domain. Without intending to be bound by theory, it is believed that incorporation of the intein would block the binding of a guide RNA to a guide RNA-binding domain, or would block the binding and/or activity of the cleavage domain. Addition of a small molecule (e.g., 4-hydroxytomoxifen in the case of a 4-hydroxytamoxifen-responsive intein) causes the intein to be spliced out, thereby rescuing activity. In such embodiments the small molecule turns the system "on."

In other embodiment, for example, inducible apoptosis using, e.g., a caspase fused to a dimerization domain (see, e.g., Di Stasa et al., *N Engl. J. Med.* 2011 Nov. 3; 365(18): 1673-1683), can be used as a safety switch in the cells comprising the gene editing systems of the instant invention. In one embodiment, the cells (e.g., T cells or NK cells) expressing or comprising a gene editing system of the present invention further comprise an inducible apoptosis switch, wherein a human caspase (e.g., caspase 9) or a modified version is fused to a modification of the human FKB protein that allows conditional dimerization. In the presence of a small molecule, such as a rapalog (e.g., AP1903, AP20187), the inducible caspase (e.g., caspase 9) is activated and leads to the rapid apoptosis and death of the cells (e.g., T cells or NK cells) expressing or comprising a gene editing system of the present invention. Examples of a caspase-based inducible apoptosis switch (or one or more aspects of such a switch) have been described in, e.g., US2004040047; US20110286980; US20140255360; WO1997031899; WO2014151960; WO2014164348; WO2014197638; WO2014197638; all of which are incorporate by reference herein.

In another aspect, the regulatable gene editing system comprises a set of polypeptide-based components, typically two in the simplest embodiments, in which the components of a standard gene editing system described herein, e.g., a guide RNA-binding domain and a cleavage domain, are partitioned on separate polypeptides or members. In some embodiments, the set of polypeptides include a dimerization switch that, upon the presence of a dimerization molecule, can couple the polypeptides to one another, e.g., can couple a guide RNA-binding domain to a cleavage domain. In one embodiment, the CARs of the present invention utilizes a dimerization switch such as those described in, e.g., WO2014127261, which is incorporated by reference herein.

Nucleic Acids and Vectors

Nucleic acid sequences encoding one or more gene editing system molecule, e.g., nucleic acid or polypeptide, described herein, can be obtained using standard synthetic and/or recombinant techniques. Desired nucleic acid sequences may be isolated and sequenced from appropriate source cells or can be synthesized using nucleotide synthesizer or PCR techniques.

The expression of natural or synthetic nucleic acids encoding one or more gene editing system molecule described herein is typically achieved by operably linking a nucleic acid encoding the nucleic acid and/or polypeptide components of the gene editing system, or portions thereof, to a promoter, and incorporating the construct into an expression vector. The vectors can be suitable for replication and integration in eukaryotes. Typical cloning vectors contain transcription and translation terminators, initiation sequences, and promoters useful for regulation of the expression of the desired nucleic acid sequence. The expression of the components of the gene editing system may be driven by one or more polymerase III promoters, one or more polymerase II promoters, one or more polymerase I promoters, or combinations thereof. Examples of polymerase III promoters include, but are not limited to, U6 and H1 promoters. Examples of polymerase II promoters include, but are not limited to, the retroviral Rous sarcoma virus (RSV) LTR promoter (optionally with the RSV enhancer), the cytomegalovirus (CMV) promoter (optionally with the CMV enhancer) see, e.g., Boshart et al, *Cell,* 41:521-530 (1985), the SV40 promoter, the dihydrofolate reductase promoter, the β-actin promoter, the phosphoglycerol kinase (PGK) promoter, and the EF1α promoter.

In some embodiments, bi- or tri-cistronic vectors may also be constructed making use of internal ribosomal entry sites (IRES) such as for example the element from the encephalomyocarditis virus (EMCV) or EV71 for translation of two or more open reading frames (ORFs). Such vectors are designed to drive transcription of the bi- or tri-cistronic message under control of a strong human promoter regulatory region e.g. CMV or EF1alpha. IRESs are relatively short DNA sequences that can initiate RNA translation in a 5' cap-independent fashion. Whereas the first cistron is translated in a cap-dependent manner driven by a strong mammalian promoter, the subsequent ones utilize intercistronic regions of viral origin such as the internal ribosomal entry site of poliovirus or the cap-independent translation enhancer of encephalomyocarditis virus for enhanced translation. (N Chinnasamy et al. (2009), Production of Multicistronic HIV-1 Based Lentiviral Vectors; Methods Mol Biol 515: 1-14).

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter (EF1a), the hemoglobin promoter, and the creatine kinase promoter. Further, embodiments are not limited to the use of constitutive promoters. Embodiments comprise inducible promoters. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In embodiments, the nucleic acid encoding one or more components of the gene editing system may comprise nucleic acid sequence encoding a furin domain.

In an embodiment, (i) sequence encoding a first polypeptide-based component of a gene editing system, e.g., a polypeptide comprising a first cleavage domain and (ii) sequence encoding a second polypeptide-based component of a gene editing system, e.g., a polypeptide comprising a second cleavage domain, are present on a single nucleic acid molecule, are transcribed as a single transcription product, and are configured as follows:

a promoter, e.g., a promoter described herein, e.g., an EF1alpha promoter, is operably linked to (i), (ii), and to (iii) sequence encoding an IRES, e.g., an EMCV or EV71 IRES. In an embodiment (iii) is disposed between (i) and (ii). In an embodiment, (i), (ii), and (iii) are transcribed as a single RNA. In an embodiment, the order, on the nucleic acid, is (i)-(iii)-(ii). In an embodiment, the order, on the nucleic acid, is (ii)-(iii)-(i).

In an embodiment, (i) sequence encoding a first polypeptide-based component of a gene editing system, e.g., a polypeptide comprising a first cleavage domain and (ii) sequence encoding a second polypeptide-based component of a gene editing system, e.g., a polypeptide comprising a second cleavage domain, are present on a single nucleic acid molecule, are transcribed as a single transcription product, and are configured as follows:

a promoter, e.g., a promoter described herein, e.g., an EF1alpha promoter, is operably linked to (i), (ii), and to (iii) sequence encoding a furin domain, e.g., a furin domain as described herein. In an embodiment (iii) is disposed between (i) and (ii). In an embodiment, (i), (ii), and (iii) are transcribed as a single RNA. In an embodiment, the order, on the nucleic acid, is (i)-(iii)-(ii). In an embodiment, the order, on the nucleic acid, is (ii)-(iii)-(i).

The nucleic acid can be cloned into a number of types of vectors. For example, the nucleic acid can be cloned into a vector including, but not limited to a plasmid, a phagemid, a phage derivative, an animal virus, a cosmid, a minicircle, a nanoplasmid, and a nanocircle. In one aspect, the the vector comprising the nucleic acid encoding the gene editing system of the invention is a DNA, a RNA, a plasmid, a minicircle, an adenoviral vector, an adeno-associated virus vector, a lentivirus vector, or a retrovirus vector.

Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. Selection of an appropriate vector will depend mainly on the size of the nucleic acids to be inserted into the vector and the particular host cell to be transformed with the vector. Each vector contains various components, depending on its function (amplification or expression of heterologous nucleic acid sequence, or both) and its compatibility with the particular host cell in which it resides. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193). Other elements that may be included in the vector include a ribosomal binding site, a signal sequence, a transcriptional termination site, a tag, and a reporter gene.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to desired host cells, or cells of the subject, either in vivo or ex vivo. A number of retroviral systems are known in the art. In some aspects, adenovirus vectors are used. A number of adenovirus vectors are known in the art. In one aspect, adeno-associated virus (AAV) vector, e.g., an AAV2, AAV3, AAV4, AAV5, AAV6, AAV7, AAV8, or AAV9 vector, or any modified vectors thereof. In one aspect, lentivirus vectors are used.

Expression in Cells

The present invention provides gene editing systems useful in engineering cells to, and in applications involving the use of such engineered cells. The cells may be eurkaryote cells, e.g., insect, worm or mammalian cells. Suitable mammalian cells include, but are not limited to, equine, bovine, ovine, canine, feline, murine, non-human primate cells, and human cells.

Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Other cells for use in the present invention include stem and progenitor cells, such as hematopoietic, neural, stromal, muscle, hepatic, pulmonary, gastrointestinal and mesenchymal stem or progenitor cells. In some aspects using hematopoietic cells, the hematopoietic cells may include any of the nucleated cells which may be involved with the erythroid, lymphoid or myelomonocytic lineages, as well as myoblasts and fibroblasts, and immune effector cells, e.g., T cells and NK cells. The cells may be autologous cells, syngeneic cells, allogeneic cells and even in some cases, xenogeneic cells with respect to an intended host organism.

In one aspect, the components of the gene editing systems of the present invention may be introduced directly into a cell. For example, the RNA-based components (e.g. RNA comprising a targeting RNA and a guide RNA domain) and the polypeptide-based components (e.g., polypeptide comprising a guide RNA-binding domain and a cleavage domain) can be pre-complexed, e.g., complexed in vitro, to form a ribonuclear protein (RNP). The RNP may be introduced into the cell by known techniques, for example, electroporation.

In one aspect, the components of the gene editing systems of the present invention may be introduced directly into a cell as separate compositions. For example, the RNA-based components may be directly introduced and the polypeptide-based components may be directly introduced.

In one aspect, the RNA based components of the gene editing system may be directly introduced into a cell and the polypeptide-based components of the gene editing system may be expressed within the cell, e.g., by introduction of nucleic acid encoding said polypeptide-based components.

In one aspect, the polypeptide-based components of the gene editing system may be directly introduced into a cell and the RNA-based components of the gene editing system may be expressed within the cell, e.g., by introduction of nucleic acid encoding said RNA-based components.

In one aspect, the cell may be made to express both the RNA-based components of the gene editing system and the polypeptide-based components of the gene editing system, e.g., by introduction of nucleic acid encoding said RNA-based components and polypeptide-based components.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a nucleic acid into a host cell include calcium phosphate precipitation, lipofection, particle bombardment, microinjection, electroporation, squeezing and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is lipofection, e.g., using Lipofectamine (Life Technologies).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In some aspects, host cells can be modified ex vivo with a nucleic acid, e.g., vector, comprising a gene editing system described herein. Cells which have been modified ex vivo with the vector may be grown in culture under selective conditions and cells which are selected as having the desired construct(s) may then be expanded and further analyzed, using, for example, the polymerase chain reaction for determining the presence of the construct in the host cells and/or assays for the production of the desired gene product(s). Once modified host cells have been identified, they may then be used as planned, e.g. grown in culture or introduced into a host organism.

Depending upon the nature of the cells, the cells may be introduced into a host organism, e.g. a mammal, e.g., a human, in a wide variety of ways. Hematopoietic cells may be administered by injection into the vascular system, there being usually at least about $10^4$ cells and generally not more than about $10^{10}$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Generally, for myoblasts or fibroblasts for example, the number of cells will be at least about $10^4$ and not more than about $10^9$ and may be applied as a dispersion, generally being injected at or near the site of interest. The cells will usually be in a physiologically-acceptable medium. Cells engineered in accordance with this invention may also be encapsulated, e.g. using conventional biocompatible materials and methods, prior to implantation into the host organism or patient for the production of a therapeutic protein.

In other aspects, the cells can be engineered to express the gene editing system molecules in vivo. For this purpose, various techniques have been developed for modification of target tissue and cells in vivo. A number of viral vectors have been developed, such as adenovirus, adeno-associated virus, lentivirus, and retroviruses, as discussed above, which allow for transfection and, in some cases, integration of the virus into the host. See, for example, Dubensky et al. (1984) Proc. Natl. Acad. Sci. USA 81, 7529-7533; Kaneda et al., (1989) Science 243, 375-378; Hiebert et al. (1989) Proc. Natl. Acad. Sci. USA 86, 3594-3598; Hatzoglu et al. (1990) J. Biol. Chem. 265, 17285-17293 and Ferry, et al. (1991) Proc. Natl. Acad. Sci. USA 88, 8377-8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used.

In accordance with in vivo genetic modification, the manner of the modification will depend on the nature of the tissue, the efficiency of cellular modification required, the number of opportunities to modify the particular cells, the accessibility of the tissue to the nucleic acid, e.g., vector, composition to be introduced, and the like. Nucleic acid introduction need not result in integration. In some situations, transient maintenance of the introduced nucleic acids described herein may be sufficient. In this way, one could have a short term effect, where cells could be introduced into the host and then turned on after a predetermined time, for example, after the cells have been able to home to a particular site.

Pharmaceutical Compositions and Treatments

Pharmaceutical compositions may comprise gene editing system molecules, e.g., the polypeptide and nucleic acid components of the gene editing system, or nucleic acid encoding the components of the gene editing system, e.g., a vector encoding the gene editing system molecules, or a cell comprising the gene editing system molecules, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In an aspect, the pharmaceutical compositions are formulated for intravenous administration.

Pharmaceutical compositions may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-cancer effective amount," "a cancer-inhibiting effective amount," or "therapeutic amount" is indicated, the precise amount of the compositions to be administered can be determined by a physician with consideration of individual differences in age, weight, disease state, e.g., tumor size, extent of infection or metastasis, and condition of the patient (subject). Compositions may also be administered multiple times at these dosages. The optimal dosage and treatment regime for a particular patient can be determined by one skilled in the art of medicine by monitoring the patient for signs of disease and adjusting the treatment accordingly.

Additional Embodiments

1. A non-naturally occurring gene editing system comprising:
a) nucleic acid comprising a first targeting RNA capable of hybridizing with a target DNA sequence;
b) nucleic acid comprising a first guide RNA capable of binding to a first guide RNA-binding domain, and
c) a polypeptide comprising the first guide RNA-binding domain and a first cleavage domain,
wherein the polypeptide of c) comprises fewer than approximately 1200 amino acids.

2. The non-naturally occurring gene editing system of embodiment 1, wherein the polypeptide of c) comprises fewer than approximately 1100 amino acids.

3. The non-naturally occurring gene editing system of embodiment 1, wherein the polypeptide of c) comprises fewer than approximately 1000 amino acids.

4. The non-naturally occurring gene editing system of embodiment 1, wherein the polypeptide of c) comprises fewer than approximately 900 amino acids.

5. The non-naturally occurring gene editing system of embodiment 1, wherein the polypeptide of c) comprises fewer than approximately 800 amino acids.

6. The non-naturally occurring gene editing system of embodiment 1, wherein the polypeptide of c) comprises fewer than approximately 700 amino acids.

7. The non-naturally occurring gene editing system of embodiment 1, wherein the polypeptide of c) comprises fewer than approximately 600 amino acids.

8. The non-naturally occurring gene editing system of embodiment 1, wherein the polypeptide of c) comprises fewer than approximately 500 amino acids.

9. The non-naturally occurring gene editing system of embodiment 1, wherein the polypeptide of c) comprises fewer than approximately 400 amino acids.

10. The non-naturally occurring gene editing system of embodiment 1, wherein the polypeptide of c) comprises fewer than approximately 300 amino acids.

11. The non-naturally occurring gene editing system of embodiment 1, wherein the polypeptide of c) comprises fewer than approximately 200 amino acids.

12. The non-naturally occurring gene editing system of any of the preceding embodiments, wherein the nucleic acid of a) and the nucleic acid of b) are disposed on separate nucleic acid molecules.

13. The non-natural occurring gene editing system of any of embodiments 12, wherein the nucleic acid of a) further comprises a hybridization domain A and the nucleic acid of b) further comprises a hybridization domain A', and wherein said hybridization domain A and hybridization domain A' are capable of specific hybridization.

14. The non-naturally occurring gene editing system of embodiment 13, wherein the hybridization domain A and the hybridization domain A' each comprise 10-50 complimentary nucleic acid residues, e.g., 20-40, e.g., 20, 21, 22, 23, 24, 25, 26, 27, 28, 29, 30, 31, 32, 33, 34, 35, 36, 37, 38, 39 or 40 nucleic acid residues.

15. The non-naturally-occurring gene editing system of any of embodiments 1-11, wherein the nucleic acid of a) and the nucleic acid of b) are disposed on the same molecule.

16. The non-naturally occurring gene editing system of any of the preceding embodiments, wherein the first guide RNA-binding domain is lysozyme, e.g., SEQ ID NO: 2, SEQ ID NO: 50, or an RNA binding fragment or analog thereof.

17. The non-naturally occurring gene editing system of embodiment 16, wherein the first guide RNA comprises SEQ ID NO: 3.

18. The non-naturally occurring gene editing system of any of embodiments 1-15, wherein the first guide RNA-binding domain is a fibronectin.

19. The non-naturally occurring gene editing system of any of embodiments 1-15, wherein the first guide RNA-binding domain is an antibody or antigen-binding fragment or analog thereof.

20. The non-naturally occurring gene editing system of embodiment 19, wherein the first guide RNA-binding domain is an antibody or antigen-binding fragment or analog thereof is an IgE-derived antibody or antigen-binding fragment or analog thereof, and the first guide RNA comprises SEQ ID NO: 11.

21. The non-naturally occurring gene editing system of any of embodiments 1-15, wherein the first guide RNA-binding domain is a fluorescent protein or functional fragment thereof, e.g., is selected from the group consisting of the proteins identified in Tables 1-4, and an RNA-binding fragment or analog of any of the preceding.

22. The non-naturally occurring gene editing system of embodiment 21, wherein the first guide RNA comprises SEQ ID NO: 10.

23. The non-naturally occurring gene editing system of any of the preceding embodiments, wherein the first cleavage domain comprises a functional fragment of a nuclease capable of inducing a double-strand break in DNA.

24. The non-naturally occurring gene editing system of embodiment 23, wherein the first cleavage domain comprises a functional fragment of a GIY-YIG homing endonuclease.

25. The non-naturally occurring gene editing system of embodiment 24, wherein the first cleavage domain comprises a functional fragment of I-TevI, e.g., a functional fragment of SEQ ID NO: 13.

26. The non-naturally occurring gene editing system of any of embodiments 1-22, wherein the first cleavage domain comprises a functional fragment of a nuclease capable of inducing a single-strand break in DNA.

27. The non-naturally occurring gene editing system of embodiment 26, wherein the first cleavage domain comprises a functional fragment of a nuclease selected from the group consisting of FokI and PvuII, e.g., SEQ ID NO: 12 or a functional fragment thereof, or SEQ ID NO: 49 or a functional fragment thereof.

28. The non-naturally occurring gene editing system of any of the preceding embodiments, further comprising d) nucleic acid comprising a second targeting RNA capable of hybridizing with a second target DNA sequence, e) nucleic acid comprising a second guide RNA capable of binding to the first guide RNA-binding domain or a second guide-RNA-binding domain, and, optionally, f) a polypeptide comprising the second guide RNA-binding domain and a second cleavage domain, wherein the polypeptide of f) comprises fewer than approximately 1200 amino acids.

29. The non-naturally occurring gene editing system of embodiment 28, wherein the polypeptide of f) comprises fewer than approximately 1100 amino acids.

30. The non-naturally occurring gene editing system of embodiment 28, wherein the polypeptide of f) comprises fewer than approximately 1000 amino acids.

31. The non-naturally occurring gene editing system of embodiment 28, wherein the polypeptide of f) comprises fewer than approximately 900 amino acids.

32. The non-naturally occurring gene editing system of embodiment 28, wherein the polypeptide of f) comprises fewer than approximately 800 amino acids.

33. The non-naturally occurring gene editing system of embodiment 28, wherein the polypeptide of f) comprises fewer than approximately 700 amino acids.

34. The non-naturally occurring gene editing system of embodiment 28, wherein the polypeptide of f) comprises fewer than approximately 600 amino acids.

35. The non-naturally occurring gene editing system of embodiment 28, wherein the polypeptide of f) comprises fewer than approximately 500 amino acids.

36. The non-naturally occurring gene editing system of embodiment 28, wherein the polypeptide of f) comprises fewer than approximately 400 amino acids.

37. The non-naturally occurring gene editing system of embodiment 28, wherein the polypeptide of f) comprises fewer than approximately 300 amino acids.

38. The non-naturally occurring gene editing system of embodiment 28, wherein the polypeptide of f) comprises fewer than approximately 200 amino acids.

39. The non-naturally occurring gene editing system of any of embodiments 28-38, wherein the nucleic acid of d) and the nucleic acid of e) are disposed on separate nucleic acid molecules.

40. The non-natural occurring gene editing system of embodiment 39, wherein the nucleic acid of d) further comprises a hybridization domain B and the nucleic acid of e) further comprises a hybridization domain B', and wherein said hybridization domain B and hybridization domain B' are capable of specific hybridization.

41. The non-naturally occurring gene editing system of embodiment 40, wherein the hybridization domain B and the hybridization domain B' each comprise 10-50 complimentary nucleic acid residues, e.g., 20-40, e.g., 20, 21, 22, 23, 24, 25, 26, 27, 28, 29, 30, 31, 32, 33, 34, 35, 36, 37, 38, 39 or 40 nucleic acid residues.

42. The non-naturally-occurring gene editing system of any of embodiments 28-38, wherein the nucleic acid of d) and the nucleic acid of e) are disposed on the same molecule.

43. The non-naturally occurring gene editing system of any of embodiments 28-42, wherein the first guide RNA and the second guide RNA comprise different sequences.

44. The non-naturally occurring gene editing system of any of embodiments 28-42, wherein the first guide RNA and the second guide RNA comprise the same sequence.

45. The non-naturally occurring gene editing system of any of embodiments 28-44, wherein the first guide RNA and the second guide RNA each independently bind to the first guide RNA-binding domain.

46. The non-naturally occurring gene editing system of embodiment 45, wherein the first guide RNA-binding domain comprises sequence selected from the group consisting of lysozyme, a fibronectin, an antibody or antigen-binding fragment or analog thereof, and a fluorescent protein or functional fragment or analog thereof.

47. The non-naturally occurring gene editing system of embodiment 46, wherein the first and second guide RNA each comprise SEQ ID NO: 3 and the first guide RNA-binding domain comprises lysozyme, e.g., SEQ ID NO: 2 or SEQ ID NO: 50 or a guide RNA-binding fragment thereof.

48. The non-naturally occurring gene editing system of embodiment 46, wherein the first and second guide RNA each comprise SEQ ID NO: 11 and the first guide RNA-binding domain comprises an IgE antibody or an antigen binding fragment or analog thereof.

49. The non-naturally occurring gene editing system of embodiment 46, wherein the first and second guide RNA each comprise SEQ ID NO: 10 and the first guide RNA-binding domain comprises a fluorescent protein or an active fragment thereof, e.g., is selected from the group consisting of the proteins identified in Tables 1-4, and an RNA-binding fragment or analog of any of the preceding.

50. The non-naturally occurring gene editing system of any of embodiments 28-42, wherein the first guide RNA binds specifically to the first guide RNA-binding domain and the second guide RNA binds specifically to the second guide RNA-binding domain.

51. The non-naturally occurring gene editing system of embodiment 50, wherein the first guide RNA-binding domain and the second guide RNA-binding domain are independently selected from the group consisting of: lysozyme, a fibronectin, an antibody or antigen-binding fragment or analog thereof, and a fluorescent protein or functional fragment or analog thereof, with the proviso that the first guide RNA-binding domain and the second guide RNA-binding domain are not identical.

52. A non-naturally occurring gene editing system comprising: a) nucleic acid comprising a first targeting RNA capable of hybridizing with a target DNA sequence, b) nucleic acid comprising a first guide RNA capable of binding directly to a first cleavage domain, and c) a polypeptide comprising the first cleavage domain, wherein the polypeptide of c) comprises fewer than approximately 1200 amino acids.

53. The non-naturally occurring gene editing system of embodiment 28, wherein the polypeptide of c) comprises fewer than approximately 1100 amino acids.

54. The non-naturally occurring gene editing system of embodiment 28, wherein the polypeptide of c) comprises fewer than approximately 1000 amino acids.

55. The non-naturally occurring gene editing system of embodiment 28, wherein the polypeptide of c) comprises fewer than approximately 900 amino acids.

56. The non-naturally occurring gene editing system of embodiment 28, wherein the polypeptide of c) comprises fewer than approximately 800 amino acids.

57. The non-naturally occurring gene editing system of embodiment 28, wherein the polypeptide of c) comprises fewer than approximately 700 amino acids.

58. The non-naturally occurring gene editing system of embodiment 28, wherein the polypeptide of c) comprises fewer than approximately 600 amino acids.

59. The non-naturally occurring gene editing system of embodiment 28, wherein the polypeptide of c) comprises fewer than approximately 500 amino acids.

60. The non-naturally occurring gene editing system of embodiment 28, wherein the polypeptide of c) comprises fewer than approximately 400 amino acids.

61. The non-naturally occurring gene editing system of embodiment 28, wherein the polypeptide of c) comprises fewer than approximately 300 amino acids.

62. The non-naturally occurring gene editing system of embodiment 28, wherein the polypeptide of c) comprises fewer than approximately 200 amino acids.

63. The non-naturally occurring gene editing system of any of embodiments 52-62, wherein the nucleic acid of a) and the nucleic acid of b) are disposed on separate nucleic acid molecules.

64. The non-natural occurring gene editing system of embodiment 63, wherein the nucleic acid of a) further comprises a hybridization domain A and the nucleic acid of b) further comprises a hybridization domain A', and wherein said hybridization domain A and hybridization domain A' are capable of specific hybridization.

65. The non-naturally occurring gene editing system of embodiment 64, wherein the hybridization domain A and the hybridization domain A' each comprise 10-50 complimentary nucleic acid residues, e.g., 20-40, e.g., 20, 21, 22, 23, 24, 25, 26, 27, 28, 29, 30, 31, 32, 33, 34, 35, 36, 37, 38, 39 or 40 nucleic acid residues.

66. The non-naturally-occurring gene editing system of any of embodiments 52-62, wherein the nucleic acid of a) and the nucleic acid of b) are disposed on the same molecule.

67. The non-naturally-occurring gene editing system any of embodiments 52-66, further comprising d) nucleic acid comprising a second targeting RNA capable of hybridizing with a target DNA sequence, e) nucleic acid comprising a second guide RNA capable of binding directly to the first or a second cleavage domain, and, optionally, f) a polypeptide comprising the second cleavage domain, wherein the polypeptide of f) comprises fewer than approximately 1200 amino acids.

68. The non-naturally occurring gene editing system of embodiment 67, wherein the polypeptide of f) comprises fewer than approximately 1100 amino acids.

69. The non-naturally occurring gene editing system of embodiment 67, wherein the polypeptide of f) comprises fewer than approximately 1000 amino acids.

70. The non-naturally occurring gene editing system of embodiment 67, wherein the polypeptide of f) comprises fewer than approximately 900 amino acids.

71. The non-naturally occurring gene editing system of embodiment 67, wherein the polypeptide of f) comprises fewer than approximately 800 amino acids.

72. The non-naturally occurring gene editing system of embodiment 67, wherein the polypeptide of f) comprises fewer than approximately 700 amino acids.

73. The non-naturally occurring gene editing system of embodiment 67, wherein the polypeptide of f) comprises fewer than approximately 600 amino acids.

74. The non-naturally occurring gene editing system of embodiment 67, wherein the polypeptide of f) comprises fewer than approximately 500 amino acids.

75. The non-naturally occurring gene editing system of embodiment 67, wherein the polypeptide of f) comprises fewer than approximately 400 amino acids.

76. The non-naturally occurring gene editing system of embodiment 67, wherein the polypeptide of f) comprises fewer than approximately 300 amino acids.

77. The non-naturally occurring gene editing system of embodiment 67, wherein the polypeptide of f) comprises fewer than approximately 200 amino acids.

78. The non-naturally-occurring gene editing system of any of the preceding embodiments, wherein one or more of the recited polypeptide components further comprises a nuclear localization sequence (NLS).

79. A chimeric polypeptide comprising a RNA-binding domain and a cleavage domain that are not naturally associated, wherein the polypeptide comprises fewer than approximately 1200 amino acids.

80. The chimeric polypeptide of embodiment 79, wherein the polypeptide comprises fewer than approximately 1100 amino acids.

81. The chimeric polypeptide of embodiment 79, wherein the polypeptide comprises fewer than approximately 1000 amino acids.

82. The chimeric polypeptide of embodiment 79, wherein the polypeptide comprises fewer than approximately 900 amino acids.

83. The chimeric polypeptide of embodiment 79, wherein the polypeptide comprises fewer than approximately 800 amino acids.

84. The chimeric polypeptide of embodiment 79, wherein the polypeptide comprises fewer than approximately 700 amino acids.

85. The chimeric polypeptide of embodiment 79, wherein the polypeptide comprises fewer than approximately 600 amino acids.

86. The chimeric polypeptide of embodiment 79, wherein the polypeptide comprises fewer than approximately 500 amino acids.

87. The chimeric polypeptide of embodiment 79, wherein the polypeptide comprises fewer than approximately 400 amino acids.

88. The chimeric polypeptide of embodiment 79, wherein the polypeptide comprises fewer than approximately 300 amino acids.

89. The chimeric polypeptide of embodiment 79, wherein the polypeptide comprises fewer than approximately 200 amino acids.

90. The chimeric polypeptide of any of embodiments 79-89, wherein the RNA binding domain is lysozyme, e.g., is SEQ ID NO: 2 or a guide RNA-binding fragment or analog thereof, or SEQ ID NO: 50, or a guide RNA-binding fragment or analog thereof.

91. The chimeric polypeptide of any of embodiments 79-89, wherein the RNA-binding domain is a fibronectin.

92. The chimeric polypeptide of any of embodiments 79-89, wherein the RNA-binding domain is an antibody or antigen-binding fragment or analog thereof.

93. The chimeric polypeptide of embodiment 92, wherein the antibody or antigen-binding fragment or analog thereof is an IgE.

94. The chimeric polypeptide of any of embodiments 79-89, wherein the RNA-binding domain is a fluorescent protein or functional fragment or analog thereof.

95. The chimeric polypeptide of embodiment 94, wherein the florescent protein or functional fragment or analog thereof is selected from the group consisting of the proteins identified in Tables 1-4, and an RNA-binding fragment or analog of any of the preceding.

96. The chimeric polypeptide of any of embodiments 79-95, wherein the cleavage domain comprises a functional fragment of a nuclease capable of inducing a double-strand break in DNA.

97. The chimeric polypeptide of embodiment 96, wherein the cleavage domain comprises a functional fragment of a GIY-YIG homing endonuclease.

98. The chimeric polypeptide of embodiment 97, wherein the cleavage domain comprises a functional fragment of I-TevI, e.g., SEQ ID NO: 13.

99. The chimeric polypeptide of any of embodiments 79-95, wherein the first cleavage domain comprises a functional fragment of a nuclease capable of inducing a single-strand break in DNA.

100. The chimeric polypeptide of embodiment 99, wherein the first cleavage domain comprises a functional fragment of a nuclease selected from the group consisting of FokI and PvuII, e.g., SEQ ID NO: 12 or a functional fragment thereof, or SEQ ID NO: 49 or a functional fragment thereof.

101. The chimeric polypeptide of any of embodiments 79-100, further comprising a NLS, e.g., is selected from the group consisting of SEQ ID NO: 22-37.

102. A nucleic acid, e.g., an isolated nucleic acid, comprising sequence encoding the gene editing system of any of embodiments 1-78 or the chimeric polypeptide of any of embodiments 79-101.

103. A vector comprising the nucleic acid of embodiment 102.

104. The vector of embodiment 103, wherein the vector is selected from the group consisting of a viral vector, a plasmid, a minicircle, and a nanoplasmid.

105. The vector of embodiment 104, wherein the vector is a viral vector.

106. The vector of embodiment 105, wherein the vector is selected from the group consisting of a lentivirus vector, adenovirus vector, adenoassociated vector and a retrovirus vector.

107. The vector of any of embodiments 103-106, comprising fewer than 10,000 nucleic acid residues.

108. The vector of any of embodiments 103-106, comprising fewer than 9000 nucleic acid residues.

109. The vector of any of embodiments 103-106, comprising fewer than 8000 nucleic acid residues.

110. The vector of any of embodiments 103-106, comprising fewer than 7000 nucleic acid residues.

111. The vector of any of embodiments 103-106, comprising fewer than 6000 nucleic acid residues.

112. The vector of any of embodiments 103-106, comprising fewer than 5000 nucleic acid residues.

113. The vector of any of embodiments 103-106, comprising fewer than 4000 nucleic acid residues.

114. The vector of any of embodiments 103-106, comprising fewer than 3000 nucleic acid residues.

115. A cell comprising: a) a gene editing system of any of embodiments 1-78; b) a chimeric polypeptide of any of embodiments 79-101; c) a nucleic acid of embodiment 102; or d) a vector of any of embodiments 103-114.

116. The cell of embodiment 115, wherein the cell is a human cell, e.g., a human stem or progenitor cell, e.g., a hematopoietic stem cell (HSC).

117. The cell of any of embodiments 115-116, wherein said cell is a T cell.

118. The cell of any of embodiments 115-116, wherein said cell is a NK cell.

119. The cell of any of embodiments 115-118, wherein said cell is a cancer cell.

120. A cell derived from the cell of any of embodiments 115-119, e.g., a daughter or progeny cell.

121. A method of making a cell, e.g., a cell of any of embodiments 115-120, comprising introducing into the cell a) a gene editing system of any of embodiments 1-78; b) a chimeric polypeptide of any of embodiments 79-101; c) a nucleic acid of embodiment 102; or d) a vector of any of embodiments 103-114.

122. The method of embodiment 121, wherein said introducing into the cell is performed in vitro.

123. The method of embodiment 121, wherein said introducing into the cell is performed ex vivo.

124. The method of embodiment 121, wherein said introducing into the cell is performed in vivo.

125. A method of modulating expression of a gene in a cell comprising administering to the cell a) a gene editing system of any of embodiments 1-78; b) a chimeric polypeptide of any of embodiments 79-101; c) a nucleic acid of embodiment 102; or d) a vector of any of embodiments 103-114, such that expression of a gene in a cell is modulated.
126. The method of embodiment 125, wherein expression of a gene in a cell is repressed.
127. The method of embodiment 125, wherein expression of a gene in a cell is activated.
128. A method of modifying an endogenous nucleic acid sequence, e.g., a gene, in a cell, comprising administering to the cell a) a gene editing system of any of embodiments 1-78; b) a chimeric polypeptide of any of embodiments 79-101; c) a nucleic acid of embodiment 102; or d) a vector of any of embodiments 103-114, such that an endogenous nucleic acid sequence, e.g., a gene, in a cell is modified.
129. The method of embodiment 128, wherein the modifying of an endogenous nucleic acid sequence comprises the deletion one or more endogenous nucleic acid residues.
130. The method of embodiment 128, wherein the modifying of an endogenous nucleic acid sequence comprises the replacement of one or more endogenous nucleic acid residues with nucleic acids from a donor nucleic acid molecule.
131. The method of any one of embodiments 125-130, wherein the administering to the cell is performed in vivo.
132. The method of any one of embodiments 125-130, wherein the administering to the cell is performed in vitro.
133. The method of any one of embodiments 125-130, wherein the administering to the cell is performed ex vivo.
134. A cell, wherein expression of one or more endogenous genes has been modulated by the method of any of embodiments 125-127 or 131-133.
135. A cell, wherein one or more endogenous nucleic acid sequences, e.g., genes, have been modified by the method of any of embodiments 128-134.
136. The cell of any one of embodiments 134-135, wherein the one or more endogenous genes comprises an HLA gene.
137. The cell of any one of embodiments 134-136, wherein the one or more endogenous genes comprises a TCR gene, e.g., TCRα or TCRβ.
138. The cell of any one of embodiments 134-137, wherein the one or more endogenous genes comprises an inhibitory molecule selected from the group consisting of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1 CD160, 2B4 and TGFR beta.
139. A cell of any of embodiments 134-135, wherein the one or more endogenous genes comprises a beta 2-microglogulin gene (B2M)
140. A cell derived from the cell of any of embodiments 134-139, e.g. a daughter cell or progeny cell.
141. A method of treating a subject, e.g., a mammal, having a disease associated with aberrant gene expression, e.g., a disease described herein, comprising administering to the subject an effective amount of a) a gene editing system of any of embodiments 1-78; b) a chimeric polypeptide of any of embodiments 79-101; c) a nucleic acid of embodiment 102; d) a vector of any of embodiments 103-114; or e) a cell of any of embodiments 115-120 or 134-140.
142. A gene editing system of any of embodiments 1-78, a chimeric polypeptide of any of embodiments 79-101, a nucleic acid of embodiment 102, a vector of any of embodiments 103-114, or a cell of any of embodiments 115-120 or 134-140, for use as a medicament.
143. A gene editing system of any of embodiments 1-78, a chimeric polypeptide of any of embodiments 79-101, a nucleic acid of embodiment 102, a vector of any of embodiments 103-114, or a cell of any of embodiments 115-120 or 134-140, for use in treating a disease associated with aberrant gene expression.

EXAMPLES

Example 1

Modulating eGFP Expression In Vitro by Transfection of Recombinant Proteins and Synthesized RNA Aptamers Specificity and cutting efficiency will be assayed, and the length of the linker between the guide RNA and the targeting RNA will be optimized in a model system. Recombinant proteins (comprising a guide RNA-binding domain and a nuclease domain) and synthesized one-piece nucleic acids comprising targeting RNA-guide RNA fusions will be first chemically transfected into the model system and tested using the eGFP disruption assay and analysis by FACS described by Fu et. al. (Fu Y, et al. High-frequency off-target mutagenesis induced by CRISPR-Cas nucleases in human cells. Nat Biotechnol. 2013; 31:822-826).

E. coli Expression of His-Tagged FOK1 Fusions

N- and C-terminal histidine tag fusions of the catalytic domain of FOK1 will be expressed recombinantly in E. coli as described previously (Fu Y, et al. Overproduction and crystallization of FokI restriction endonuclease. Nucleic Acids Res. 1989; 17:8741-8753). The constructs below will be created, wherein the guide RNA-binding domain is a histidine tag (either N-terminal or C-terminal to the FokI nuclease domain), and the nuclease domain is a catalytic fragment of FokI:

```
>catalyticFOK1_(G4S)2_8xHis
                                         (SEQ ID NO: 55)
KSELRHKLKYVPHEYIELIEIARNSTQDRILEMKVMEFFMKVYGYRG

KHLGGSRKPDGAIYTVGSPIDYGVIVDTKAYSGGYNLPIGQADEMQR

YVEENQTRNKHINPNEWWKVYPSSVTEFKFLFVSGHFKGNYKAQLTR

LNHITNCNGAVLSVEELLIGGEMIKAGTLTLEEVRRKFNNGEINFGG

GGSGGGGSHHHHHHHH

>8XHis_(G4S)2_catalyticFOK1
                                         (SEQ ID NO: 56)
RGSHHHHHHHHGGGGSGGGGSKSELRHKLKYVPHEYIELIEIARNST

QDRILEMKVMEFFMKVYGYRGKHLGGSRKPDGAIYTVGSPIDYGVIV

DTKAYSGGYNLPIGQADEMQRYVEENQTRNKHINPNEWWKVYPSSVT

EFKFLFVSGHFKGNYKAQLTRLNHITNCNGAVLSVEELLIGGEMIKA

GTLTLEEVRRKFNNGEINF

>8XHis_Fox1linker_catalyticFOK1
                                         (SEQ ID NO: 57)
RGSHHHHHHHHGSKDHILQFVIPNRLVKSELEEKKSELRHKLKYVPH

EYIELIEIARNSTQDRILEMKVMEFFMKVYGYRGKHLGGSRKPDGAI

YTVGSPIDYGVIVDTKAYSGGYNLPIGQADEMQRYVEENQTRNKHIN

PNEWWKVYPSSVTEFKFLFVSGHFKGNYKAQLTRLNHITNCNGAVLS

VEELLIGGEMIKAGTLTLEEVRRKFNNGEINF
```

Mammalian Expression of FOK1 Fusions

N- and C-terminal lysozyme fusions of the catalytic domain of FOK1 will be expressed recombinantly in HEK293 cells. A plasmid encoding the polypeptides will be synthesized. Transient expression and purification in HEK293F cells will be performed with standard methodology. 100 ml of HEK293F cells at $3 \times 10^6$ cells/ml will be transfected with 100 µg plasmid and 300 µg polyethylenimine. The cells will be incubated at 37° C. with 8% $CO_2$ and rotated at 80 rpm. After five days, the cells will be harvested by centrifugation at 3500 g for 20 minutes and the proteins purified using chromatography. The constructs below will be created, wherein the guide RNA-binding domain is a lysozyme (either N-terminal or C-terminal to the FokI nuclease domain), and the nuclease domain is a catalytic fragment of FokI:

```
>catalyticFOK1_(G4S)2_lysozyme
                                          (SEQ ID NO: 58)
KSELRHKLKYVPHEYIELIEIARNSTQDRILEMKVMEFFMKVYGYRG

KHLGGSRKPDGAIYTVGSPIDYGVIVDTKAYSGGYNLPIGQADEMQR

YVEENQTRNKHINPNEWWKVYPSSVTEFKFLFVSGHFKGNYKAQLTR

LNHITNCNGAVLSVEELLIGGEMIKAGTLTLEEVRRKFNNGEINFGG

GGSGGGGSKVFERCELARTLKRLGMDGYRGISLANWMCLAKWESGYN

TRATNYNAGDRSTDYGIFQINSRYWCNDGKTPGAVNACHLSCSALLQ

DNIADAVACAKRVVRDPQGIRAWVAWRNRCQNRDVRQYVQGCGV

>Lysozyme_(G4S)2_catalyticFOK1
                                          (SEQ ID NO: 59)
KVFERCELARTLKRLGMDGYRGISLANWMCLAKWESGYNTRATNYNA

GDRSTDYGIFQINSRYWCNDGKTPGAVNACHLSCSALLQDNIADAVA

CAKRVVRDPQGIRAWVAWRNRCQNRDVRQYVQGCGVGGGGSGGGGSK

SELRHKLKYVPHEYIELIEIARNSTQDRILEMKVMEFFMKVYGYRGK

HLGGSRKPDGAIYTVGSPIDYGVIVDTKAYSGGYNLPIGQADEMQRY

VEENQTRNKHINPNEWWKVYPSSVTEFKFLFVSGHFKGNYKAQLTRL

NHITNCNGAVLSVEELLIGGEMIKAGTLTLEEVRRKFNNGEINF

>lysozyme_Fox1linker_catalyticFOK1
                                          (SEQ ID NO: 60)
KVFERCELARTLKRLGMDGYRGISLANWMCLAKWESGYNTRATNYNA

GDRSTDYGIFQINSRYWCNDGKTPGAVNACHLSCSALLQDNIADAVA

CAKRVVRDPQGIRAWVAWRNRCQNRDVRQYVQGCGVGSKDHILQFVI

PNRLVKSELEEKKSELRHKLKYVPHEYIELIEIARNSTQDRILEMKV

MEFFMKVYGYRGKHLGGSRKPDGAIYTVGSPIDYGVIVDTKAYSGGY

NLPIGQADEMQRYVEENQTRNKHINPNEWWKVYPSSVTEFKFLFVSG

HFKGNYKAQLTRLNHITNCNGAVLSVEELLIGGEMIKAGTLTLEEVR

RKFNNGEINF
```

Synthesis of RNA (One-Piece Targeting RNA-Guide RNA Molecules)

Pairs of RNA molecules comprising guide RNA domains (which bind to the guide RNA-binding domain) and targeting domains that hybridize to sequences within a gene for eGFP will be selected based upon Tsai et. al. (Tsai S Q, et al. Dimeric CRISPR RNA-guided FokI nucleases for highly specific genome editing. Nat Biotechnol. 2014; 32:569-576). Initially, targeting domains from eGFP_Site47 pair and eGFP_Site81 pair of Tsai et al. will be utilized as eGFP targeting domains, and RNA molecules fusing these sequences to either the 3' or 5' end of either lysozyme-binding or histidine-binding aptamers (e.g., guide RNA domains that bind either a histidine tag or lysozyme) will be synthesized. Thymine linkers of 0, 5, 10 or 20 bases will be evaluated between the guide RNA sequence and the targeting RNA sequence to evaluate the optimal spacing for binding of the guide RNA sequence of the RNA molecule to the guide RNA-binding domain of the chimeric protein comprising the cleavage domain, and for cleavage of the target nucleic acid. Other sequences from the reference may also be evaluated.

```
Guide RNA sequences:
>anti-lysozyme guide RNA sequence
                                          (SEQ ID NO: 3)
GGGAAUGGAUCCACAUCUACGAAUUCAUCAGGGCUAAAGAGTGCAGA
GUUACUUAGUUCACUGCAGACUUGA >anti-histidine tag guide RNA sequence
                                          (SEQ ID NO: 8)
GGGUACGCUCAGGUAUAUUGGCGCCUUCGUGGAAUGUCAGUGCCUGG
ACGUGCAGU Linker sequences
>U5linker
                                          (SEQ ID NO: 66)
UUUUU >U10Linker
                                          (SEQ ID NO: 67)
UUUUUUUUUU >U20linker
                                          (SEQ ID NO: 68)
UUUUUUUUUUUUUUUUUUUU Targeting RNA sequences:
>eGFP_Site47_sense
                                          (SEQ ID NO: 69)
AAGUUCAGCGUGUCCGGCG >eGFP_Site47_antisense
                                          (SEQ ID NO: 70)
CCGUCCAGCUCGACCAGGA >EGFP_site81_sense
                                          (SEQ ID NO: 71)
CCGGCAAGCUGCCCGUGCCC >EGFP_site81_antisense
                                          (SEQ ID NO: 72)
CAGGGUCAGCUUGCCGUAGG
```

The following RNA constructs will be made using the sequences above:
5'-[targeting RNA]-[linker]-[guide RNA]-3'
5'-[targeting RNA]-[guide RNA]-3' 5'-[guide RNA]-[linker]-[targeting RNA]-3'
5'-[guide RNA]-[targeting RNA]-3'

Transfection of Proteins & RNA Molecules in U2OS.EGFP Reporter Cells

SenseRNAs (comprising a sense strand targeting RNA and guide RNA domains, as described above) will be preincubated with corresponding N-terminal guide RNA-binding domain-FokI fusion polypeptides (comprising the cleavage domain and the corresponding guide RNA-binding domain) to pre-assemble protein-RNA complexes, and then co-mixed with C-terminal FokI-guide RNA-binding domain fusion constructs preincubated with corresponding antisense RNAs (comprising an anti-sense strand targeting RNA and guide RNA domains, as described above). U2OS.EGFP reporter cells will be transfected using Lipofectamine™ CRISPRMAX™ Cas9 Transfection Reagent (Thermo-Fisher) according to the manufacturer's recommended protocols. Alternatively, cells may also be electroporated using the Amaxa® Cell Line Nucleofector® Kit V (Lonza) to ensure maximum transfection efficiency. EGFP disruption will be subsequently measured by flow cytometry analysis as described by Fu et. al.

To test the importance of orientation of the fusion proteins on the activity of the system, RNA constructs comprising a sense targeting RNA will be precinubated with corresponding C-terminal fusion FokI constructs. Similarly, RNA constructs comprising an anti-sense targeting RNA will be tested with N-terminal fusion FokI constructs.

Specificity of eGFP disruption will be initially evaluated by using only one of the sense/antisense RNA pairs. Random undesired cleavages may also be assessed via Sanger sequencing or T7EI assay (Reyon D, et al. FLASH assembly of TALENs for high-throughput genome editing. Nat Biotech. 2012; 30:460-465).

Synthesis of Plasmids Encoding RNA Molecules and Polypeptide Fusion Molecules

For those combinations which effectively disrupt EGFP, the next step will be synthesize plasmids encoding the corresponding guide-aptamers pairs and FOK1 fusions pairs with self-cleaving T2A peptides as described by Tsai et. al.

Transfection of Plasmids in U2OS.EGFP Reporter Cells

U2OS.EGFP reporter cells will be transfected using Lipofectamine™ Transfection Reagent (Thermo-Fisher) according to the manufacturer's recommended protocols. Alternatively, cells may also be electroporated using the Amaxa® Cell Line Nucleofector® Kit V (Lonza) to ensure maximum transfection efficiency. EGFP disruption will be subsequently measured by flow cytometry analysis as described by Fu et. al. Random undesired cleavages may also be assessed via Sanger sequencing or T7EI assay.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

We claim:

1. A non-naturally occurring gene editing system comprising:
   a) nucleic acid comprising a first targeting RNA capable of hybridizing with a target DNA sequence;
   b) nucleic acid comprising a first guide RNA capable of binding to a first guide RNA-binding domain; and
   c) a polypeptide comprising the first guide RNA-binding domain and a first cleavage domain,
   wherein the first guide RNA-binding domain is lysozyme.

2. The non-naturally occurring gene editing system of claim 1, wherein:
   (i) the nucleic acid of a) and the nucleic acid of b) are disposed on separate nucleic acid molecules, and optionally, wherein the nucleic acid of a) further comprises a hybridization domain A and the nucleic acid of b) further comprises a hybridization domain A', and wherein said hybridization domain A and hybridization domain A' are capable of specific hybridization; or
   (ii) the nucleic acid of a) and the nucleic acid of b) are disposed on the same molecule.

3. The non-naturally occurring gene editing system of claim 1, wherein the first cleavage domain comprises:
   (a) a functional fragment of a nuclease capable of inducing a double-strand break in DNA; or
   (b) a functional fragment of a nuclease capable of inducing a single-strand break in DNA.

4. The non-naturally occurring gene editing system of claim 3, wherein the first cleavage domain comprises:
   (a) a functional fragment of a GIY-YIG homing endonuclease;
   (b) a functional fragment of I-TevI, e.g., a functional fragment of SEQ ID NO: 13;
   (c) a functional fragment of FokI; or
   (d) a functional fragment of PvuII.

5. The non-naturally occurring gene editing system of claim 1, further comprising d) nucleic acid comprising a second targeting RNA capable of hybridizing with a second target DNA sequence, e) nucleic acid comprising a second guide RNA capable of binding to the first guide RNA-binding domain or a second guide-RNA-binding domain, and, optionally, f) a polypeptide comprising the second guide RNA-binding domain and a second cleavage domain, wherein the polypeptide of f) comprises:
   (i) fewer than approximately 1200 amino acids;
   (ii) fewer than approximately 1100 amino acids;
   (iii) fewer than approximately 1000 amino acids;
   (iv) fewer than approximately 900 amino acids;
   (v) fewer than approximately 800 amino acids;
   (vi) fewer than approximately 700 amino acids;
   (vii) fewer than approximately 600 amino acids;
   (viii) fewer than approximately 500 amino acids;
   (ix) fewer than approximately 400 amino acids;
   (x) fewer than approximately 300 amino acids; or
   (xi) fewer than approximately 200 amino acids.

6. The non-naturally occurring gene editing system of claim 5, wherein the first guide RNA and the second guide RNA comprise:
   (a) different sequences; or
   (b) the same sequence.

7. The non-naturally-occurring gene editing system of claim 1, wherein one or more of the recited polypeptide components further comprises a nuclear localization sequence (NLS).

8. A nucleic acid comprising sequence encoding the gene editing system of claim 1.

9. A vector comprising the nucleic acid of claim 8.

10. The vector of claim 9, wherein the vector is selected from the group consisting of a viral vector, a plasmid, a minicircle, a lentivirus vector, an adenovirus vector, an adenoassociated vector, a retrovirus vector and a nanoplasmid.

11. The vector of claim 9, comprising:
   (i) fewer than 10,000 nucleic acid residues;
   (ii) fewer than 9,000 nucleic acid residues;
   (iii) fewer than 8,000 nucleic acid residues;
   (iv) fewer than 7,000 nucleic acid residues;
   (v) fewer than 6,000 nucleic acid residues;
   (vi) fewer than 5,000 nucleic acid residues;
   (vii) fewer than 4,000 nucleic acid residues; or
   (viii) fewer than 3,000 nucleic acid residues.

12. A cell comprising a gene editing system of claim 1.

13. A method of (i) modulating expression of a gene in a cell, or (ii) modifying an endogenous nucleic acid sequence in a cell, comprising administering to the cell a gene editing system of claim 1, such that (i) expression of a gene in a cell is modulated or (ii) an endogenous nucleic acid sequence in a cell is modified.

14. The method of claim 13, wherein the administering to the cell is performed:
   (i) in vivo;
   (ii) in vitro; or
   (iii) ex vivo.

15. A method of treating a subject having a disease associated with aberrant gene expression, comprising administering to the subject an effective amount of a gene editing system of claim 1.

* * * * *